(12) United States Patent
Charifson et al.

(10) Patent No.: US 8,394,803 B2
(45) Date of Patent: *Mar. 12, 2013

(54) GYRASE INHIBITORS AND USES THEREOF

(75) Inventors: Paul Charifson, Framingham, MA (US); David Deininger, Waltham, MA (US); Joseph Drumm, Westborough, MA (US); Anne-Laure Grillot, Somerville, MA (US); Arnaud LeTiran, Lexington, MA (US); Yusheng Liao, Lexington, MA (US); Emanuele Perola, Cambridge, MA (US); Steven Ronkin, Watertown, MA (US); Dean Stamos, Carlsbad, CA (US); Tiansheng Wang, Concord, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 1871 days.

This patent is subject to a terminal disclaimer.

(21) Appl. No.: 11/593,418

(22) Filed: Nov. 6, 2006

(65) Prior Publication Data

US 2013/0030004 A1   Jan. 31, 2013

Related U.S. Application Data

(60) Provisional application No. 60/734,139, filed on Nov. 7, 2005.

(51) Int. Cl.
  *A61K 31/4184* (2006.01)
  *A61K 31/4427* (2006.01)
  *A61K 31/496* (2006.01)
  *A61K 31/4155* (2006.01)
  *C07D 235/04* (2006.01)
  *C07D 403/02* (2006.01)
  *C07D 403/14* (2006.01)
  *C07D 401/02* (2006.01)
  *C07D 401/14* (2006.01)

(52) U.S. Cl. .......... 514/252.13; 514/256; 514/338; 514/395; 544/295; 544/333; 546/273.4; 548/305.1; 548/306.1

(58) Field of Classification Search .......... 514/252.13, 514/256, 338, 395; 544/295, 333; 546/273.4; 548/305.1, 306.1
See application file for complete search history.

(56) References Cited

U.S. PATENT DOCUMENTS

| | | |
|---|---|---|
| 6,632,809 B2 | 10/2003 | Grillot et al. |
| RE40,245 E | 4/2008 | Grillot et al. |
| 7,495,014 B2 * | 2/2009 | Charifson et al. ............ 514/338 |
| 7,569,591 B2 * | 8/2009 | Charifson et al. ............ 514/338 |
| 2004/0043989 A1 | 3/2004 | Grillot et al. |
| 2005/0038247 A1 | 2/2005 | Charifson et al. |
| 2005/0256136 A1 | 11/2005 | Charifson et al. |
| 2006/0025424 A1 | 2/2006 | Charifson et al. |

FOREIGN PATENT DOCUMENTS

| | | |
|---|---|---|
| WO | 03/105846 A1 | 12/2003 |
| WO | 2005012292 | 2/2005 |

OTHER PUBLICATIONS

International Search Report from the counterpart PCT application No. PCT/US2006/043269; Date of completion of report: Apr. 10, 2007; Date of mailing of report: Apr. 20, 2007.

\* cited by examiner

*Primary Examiner* — Rebecca Anderson
*Assistant Examiner* — Samantha Shterengarts
(74) *Attorney, Agent, or Firm* — Michael C. Badia

(57) ABSTRACT

The present invention relates to compounds of formula I:

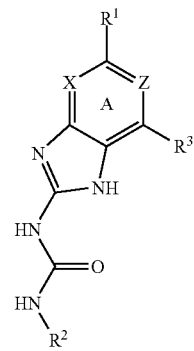

or a pharmaceutically acceptable salt thereof, that inhibit bacterial gyrase and/or Topo IV and pharmaceutically acceptable compositions comprising said compounds. These compounds, and compositions thereof, are useful in treating bacterial infection. Accordingly, the present invention also relates to methods for treating bacterial infections in mammals.

22 Claims, No Drawings

GYRASE INHIBITORS AND USES THEREOF

CROSS-REFERENCE TO RELATED APPLICATIONS

This application claims the benefit under 35 U.S.C. §119 of U.S. Provisional application Ser. No. 60/734,139 filed Nov. 7, 2005, the entire contents of which is incorporated herein by reference.

TECHNICAL FIELD OF THE INVENTION

This invention is in the field of medicinal chemistry and relates to compounds, and pharmaceutical compositions thereof, that inhibit bacterial gyrase and Topo IV. The compounds are useful as inhibitors of bacterial gyrase and Topo IV activity. The present invention also relates to methods for treating bacterial infections in mammals and to methods for decreasing bacterial quantity in a biological sample.

BACKGROUND OF THE INVENTION

Bacterial resistance to antibiotics has long been recognized, and it is today considered to be a serious worldwide health problem. As a result of resistance, some bacterial infections are either difficult to treat with antibiotics or even untreatable. This problem has become especially serious with the recent development of multiple drug resistance in certain strains of bacteria, such as *Streptococcus pneumoniae* (SP), *Mycobacterium tuberculosis*, and *Enterococcus*. The appearance of vancomycin resistant *enterococcus* was particularly alarming because vancomycin was formerly the only effective antibiotic for treating this infection, and had been considered for many infections to be the drug of "last resort". While many other drug-resistant bacteria do not cause life-threatening disease, such as enterococci, there is the fear that the genes which induce resistance might spread to more deadly organisms such as *Staphylococcus aureus*, where methicillin resistance is already prevalent (De Clerq, et al., *Current Opinion in Anti-infective Investigational Drugs*, 1999, 1, 1; Levy, "The Challenge of Antibiotic Resistance", *Scientific American*, March, 1998).

Another concern is how quickly antibiotic resistance can spread. For example, until the 1960's SP was universally sensitive to penicillin, and in 1987 only 0.02% of the SP strains in the U.S. were resistant. However, by 1995 it was reported that SP resistance to penicillin was about seven percent and as high as 30% in some parts of the U.S. (Lewis, FDA Consumer magazine (September, 1995); Gershman in *The Medical Reporter*, 1997).

Hospitals, in particular, serve as centers for the formation and transmission of drug-resistant organisms. Infections occurring in hospitals, known as nosocomial infections, are becoming an increasingly serious problem. Of the two million Americans infected in hospitals each year, more than half of these infections resist at least one antibiotic. The Center for Disease Control reported that in 1992, over 13,000 hospital patients died of bacterial infections that were resistant to antibiotic treatment (Lewis, "The Rise of Antibiotic-Resistant Infections", *FDA Consumer magazine, September*, 1995).

As a result of the need to combat drug-resistant bacteria and the increasing failure of the available drugs, there has been a resurgent interest in discovering new antibiotics. One attractive strategy for developing new antibiotics is to inhibit DNA gyrase, a bacterial enzyme necessary for DNA replication, and therefore, necessary for bacterial cell growth and division. Gyrase activity is also associated with events in DNA transcription, repair and recombination.

Gyrase is one of the topoisomerases, a group of enzymes, which catalyze the interconversion of topological isomers of DNA (see generally, Kornberg and Baker, *DNA Replication*, 2d Ed., Chapter 12, 1992, W.H. Freeman and Co.; Drlica, *Molecular Microbiology*, 1992, 6, 425; Drlica and Zhao, *Microbiology and Molecular Biology Reviews*, 1997, 61, 377). Gyrase itself controls DNA supercoiling and relieves topological stress that occurs when the DNA strands of a parental duplex are untwisted during the replication process. Gyrase also catalyzes the conversion of relaxed, closed circular duplex DNA to a negatively superhelical form, which is more favorable for recombination. The mechanism of the supercoiling reaction involves the wrapping of gyrase around a region of the DNA, double strand breaking in that region, passing a second region of the DNA through the break, and rejoining the broken strands. Such a cleavage mechanism is characteristic of a type II topoisomerase. The supercoiling reaction is driven by the binding of ATP to gyrase. The ATP is then hydrolyzed during the reaction. This ATP binding and subsequent hydrolysis cause conformational changes in the DNA-bound gyrase that are necessary for its activity. It has also been found that the level of DNA supercoiling (or relaxation) is dependent on the ATP/ADP ratio. In the absence of ATP, gyrase is only capable of relaxing supercoiled DNA.

Bacterial DNA gyrase is a 400 kilodalton protein tetramer consisting of two A (GyrA) and two B subunits (GyrB). Binding and cleavage of the DNA is associated with GyrA, whereas ATP is bound and hydrolyzed by the GyrB protein. GyrB consists of an amino-terminal domain, which has the ATPase activity, and a carboxy-terminal domain, which interacts with GyrA and DNA. By contrast, eukaryotic type II topoisomerases are homodimers that can relax negative and positive supercoils, but cannot introduce negative supercoils. Ideally, an antibiotic based on the inhibition of bacterial DNA gyrase would be selective for this enzyme and be relatively inactive against the eukaryotic type II topoisomerases.

The widely used quinolone antibiotics inhibit bacterial DNA gyrase. Examples of the quinolones include the early compounds such as nalidixic acid and oxolinic acid, as well as the later, more potent fluoroquinolones such as norfloxacin, ciprofloxacin, and trovafloxacin. These compounds bind to GyrA and stabilize the cleaved complex, thus inhibiting overall gyrase function, leading to cell death. However, drug resistance has also been recognized as a problem for this class of compounds (WHO Report, "Use of Quinolones in Food Animals and Potential Impact on Human Health", 1998). With the quinolones, as with other classes of antibiotics, bacteria exposed to earlier compounds often quickly develop cross-resistance to more potent compounds in the same class.

There are fewer known inhibitors that bind to GyrB. Examples include the coumarins, novobiocin and coumermycin A1, cyclothialidine, cinodine, and clerocidin. The coumarins have been shown to bind to GyrB very tightly. For example, novobiocin makes a network of hydrogen bonds with the protein and several hydrophobic contacts. While novobiocin and ATP do appear to bind within the ATP binding site, there is minimal overlap in the bound orientation of the two compounds. The overlapping portions are the sugar unit of novobiocin and the ATP adenine (Maxwell, *Trends in Microbiology*, 1997, 5, 102).

For coumarin-resistant bacteria, the most prevalent point mutation is at a surface arginine residue that binds to the carbonyl of the coumarin ring (Arg136 in *E. coli* GyrB).

While enzymes with this mutation show lower supercoiling and ATPase activity, they are also less sensitive to inhibition by coumarin drugs (Maxwell, *Mol. Microbiol.*, 1993, 9, 681).

Despite being potent inhibitors of gyrase supercoiling, the coumarins have not been widely used as antibiotics. They are generally not suitable due to their low permeability in bacteria, eukaryotic toxicity, and poor water solubility (Maxwell, *Trends in Microbiology*, 1997, 5, 102). It would be desirable to have a new, effective GyrB inhibitor that overcomes these drawbacks. Such an inhibitor would be an attractive antibiotic candidate, without a history of resistance problems that plague other classes of antibiotics.

Replication fork movement along circular DNA can generate topological changes both ahead of the replication complex as well as behind in the already replicated regions (Champoux, J. J., *Ann. Rev. Biochem.*, 2001, 70, 369-413). While DNA gyrase can introduce negative supercoils to compensate for the topological stresses ahead of the replication fork, some overwinding can diffuse back into the already replicated region of DNA resulting in precatenanes. If not removed, the presence of the precatenanes can result in interlinked (catenated) daughter molecules at the end of replication. TopoIV is responsible for separating the catenated daughter plasmids as well as removal of precatenanes formed during replication ultimately allowing for segregation of the daughter molecules into daughter cells. Topo IV is composed of two ParC and 2 parE subunits as a C2E2 tetramer (where the C and E monomers are homologous to the A and B monomers of gyrase, respectively) that requires ATP hydrolysis (at the N-terminus of the E subunit) to reset the enzyme to re-enter the catalytic cycle. Topo IV is highly conserved among bacteria and is essential for bacterial replication (Drlica and Zhao, *Microbiol. Mol. Biol. Rev.*, 1997, 61, 377).

While little attention has been paid to inhibitors that target ParE of TopoIV, the action of the newer quinolones on the ParC region has been widely studied (Hooper, D.C., *Clin. Infect. Dis.*, 2000, 31(Suppl 2): S24-28). It has been demonstrated that moxifloxacin and gatifloxacin have more balanced activities against Gyrase and TopoIV resulting in expanded Gram-positive coverage as well as lower levels of resistance caused primary-target mutation. In those cases, susceptibility is limited by the sensitivity of the second target to the antibacterial agent. Thus, agents that can effectively inhibit multiple essential targets can result in an expanded spectrum of potencies, improved antibacterial potencies, improved potency against single target mutants, and/or lower spontaneous rates of resistance.

As bacterial resistance to antibiotics has become an important public health problem, there is a continuing need to develop newer and more potent antibiotics. More particularly, there is a need for antibiotics that represent a new class of compounds not previously used to treat bacterial infection. Such compounds would be particularly useful in treating nosocomial infections in hospitals where the formation and transmission of resistant bacteria are becoming increasingly prevalent.

SUMMARY OF THE INVENTION

It has now been found that compounds of this invention, and pharmaceutically acceptable compositions thereof, are effective as inhibitors of gyrase and/or Topo IV. These compounds have the general formula I:

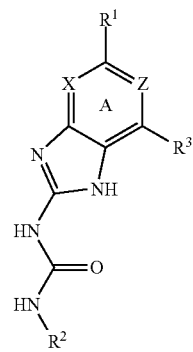

or a pharmaceutically acceptable salt thereof, wherein $R^1$, $R^2$, $R^3$, X, and Z are as defined below.

These compounds, and pharmaceutically acceptable compositions thereof, are useful for treating or lessening the severity of bacterial infections. In particular, the compounds of the present invention are useful in treating or lessening the severity of upper respiratory infections, lower respiratory infections, ear infections, pleuropulmonary and bronchial infections, urinary tract infections, intra-abdominal infections, cardiovascular infections, a blood stream infection, sepsis, CNS infections, skin and soft tissue infections, GI infections, bone and joint infections, genital infections, eye infections, or granulomatous infections.

DESCRIPTION OF THE INVENTION

The present invention relates to a compound of formula I:

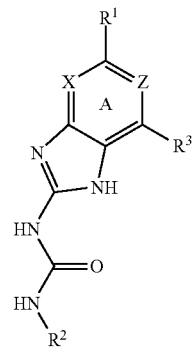

or a pharmaceutically acceptable salt thereof, wherein:
Z is selected from nitrogen or C—$R^4$;
X is selected from nitrogen or C—$R^4$;
$R^1$ is Q-Rx or $R^Y$; wherein
    Q is a $C_1$-$C_6$ aliphatic wherein up to three methylene units of Q are optionally and independently replaced by —NH—, —NR—, —O—, —S—, —OC(O)—, —C(O)CO—, —C(O)—, —C(S)—, —C(O)NH—, —C(O)NR—, —C(=N—CN), —NHCO—, —NRCO—, —NHC(O)O—, —NRC(O)O—, —SO$_2$NH—, —SO$_2$NR—, —NHSO$_2$—, —NRSO$_2$—, —NHC(O)NH—, —NRC(O)NH—, —NHC(O)NR—, —NRC(O)NR, —OC(O)NH—, —OC(O)NR—, —NHSO$_2$NH—, —NRSO$_2$NH—, —NHSO$_2$NR—, —NRSO$_2$NR—, —SO— or —SO$_2$—; wherein
    Q is optionally substituted with 1-3 independent occurrences of $R^Q$;

R is selected from $C_{1-6}$ aliphatic, $C_{3-10}$ cycloaliphatic, $C_{3-10}$ cycloaliphatic, or a 3-8 membered saturated or partially unsaturated monocyclic ring, or a 5-6 membered monocyclic aryl ring; each ring having 0-3 heteroatoms independently selected from nitrogen, oxygen, or sulfur; or an 8-12 membered saturated, partially unsaturated, or fully unsaturated bicyclic ring system having 0-5 heteroatoms independently selected from nitrogen, oxygen, or sulfur; wherein said monocyclic or bicyclic ring is optionally substituted with 1-3 independent occurrences of $R^T$, -T-Ar$^1$, halogen, oxo, thioxo, —OR$^T$, —SR$^T$, —N(R$^T$)$_2$, —NO$_2$, —C$_{1-4}$haloalkyl, —C$_{1-4}$haloalkoxy, —CN, —CO$_2$R$^T$, —COR$^T$, —CON(R$^T$)$_2$, —OCOR$^T$, —NR$^T$COR$^T$, —SO$_2$R$^T$, —SO$_2$N(R$^T$)$_2$, or —NR$^T$SO$_2$R$^T$;

wherein each $R^T$ is independently hydrogen or unsubstituted $C_{1-6}$ aliphatic; or any two $R^T$ or two R groups, on the same substituent or different substituents, together with the atom(s) to which each group is bound, optionally form a 3-8 membered saturated or partially unsaturated monocyclic ring, or a 5-6 membered monocyclic aryl ring having 0-3 heteroatoms independently selected from nitrogen, oxygen, or sulfur; wherein said monocyclic ring is optionally substituted with 1-3 independent occurrences of $R^R$, -T-Ar$^1$, halogen, oxo, thioxo, —OR$^R$, —SR$^R$, —N(R$^R$)$_2$, —NO$_2$, —C$_{1-4}$haloalkyl, —C$_{1-4}$haloalkoxy, —CN, —CO$_2$R$^R$, —COR$^R$, —CON(R$^R$)$_2$, —OCOR$^R$, —NR$^R$COR$^R$, —SO$_2$R$^R$, —SO$_2$N(R$^R$)$_2$, or —NR$^R$SO$_2$R$^R$; wherein each $R^R$ is independently hydrogen or unsubstituted $C_{1-6}$ aliphatic;

T is $(CH_2)_y$;

y is 0, 1, or 2;

Ar$^1$ is selected from:

(a) a 3-8 membered saturated or partially unsaturated ring;

(b) a 5-6 membered aryl ring;

(c) a 3-7 membered heterocyclic ring having 1-3 heteroatoms independently selected from nitrogen, oxygen, or sulfur;

(d) a 5-6 membered heteroaryl ring having 1-4 heteroatoms independently selected from nitrogen, oxygen, or sulfur; or (e) an 8-12 membered saturated, partially unsaturated, or fully unsaturated bicyclic ring system having 0-5 heteroatoms independently selected from nitrogen, oxygen, or sulfur; wherein Ar$^1$ is optionally substituted with 1-3 independent occurrences of —R$^W$, oxo, thioxo, —CO$_2$R$^W$, —OR$^W$, —N(R$^W$)$_2$, —SR$^W$, —NO$_2$, halogen, —CN, —C$_{1-4}$haloalkyl, —C$_{1-4}$haloalkoxy, —C(O)N(R$^W$)$_2$, —NR$^W$C(O)R$^W$, —SO$_2$R$^W$, —SO$_2$N(R$^W$)$_2$, —NR$^W$SO$_2$R$^W$, —NR$^W$CON(R$^W$)$_2$, —NR$^W$CO$_2$R$^W$, —COR$^W$, —OCOR$^W$, —OCON(R$^W$)$_2$, —SOR$^W$, —NR$^W$SO$_2$N(R$^W$)$_2$, —COCOR$^W$, —COCH$_2$COR$^W$, —OP(O)(OR$^W$)$_2$, —P(O)(OR$^W$)$_2$, —OP(O)$_2$OR$^W$, —P(O)$_2$OR$^W$, —PO(R$^W$)$_2$, or —OPO(R$^W$)$_2$;

each occurrence of $R^W$ is independently selected from hydrogen, $C_{1-6}$ aliphatic, a 3-8 membered saturated or partially unsaturated monocyclic ring, or a 5-6 membered monocyclic aryl ring; each ring having 0-4 heteroatoms independently selected from nitrogen, oxygen, or sulfur; wherein said $C_{1-6}$ aliphatic, said 3-8 membered or 5-6 membered monocyclic ring is optionally substituted with 1-3 independent occurrences of $R^S$, -T-Ar$^3$, halogen, oxo, thioxo, —OR$^S$, —SR$^S$, —N(R$^S$)$_2$, —NO$_2$, —C$_{1-4}$haloalkyl, —C$_{1-4}$haloalkoxy, —CN, —CO$_2$R$^S$, —COR$^S$, —CONHR$^S$, —OCOR$^S$, —NR$^S$COR$^S$, —SO$_2$R$^S$, —SO$_2$N(R$^S$)$_2$, or —NR$^S$SO$_2$R$^S$; wherein $R^S$ is hydrogen or unsubstituted $C_{1-6}$ aliphatic; and Ar$^3$ is selected from:

(a) a 3-8 membered saturated or partially unsaturated ring;

(b) a 5-6 membered aryl ring;

(c) a 3-7 membered heterocyclic ring having 1-3 heteroatoms independently selected from nitrogen, oxygen, or sulfur;

(d) a 5-6 membered heteroaryl ring having 1-4 heteroatoms independently selected from nitrogen, oxygen, or sulfur; or (e) an 8-12 membered saturated, partially unsaturated, or fully unsaturated bicyclic ring system having 0-5 heteroatoms independently selected from nitrogen, oxygen, or sulfur; wherein Ar$^3$ is optionally substituted with 1-3 independent occurrences of —R$^J$, oxo, thioxo, —CO$_2$R$^J$, —OR$^J$, —N(R$^J$)$_2$, —SR$^J$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SO$_2$R$^J$, —SO$_2$N(R$^J$)$_2$, —NR$^J$SO$_2$R$^J$, —NR$^J$CON(R$^J$)$_2$, —NR$^J$CO$_2$R$^J$, —OCOR$^J$, —OCON(R$^J$)$_2$, —SOR$^J$, —NR$^J$SO$_2$N(R$^J$)$_2$, —COCOR$^J$, —COCH$_2$COR$^J$, —OP(O)(OR$^J$)$_2$, —P(O)(OR$^J$)$_2$, —OP(O)$_2$OR$^J$, —P(O)$_2$OR$^J$, —PO(R$^J$)$_2$, or —OPO(R$^J$)$_2$;

each occurrence of $R^J$ is independently selected from hydrogen, $C_{1-6}$ aliphatic, a 3-8 membered saturated or partially unsaturated monocyclic ring, or a 5-6 membered monocyclic aryl ring; each ring having 0-4 heteroatoms independently selected from nitrogen, oxygen, or sulfur; wherein said $C_{1-6}$ aliphatic, said 3-8 membered or 5-6 membered monocyclic ring is optionally substituted with 1-3 independent occurrences of $R^I$, halogen, oxo, thioxo, —OR$^I$, —SR$^I$, —N(R$^I$)$_2$, —NO$_2$, —C$_{1-4}$haloalkyl, —C$_{1-4}$haloalkoxy, —CN, —CO$_2$R$^I$, —COR$^I$, —CONHR$^I$, —OCOR$^I$, —NR$^I$COR$^I$, —SO$_2$R$^I$, —SO$_2$N(R$^I$)$_2$, or —NR$^I$SO$_2$R$^I$; wherein $R^I$ is hydrogen or unsubstituted $C_{1-6}$ aliphatic;

$R^Q$ is selected from halogen, L, -(L$_n$)—R$^S$, -(L$_n$)—N(R$^S$)$_2$, -(L$_n$)—SR$^S$, -(L$_n$)—OR$^S$, -(L$_n$)—(C$_{3-10}$ cycloaliphatic), -(L$_n$)—(C$_{6-10}$ aryl), -(L$_n$)-(5-10 membered heteroaryl), -(L$_n$)-(5-10 membered heterocyclyl), oxo, thioxo, —C$_{1-4}$ haloalkoxy, —C$_{1-4}$haloalkyl, -(L$_n$)—NO$_2$, -(L$_n$)—CN, -(L$_n$)—CF$_3$, -(L$_n$)—OCF$_3$, —CO$_2$R$^S$, —COR$^S$, —OC(O)R$^S$ or —NR$^S$C(O)R$^S$;

wherein n is 0 or 1; or any two $R^Q$ or two $R^S$ groups, or any combination of an $R^Q$ group with an R or $R^S$ group on the same substituent or different substituents, together with the atom(s) to which each group is bound, optionally form a 3-8 membered saturated or partially unsaturated monocyclic ring, or a 5-6 membered monocyclic aryl ring; each ring having 0-3 heteroatoms independently selected from nitrogen, oxygen, or sulfur; wherein any of said monocyclic ring is optionally substituted with 1-3 independent occurrences of $R^O$, -T-Ar$^3$, halogen, oxo, thioxo, —OR$^O$, —SR$^O$, —N(R$^O$)$_2$, —NO$_2$, —C$_{1-4}$haloalkyl, —C$_{1-4}$haloalkoxy, —CN, —CO$_2$R$^O$, —COR$^O$, —CON(R$^O$)$_2$, —OCOR$^O$, —NR$^O$COR$^O$, —SO$_2$R$^O$, —SO$_2$N(R$^O$)$_2$, or —NR$^O$SO$_2$R$^O$; wherein $R^O$ is hydrogen or unsubstituted $C_{1-6}$ aliphatic;

L is $C_{1-6}$ aliphatic wherein up to three methylene units are replaced by —NH—, —NR$^S$—, —O—, —S—, —CO$_2$—, —OC(O)—, —C(O)CO—, —C(O)—, —C(S)—, —C(O)NH—, —C(O)NR$^5$—, —C(=N—CN), —NHCO—, —NR$^5$CO—, —NHC(O)O—, —NR$^5$C(O)O—, —SO$_2$NH—, —SO$_2$NR$^5$—, —NHSO$_2$—, —NR$^5$SO$_2$—, —NHC(O)NH—, —NR$^5$C(O)NH—, —NHC(O)NR$^5$—, —NR$^5$C(O)NR$^5$, —OC(O)NH—, —OC(O)NR$^5$—, —NHSO$_2$NH—, —NR$^5$SO$_2$NH—, —NHSO$_2$NR$^5$—, —NR$^5$SO$_2$NR$^5$—, —SO— or —SO$_2$—; wherein $R^5$ is selected from $C_{1-6}$ aliphatic, $C_{3-10}$ cycloaliphatic, or a 3-8-membered saturated or partially unsaturated monocyclic ring, or a 5-6 membered aryl ring; each ring having 0-3 heteroatoms independently selected from nitrogen, oxygen, or sulfur; or an 8-12 membered saturated, partially unsaturated, or fully unsaturated bicyclic ring system having 0-5 heteroatoms independently selected from nitrogen, oxygen, or sulfur; wherein each of said rings is optionally substituted with 1-3 independent occurrences of $R^N$, -T-Ar$^3$, halogen, oxo, —OR$^N$, —SR$^N$, —N(R$^N$)$_2$, —NO$_2$, —C$_{1-4}$haloalkyl, —C$_{1-4}$haloalkoxy, —CN, —CO$_2$R$^N$, —COR$^N$, —CON(R$^N$)$_2$, —OCOR$^N$, —NR$^N$COR$^N$, —SO$_2$R$^N$, —SO$_2$N(R$^N$)$_2$, or —NR$^N$SO$_2$R$^N$, wherein;

$R^N$ is hydrogen or unsubstituted $C_{1-6}$ aliphatic; or any two $R^5$ groups, on the same substituent or different substituents, together with the atom(s) to which each $R^5$ group is bound, optionally form a 3-8-membered saturated or partially unsaturated monocyclic ring, or a 5-6 membered aryl ring having 0-3 heteroatoms independently selected from nitrogen, oxygen, or sulfur; wherein said ring is optionally substituted with 1-3 independent occurrences of $R^M$, -T-Ar$^3$, halogen, oxo, thioxo, —OR$^M$, —SR$^M$, —N(R$^M$)$_2$, —NO$_2$, —C$_{1-4}$haloalkyl, —C$_{1-4}$haloalkoxy, —CN, —CO$_2$R$^M$, —COR$^M$, —CON(R$^M$)$_2$, —OCOR$^M$, —NR$^M$COR$^M$, —SO$_2$R$^M$, —SO$_2$N(R$^M$)$_2$, or —NR$^M$SO$_2$R$^M$; wherein, $R^M$ is hydrogen or unsubstituted $C_{1-6}$ aliphatic;

$R^X$ is selected from —R', halogen, =NR', —NO$_2$, —CN, —C$_{1-4}$haloalkyl, —C$_{1-4}$haloalkoxy, —OR', —SR', —N(R')$_2$, —NR'COR', —NR'CON(R')$_2$, —NR'CO$_2$R', —COR', —CO$_2$R', —OCOR', —CON(R')$_2$, —OCON(R')$_2$, —SOR', —SO$_2$R', —SO$_2$N(R')$_2$, —NR'SO$_2$R', —NR'SO$_2$N(R')$_2$, —COCOR', —COCH$_2$COR', —OP(O)(OR')$_2$, —P(O)(OR')$_2$, —OP(O)$_2$OR', —P(O)$_2$OR', —PO(R')$_2$, or —OPO(R')$_2$; wherein each occurrence of R' is independently hydrogen, $C_{1-6}$ aliphatic, $C_{3-10}$ cycloaliphatic, or a 3-8-membered saturated or partially unsaturated monocyclic ring or a 5-6 membered aryl ring having 0-3 heteroatoms independently selected from nitrogen, oxygen, or sulfur; or an 8-12 membered saturated, partially unsaturated, or fully unsaturated bicyclic ring system having 0-5 heteroatoms independently selected from nitrogen, oxygen, or sulfur; wherein each of said rings is optionally substituted with 1-3 independent occurrences of —R$^W$, -T-Ar$^1$, oxo, thioxo, —CO$_2$R$^W$, —OR$^W$, —N(R$^W$)$_2$, —SR$^W$, —NO$_2$, —C$_{1-4}$haloalkyl, halogen, —CN, —C(O)N(R$^W$)$_2$, —NR$^W$C(O)R$^W$, —SO$_2$R$^W$, —SO$_2$N(R$^W$)$_2$, —NR$^W$SO$_2$R$^W$, —NR$^W$CON(R$^W$)$_2$, —NR$^W$CO$_2$R$^W$, —COR$^W$, —OCOR$^W$, —OCON(R$^W$)$_2$, —SOR$^W$, —NR$^W$SO$_2$N(R$^W$)$_2$, —COCOR$^W$, —COCH$_2$COR$^W$, —OP(O)(OR$^W$)$_2$, —P(O)(OR$^W$)$_2$, —OP(O)$_2$OR$^W$, —P(O)$_2$OR$^W$, —PO(R$^W$)$_2$, or —OPO(R$^W$)$_2$; or two occurrences of R$^W$, two occurrences of R', or one R$^W$ and one R' are taken together with the atom(s) to which they are bound to optionally form a 3-8-membered saturated or partially unsaturated monocyclic ring or a 5-6 membered aryl ring having 0-3 heteroatoms independently selected from nitrogen, oxygen, or sulfur; or an 8-12 membered saturated, partially unsaturated, or fully unsaturated bicyclic ring system having 0-5 heteroatoms independently selected from nitrogen, oxygen, or sulfur; wherein said monocyclic or bicyclic ring is optionally substituted with 1-3 independent occurrences of R$^T$, -T-Ar$^3$, halogen, oxo, thioxo, —OR$^T$, —SR$^T$, —N(R$^T$)$_2$, —NO$_2$, —C$_{1-4}$haloalkoxy, —CN, —CO$_2$R$^T$, —COR$^T$, —CON(R$^T$)$_2$, —OCOR$^T$, —NR$^T$COR$^T$, —SO$_2$R$^T$, —SO$_2$N(R$^T$)$_2$, or —NR$^T$SO$_2$R$^T$;

$R^Y$ is selected from —R$^K$, halogen, —NO$_2$, —CN, —C$_{1-4}$haloalkoxy, —OR', —SR', —N(R')$_2$, —NR'COR', —NR'CON(R')$_2$, —NR'CO$_2$R', —COR', —CO$_2$R', —OCOR', —CON(R')$_2$, —OCON(R')$_2$, —C(R')=NOR', —C(R')=NOH, —C(R')=NR', —C(R')=N—N(R')$_2$, —SOR', —SO$_2$R', —SO$_2$N(R')$_2$, —NR'SO$_2$R', —NR'SO$_2$N(R')$_2$, —COCOR', —COCH$_2$COR', —C(O)C(O)N(R'$^2$)R'—OP(O)(OR')$_2$, —P(O)(OR')$_2$, —OP(O)$_2$OR', —P(O)$_2$OR', —PO(R')$_2$, or —OPO(R')$_2$;

$R^K$ is selected from hydrogen, $C_{1-6}$ aliphatic, $C_{3-10}$ cycloaliphatic, or a 3-8-membered saturated, or partially unsaturated monocyclic ring having 0-3 heteroatoms independently selected from nitrogen, oxygen, or sulfur; or an 8-12 membered saturated or partially unsaturated bicyclic ring system having 0-5 heteroatoms independently selected from nitrogen, oxygen, or sulfur, wherein said $C_{1-6}$ aliphatic, $C_{3-10}$ cycloaliphatic, or said monocyclic or bicyclic ring is optionally substituted with 1-4 independent occurrences of —R$^W$, -T-Ar$^1$, oxo, thioxo, —CO$_2$R$^W$, —OR$^W$, —N(R$^W$)$_2$, —SR$^W$, —NO$_2$, —C$_{1-4}$haloalkyl, —C$_{1-4}$haloalkoxy, halogen, —CN, —C(O)N(R$^W$)$_2$, —NR$^W$C(O)R$^W$, —SO$_2$R$^W$, —SO$_2$N(R$^W$)$_2$, —NR$^W$SO$_2$R$^W$, —NR$^W$CON(R$^W$)$_2$, —NR$^W$CO$_2$R$^W$, —COR$^W$, —OCOR$^W$, —OCON(R$^W$)$_2$, —SOR$^W$, —NR$^W$SO$_2$N(R$^W$)$_2$, —COCOR$^W$, —COCH$_2$COR$^W$, —OP(O)(OR$^W$)$_2$, —P(O)(OR$^W$)$_2$, —OP(O)$_2$OR$^W$, —P(O)$_2$OR$^W$, —PO(R$^W$)$_2$, or —OPO(R$^W$)$_2$;

wherein any nitrogen atom in any of said rings is optionally substituted with —R$^+$, —N(R$^+$)$_2$, —COR$^+$, —CO$_2$R$^+$, —COCOR$^+$, —COCH$_2$COR$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$, wherein;

$R^+$ is hydrogen, a $C_{1-6}$ aliphatic, phenyl, —O(Ph), —CH$_2$(Ph), —(CH$_2$)$_{1-2}$(Ph), —CH=CH(Ph); or an unsubstituted 5-6 membered heteroaryl or heterocyclic ring having one to four heteroatoms independently selected from oxygen, nitrogen, or sulfur, wherein said aliphatic group or said phenyl ring of R$^+$ is optionally substituted with 1-3 independent occurrences of —NH$_2$, —NH(C$_{1-4}$ aliphatic), —N(C$_{1-4}$ aliphatic)$_2$, halogen, —C$_{1-4}$ aliphatic, —OH, —O(C$_{1-4}$ aliphatic), —NO$_2$, —CN, —CO$_2$H, —CO$_2$(C$_{1-4}$ aliphatic), —C$_{1-4}$haloalkyl, —C$_{1-4}$haloalkoxy, wherein said C$_{1-4}$ aliphatic groups of R$^+$ are unsubstituted;

$R^2$ is an unsubstituted $C_{1-4}$ aliphatic group; and $R^3$ is selected from —Ar$^2$, —C(O)NHR$^Y$, —C(O)N(R$^Y$)$_2$, —C(O)R$^Y$, —CO$_2$R$^Y$, —C(O)C(O)N(R$^Y$)$_2$, —SO$_2$R$^Y$, —SO$_2$N(R$^V$)$_2$, —SO$_2$NHR$^V$, —C(R$^V$)=NOR$^V$, —C(R$^V$)=NOH, or —C(R$^V$)=NR$^V$;
wherein
each R$^V$ is independently selected from -T-Ar$^1$ or a C$_{1-6}$ aliphatic group; wherein said C$_{1-6}$ aliphatic group is optionally substituted with 1-3 groups independently selected from —R$^W$, -T-Ar$^1$, oxo, thioxo, —CO$_2$R$^W$, —OR$^W$, —N(R$^W$)$_2$, —SR$^W$, —NO$_2$, —C$_{1-4}$haloalkyl, —C$_{1-4}$haloalkoxy, halogen, —CN, —C(O)N(R$^W$)$_2$, —NR$^W$C(O)R$^W$, —SO$_2$R$^W$, —SO$_2$N(R$^W$)$_2$, —NR$^W$SO$_2$R$^W$, —NR$^W$CON(R$^W$)$_2$, —NR$^W$CO$_2$R$^W$, —COR$^W$, —OCOR$^W$, —OCON(R$^W$)$_2$, —SOR$^W$, —NR$^W$SO$_2$N(R$^W$)$_2$, —COCOR$^W$, —COCH$_2$COR$^W$, —OP(O)(OR$^W$)$_2$, —P(O)(OR$^W$)$_2$, —OP(O)$_2$OR$^W$, —P(O)$_2$OR$^W$, —PO(R$^W$)$_2$, or —OPO(R$^W$)$_2$;

Ar$^2$ is a 5-6 membered heteroaryl ring having 1-4 heteroatoms independently selected from nitrogen, oxygen, or sulfur; or a 5-6 membered heterocyclic ring having 1-3 heteroatoms independently selected from nitrogen, oxygen, or sulfur; provided that said ring has a hydrogen-bond acceptor in the position adjacent to the point of attachment to Ring A; wherein Ar$^2$ is optionally substituted with 1-3 groups independent occurrences of —R$^W$, -T-Ar$^1$, oxo, thioxo, —CO$_2$R$^W$, —OR$^W$, —N(R$^W$)$_2$, —SR$^W$, —NO$_2$, —C$_{1-4}$haloalkyl, —C$_{1-4}$haloalkoxy, halogen, —CN, —C(O)N(R$^W$)$_2$, —NR$^W$C(O)R$^W$, —SO$_2$R$^W$, —SO$_2$N(R$^W$)$_2$, —NR$^W$SO$_2$R$^W$, —NR$^W$CON(R$^W$)$_2$, —NR$^W$CO$_2$R$^W$, —COR$^W$, —OCOR$^W$, —OCON(R$^W$)$_2$, —SOR$^W$, —NR$^W$SO$_2$N(R$^W$)$_2$, —COCOR$^W$, —COCH$_2$COR$^W$, —OP(O)(OR$^W$)$_2$, —P(O)(OR$^W$)$_2$, —OP(O)$_2$OR$^W$, —P(O)$_2$OR$^W$, —PO(R$^W$)$_2$, or —OPO(R$^W$)$_2$; or two substituents on adjacent positions of Ar$^2$ may be taken together to form a 3-8-membered saturated or partially unsaturated monocyclic ring or a 5-6 membered aryl ring having 0-3 heteroatoms independently selected from nitrogen, oxygen, or sulfur; wherein said 3-8-membered or said 5-6 membered ring is optionally substituted with 1-3 independent occurrences of R$^T$, -T-Ar$^3$, halogen, oxo, thioxo, —OR$^T$, —SR$^T$, —N(R$^T$)$_2$, —NO$_2$, —C$_{1-4}$haloalkyl, —C$_{1-4}$haloalkoxy, —CN, —CO$_2$R$^T$, —COR$^T$, —CON(R$^T$)$_2$, —OCOR$^T$, —NR$^T$COR$^T$, —SO$_2$R$^T$, —SO$_2$N(R$^T$)$_2$, or —NR$^T$SO$_2$R$^T$;

wherein any nitrogen atom in any of said rings is optionally substituted with —R$^+$, —N(R$^+$)$_2$, —COR$^+$, —CO$_2$R$^+$, —COCOR$^+$, —COCH$_2$COR$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; and R$^4$ is selected from hydrogen or halogen; and
provided that the following compounds are excluded:
1-ethyl-3-(5-(2,3-dihydro-1-isopropyl-2-oxo-1H-imidazol-4-yl)-7-(pyrimidin-2-yl)-1H-benzo[d]imidazol-2-yl)urea; and
1-ethyl-3-(5-(1,1-dimethylurea)-7-(pyrimidin-2-yl)-1H-benzo[d]imidazol-2-yl)urea.

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic C$_3$-C$_8$ hydrocarbon or bicyclic C$_8$-C$_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl. Further examples of aliphatic groups include methyl, ethyl, propyl, butyl, isopropyl, isobutyl, vinyl, and sec-butyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydroimidazol-2-one.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl", "haloaliphatic", and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined herein below.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

Further examples of heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

An aryl (including aralkyl, aralkoxy, aryloxyalkyl and the like) or heteroaryl (including heteroaralkyl and heteroarylalkoxy and the like) group may contain one or more substituents and thus may be "optionally substituted". Unless otherwise defined above and herein, suitable substituents on the unsaturated carbon atom of an aryl or heteroaryl group are generally selected from halogen; —R°; —OR°; —SR°; phenyl (Ph) optionally substituted with R°; —O(Ph) optionally substituted with R°; —(CH$_2$)$_{1-2}$(Ph), optionally substituted with R°; —CH═CH(Ph), optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —C(O)CH$_2$C(O)R°; —CO$_2$R°; —C(O)R°; —C(S)R°; —C(O)N(R°)$_2$; —C(S)N(R°)$_2$; —OC(O)N(R°)$_2$; —OC(O)R°; —C(O)N(OR°)R°; —C(NOR°)R°; —S(O)$_2$R°; —S(O)$_3$R°; —SO$_2$N(R°)$_2$; —S(O)R°; —NR°SO$_2$N(R°)$_2$; —NR°SO$_2$R°; —N(OR°R°; —C(═NH)—N(R°)$_2$; —P(O)$_2$R°; —PO(R°)$_2$; —OPO(R°)$_2$; —(CH$_2$)$_{0-2}$NHC(O)R°; phenyl (Ph) optionally substituted with R°; —O(Ph) optionally substituted with R°; —(CH$_2$)$_{1-2}$(Ph), optionally substituted with R°; or —CH═CH(Ph), optionally substituted with R°; wherein each independent occurrence of R° is selected from hydrogen, optionally substituted C$_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of R°, on the same substituent or different substituents, taken together with the atom(s) to which each R° group is bound, to form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group of R° are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$ aliphatic, wherein each of the foregoing C$_{1-4}$aliphatic groups of R° is unsubstituted.

An aliphatic or heteroaliphatic group, or a non-aromatic heterocyclic ring may contain one or more substituents and thus may be "optionally substituted". Unless otherwise defined above and herein, suitable substituents on the saturated carbon of an aliphatic or heteroaliphatic group, or of a non-aromatic heterocyclic ring are selected from those listed above for the unsaturated carbon of an aryl or heteroaryl group and additionally include the following: ═O, ═S, ═NNHR*, ═NN(R*)$_2$, ═NNHC(O)R*, ═NNHCO$_2$(alkyl), ═NNHSO$_2$(alkyl), or ═NR*, where each R* is independently selected from hydrogen or an optionally substituted C$_{1-6}$ aliphatic group.

Unless otherwise defined above and herein, optional substituents on the nitrogen of a non-aromatic heterocyclic ring are generally selected from —R⁺, —N(R⁺)₂, —C(O)R⁺, —CO₂R⁺, —C(O)C(O)R⁺, —C(O)CH₂C(O)R⁺, —SO₂R⁺, —SO₂N(R⁺)₂, —C(=S)N(R⁺)₂, —C(=NH)—N(R⁺)₂, or —NR⁺SO₂R⁺; wherein R⁺ is hydrogen, an optionally substituted $C_{1-6}$ aliphatic, optionally substituted phenyl, optionally substituted —O(Ph), optionally substituted —CH₂(Ph), optionally substituted —(CH₂)$_{1-2}$(Ph); optionally substituted —CH=CH(Ph); or an unsubstituted 5-6-membered heteroaryl or heterocyclic ring having one to four heteroatoms independently selected from oxygen, nitrogen, or sulfur, or, notwithstanding the definition above, two independent occurrences of R⁺, on the same substituent or different substituents, taken together with the atom(s) to which each R⁺ group is bound, form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group or the phenyl ring of R⁺ are selected from —NH₂, —NH($C_{1-4}$ aliphatic), —N($C_{1-4}$ aliphatic)₂, halogen, $C_{1-4}$ aliphatic, —OH, —O($C_{1-4}$ aliphatic), —NO₂, —CN, —CO₂H, —CO₂($C_{1-4}$ aliphatic), —O(halo $C_{1-4}$ aliphatic), or halo($C_{1-4}$ aliphatic), wherein each of the foregoing $C_{1-4}$ aliphatic groups of R⁺ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of R° (or R⁺, R, R' or any other variable similarly defined herein), are taken together with the atom(s) to which they are bound to form an optionally substituted 3-12 membered saturated, partially unsaturated monocyclic or bicyclic ring or an optionally substituted 5-6 membered fully unsaturated monocyclic or an 8-12 membered bicyclic ring having 0-4 heteroatoms independently selected from nitrogen, oxygen, or sulfur.

Exemplary rings that are formed when two independent occurrences of R° (or R⁺, R, R' or any other variable similarly defined herein), are taken together with the atom(s) to which each variable is bound include, but are not limited to the following: a) two independent occurrences of R° (or R⁺, R, R' or any other variable similarly defined herein) that are bound to the same atom and are taken together with that atom to form a ring, for example, N(R°)₂, where both occurrences of R° are taken together with the nitrogen atom to form a piperidin-1-yl, piperazin-1-yl, or morpholin-4-yl group; and b) two independent occurrences of R° (or R⁺, R, R' or any other variable similarly defined herein) that are bound to different atoms and are taken together with both of those atoms to form a ring, for example where a phenyl group is substituted with two occurrences of

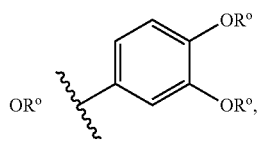

these two occurrences of R° are taken together with the oxygen atoms to which they are bound to form a fused 6-membered oxygen containing ring:

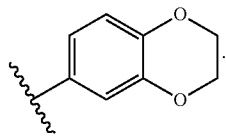 [SMILES: *c1ccc2c(c1)OCCO2]

It will be appreciated that a variety of other rings can be formed when two independent occurrences of R° (or R⁺, R, R' or any other variable similarly defined herein) are taken together with the atom(s) to which each variable is bound and that the examples detailed above are not intended to be limiting.

In some embodiments, an alkyl or aliphatic chain can be optionally interrupted with another atom or group. This means that a methylene unit of the alkyl or aliphatic chain is optionally replaced with said other atom or group. Examples of such atoms or groups would include, but are not limited to, —NR—, —O—, —S—, —CO₂—, —OC(O)—, —C(O)CO—, —C(O)—, —C(O)NR—, —C(=N—CN), —NRCO—, —NRC(O)O—, —SO₂NR—, —NRSO₂—, —NRC(O)NR—, —OC(O)NR—, —NRSO₂NR—, —SO—, or —SO₂—, wherein R is defined herein. Unless otherwise specified, the optional replacements form a chemically stable compound. Optional interruptions can occur both within the chain and at either end of the chain; i.e. both at the point of attachment and/or also at the terminal end. Two optional replacements can also be adjacent to each other within a chain so long as it results in a chemically stable compound. Unless otherwise specified, if the replacement or interruption occurs at the terminal end, the replacement atom is bound to an H on the terminal end. For example, if —CH₂CH₂CH₃ were optionally interrupted with —O—, the resulting compound could be —OCH₂CH₃, —CH₂OCH₃, or —CH₂CH₂OH.

The term "hydrogen bond acceptor", as used herein, means an atom capable of accepting a hydrogen bond. A typical hydrogen bond acceptor is a sulfur, oxygen, or nitrogen atom, especially a nitrogen that is sp²-hybridized, an ether oxygen, or a thioether sulfur. A preferred hydrogen bond acceptor is a nitrogen that is sp²-hybridized.

In the definition of radical Ar² herein, the term "provided that said ring has a hydrogen-bond acceptor in the position adjacent to the point of attachment to Ring A" is used. In said term, the "position adjacent to the point of attachment to Ring A" is further exemplified in the following structural example:

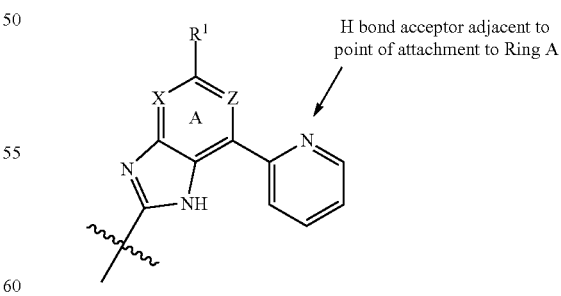

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

According to one embodiment of compounds of formula I of the present invention,

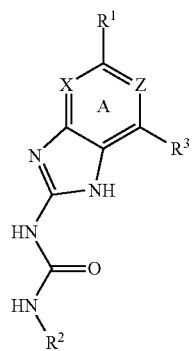

I or a pharmaceutically acceptable salt thereof, wherein:

Z is selected from nitrogen or C—$R^4$;
X is selected from nitrogen or C—$R^4$;
$R^1$ is Q-Rx or $R^Y$; wherein
  Q is a $C_1$-$C_6$ aliphatic wherein up to three methylene units of Q are optionally and independently replaced by —NH—, —NR—, —O—, —S—, —$CO_2$—, —OC(O)—, —C(O)CO—, —C(O)—, —C(S)—, —C(O)NH—, —C(O)NR—, —C(=N—CN), —NHCO—, —NRCO—, —NHC(O)O—, —NRC(O)O—, —$SO_2$NH—, —$SO_2$NR—, —NHSO$_2$—, —NRSO$_2$—, —NHC(O)NH—, —NRC(O)NH—, —NHC(O)NR—, —NRC(O)NR, —OC(O)NH—, —OC(O)NR—, —NHSO$_2$NH—, —NRSO$_2$NH—, —NHSO$_2$NR—, —NRSO$_2$NR—, —SO— or —$SO_2$—; wherein
  Q is optionally substituted with 1-3 independent occurrences of $R^Q$;
  R is selected from $C_{1-6}$ aliphatic, $C_{3-10}$ cycloaliphatic, $C_{3-10}$ cycloaliphatic, or a 3-8 membered saturated or partially unsaturated monocyclic ring, or a 5-6 membered monocyclic aryl ring; each ring having 0-3 heteroatoms independently selected from nitrogen, oxygen, or sulfur; or an 8-12 membered saturated, partially unsaturated, or fully unsaturated bicyclic ring system having 0-5 heteroatoms independently selected from nitrogen, oxygen, or sulfur; wherein said monocyclic or bicyclic ring is optionally substituted with 1-3 independent occurrences of $R^T$, -T-$Ar^1$, halogen, oxo, thioxo, —$OR^T$, —$SR^T$, —N($R^T$)$_2$, —$NO_2$, —$C_{1-4}$haloalkyl, —$C_{1-4}$haloalkoxy, —CN, —$CO_2R^T$, —$COR^T$, —CON($R^T$)$_2$, —$OCOR^T$, —$NR^TCOR^T$, —$SO_2R^T$, —$SO_2$N($R^T$)$_2$, or —$NR^TSO_2R^T$;

wherein
each $R^T$ is independently hydrogen or unsubstituted $C_{1-6}$ aliphatic; or
any two $R^T$ or two R groups, on the same substituent or different substituents, together with the atom(s) to which each group is bound, optionally form a 3-8 membered saturated or partially unsaturated monocyclic ring, or a 5-6 membered monocyclic aryl ring having 0-3 heteroatoms independently selected from nitrogen, oxygen, or sulfur; wherein said monocyclic ring is optionally substituted with 1-3 independent occurrences of $R^R$, -T-$Ar^1$, halogen, oxo, thioxo, —$OR^R$, —$SR^R$, —N($R^R$)$_2$, —$NO_2$, —$C_{1-4}$haloalkyl, —$C_{1-4}$haloalkoxy, —CN, —$CO_2R^R$, —$COR^R$, —CON($R^R$)$_2$, —$OCOR^R$, —$NR^RCOR^R$, —$SO_2R^R$, —$SO_2$N($R^R$)$_2$, or —$NR^RSO_2R^R$; wherein each $R^R$ is independently hydrogen or unsubstituted $C_{1-6}$ aliphatic;

T is (CH$_2$)$_y$;
y is 0, 1, or 2;
$Ar^1$ is selected from:
(a) a 3-8 membered saturated or partially unsaturated ring;
(b) a 5-6 membered aryl ring;
(c) a 3-7 membered heterocyclic ring having 1-3 heteroatoms independently selected from nitrogen, oxygen, or sulfur;
(d) a 5-6 membered heteroaryl ring having 1-4 heteroatoms independently selected from nitrogen, oxygen, or sulfur; or
(e) an 8-12 membered saturated, partially unsaturated, or fully unsaturated bicyclic ring system having 0-5 heteroatoms independently selected from nitrogen, oxygen, or sulfur; wherein
$Ar^1$ is optionally substituted with 1-3 independent occurrences of —$R^W$, oxo, thioxo, —$CO_2R^W$, —$OR^W$, —N($R^W$)$_2$, —$SR^W$, —$NO_2$, halogen, —CN, —$C_{1-4}$haloalkyl, —$C_{1-4}$haloalkoxy, —C(O)N($R^W$)$_2$, —$NR^WC(O)R^W$, —$SO_2R^W$, —$SO_2$N($R^W$)$_2$, —$NR^WSO_2R^W$, —$NR^WCON(R^W$)$_2$, —$NR^WCO_2R^W$, —$COR^W$, —$OCOR^W$, —OCON($R^W$)$_2$, —$SOR^W$, —$NR^WSO_2N(R^W$)$_2$, —$COCOR^W$, —$COCH_2COR^W$, —OP(O)(O$R^W$)$_2$, —P(O)(O$R^W$)$_2$, —OP(O)$_2$O$R^W$, —P(O)$_2$O$R^W$, —PO($R^W$)$_2$, or —OPO($R^W$)$_2$;
each occurrence of $R^W$ is independently selected from hydrogen, $C_{1-6}$ aliphatic, a 3-8 membered saturated or partially unsaturated monocyclic ring, or a 5-6 membered monocyclic aryl ring; each ring having 0-4 heteroatoms independently selected from nitrogen, oxygen, or sulfur; wherein said $C_{1-6}$ aliphatic, said 3-8 membered or 5-6 membered monocyclic ring is optionally substituted with 1-3 independent occurrences of $R^S$, -T-$Ar^3$, halogen, oxo, thioxo, —$OR^S$, —$SR^S$, —N($R^S$)$_2$, —$NO_2$, —$C_{1-4}$haloalkyl, —$C_{1-4}$haloalkoxy, —CN, —$CO_2R^S$, —$COR^S$, —$CONHR^S$, —$OCOR^S$, —$NR^SCOR^S$, —$SO_2R^S$, —$SO_2$N($R^S$)$_2$, or —$NR^SSO_2R^S$; wherein
$R^S$ is hydrogen or unsubstituted $C_{1-6}$ aliphatic; and
$Ar^3$ is selected from:
(a) a 3-8 membered saturated or partially unsaturated ring;
(b) a 5-6 membered aryl ring;
(c) a 3-7 membered heterocyclic ring having 1-3 heteroatoms independently selected from nitrogen, oxygen, or sulfur;

(d) a 5-6 membered heteroaryl ring having 1-4 heteroatoms independently selected from nitrogen, oxygen, or sulfur; or (e) an 8-12 membered saturated, partially unsaturated, or fully unsaturated bicyclic ring system having 0-5 heteroatoms independently selected from nitrogen, oxygen, or sulfur; wherein $Ar^3$ is optionally substituted with 1-3 independent occurrences of —$R^J$, oxo, thioxo, —$CO_2R^J$, —$OR^J$, —$N(R^J)_2$, —$SR^J$, —$NO_2$, halogen, —CN, —$C_{1-4}$haloalkyl, —$C_{1-4}$haloalkoxy, —$C(O)N(R^J)_2$, —$NR^JC(O)R^J$, —$SO_2R^J$, —$SO_2N(R^J)_2$, —$NR^JSO_2R^J$, —$NR^JCON(R^J)_2$, —$NR^JCO_2R^J$, —$OCOR^J$, —$OCON(R^J)_2$, —$SOR^J$, —$NR^JSO_2N(R^J)_2$, —$COCOR^J$, —$COCH_2COR^J$, —$OP(O)(OR^J)_2$, —$P(O)(OR^J)_2$, —$OP(O)_2OR^J$, —$P(O)_2OR^J$, —$PO(R^J)_2$, or —$OPO(R^J)_2$;

each occurrence of $R^J$ is independently selected from hydrogen, $C_{1-6}$ aliphatic, a 3-8 membered saturated or partially unsaturated monocyclic ring, or a 5-6 membered monocyclic aryl ring; each ring having 0-4 heteroatoms independently selected from nitrogen, oxygen, or sulfur; wherein said $C_{1-6}$ aliphatic, said 3-8 membered or 5-6 membered monocyclic ring is optionally substituted with 1-3 independent occurrences of R', halogen, oxo, thioxo, —$OR^I$, —$SR^I$, —$N(R^I)_2$, —$NO_2$, —$C_{1-4}$haloalkyl, —$C_{1-4}$haloalkoxy, —CN, —$CO_2R^I$, —$COR^I$, —$CONHR^I$, —$OCOR^I$, —$NR^ICOR^I$, —$SO_2R^I$, —$SO_2N(R^I)_2$, or —$NR^ISO_2R^I$; wherein $R^1$ is hydrogen or unsubstituted $C_{1-6}$ aliphatic;

$R^Q$ is selected from halogen, L, -($L_n$)—$R^S$, -($L_n$)—$N(R^S)_2$, -($L_n$)—$SR^S$, -($L_n$)—$OR^S$, -($L_n$)—($C_{3-10}$ cycloaliphatic), -($L_n$)—($C_{6-10}$ aryl), -($L_n$)-(5-10 membered heteroaryl), -($L_n$)-(5-10 membered heterocyclyl), oxo, thioxo, —$C_{1-4}$ haloalkoxy, —$C_{1-4}$haloalkyl, -($L_n$)—$NO_2$, -($L_n$)—CN, -($L_n$)—$CF_3$, -($L_n$)—$OCF_3$, —$CO_2R^S$, —$COR^S$, —$OC(O)R^S$ or —$NR^SC(O)R^S$; wherein n is 0 or 1; or any two $R^Q$ or two $R^S$ groups, or any combination of an $R^Q$ group with an R or $R^S$ group on the same substituent or different substituents, together with the atom(s) to which each group is bound, optionally form a 3-8 membered saturated or partially unsaturated monocyclic ring, or a 5-6 membered monocyclic aryl ring; each ring having 0-3 heteroatoms independently selected from nitrogen, oxygen, or sulfur; wherein any of said monocyclic ring is optionally substituted with 1-3 independent occurrences of $R^O$, -T-$Ar^3$, halogen, oxo, thioxo, —$OR^O$, —$SR^O$, —$N(R^O)_2$, —$NO_2$, —$C_{1-4}$haloalkyl, —$C_{1-4}$haloalkoxy, —CN, —$CO_2R^O$, —$COR^O$, —$CON(R^O)_2$, —$OCOR^O$, —$NR^OCOR^O$, —$SO_2R^O$, —$SO_2N(R^O)_2$, or —$NR^OSO_2R^O$; wherein $R^O$ is hydrogen or unsubstituted $C_{1-6}$ aliphatic;

L is $C_{1-6}$ aliphatic wherein up to three methylene units are replaced by —NH—, —$NR^5$—, —O—, —S—, —$CO_2$—, —OC(O)—, —C(O)CO—, —C(O)—, —C(S)—, —C(O)NH—, —C(O)$NR^5$—, —C(=N—CN), —NHCO—, —$NR^5$CO—, —NHC(O)O—, —$NR^5$C(O)O—, —$SO_2$NH—, —$SO_2NR^5$—, —$NHSO_2$—, —$NR^5SO_2$—, —NHC(O)NH—, —$NR^5$C(O)NH—, —NHC(O)$NR^5$—, —$NR^5$C(O)$NR^5$, —OC(O)NH—, —OC(O)$NR^5$—, —$NHSO_2$NH—, —$NR^5SO_2$NH—, —$NHSO_2NR^5$—, —$NR^5SO_2NR^5$—, —SO— or —$SO_2$—; wherein $R^5$ is selected from $C_{1-6}$ aliphatic, $C_{3-10}$ cycloaliphatic, or a 3-8-membered saturated or partially unsaturated monocyclic ring, or a 5-6 membered aryl ring; each ring having 0-3 heteroatoms independently selected from nitrogen, oxygen, or sulfur; or an 8-12 membered saturated, partially unsaturated, or fully unsaturated bicyclic ring system having 0-5 heteroatoms independently selected from nitrogen, oxygen, or sulfur; wherein each of said rings is optionally substituted with 1-3 independent occurrences of $R^N$, -T-$Ar^3$, halogen, oxo, —$OR^N$, —$SR^N$, —$N(R^N)_2$, —$NO_2$, —$C_{1-4}$haloalkyl, —$C_{1-4}$haloalkoxy, —CN, —$CO_2R^N$, —$COR^N$, —$CON(R^N)_2$, —$OCOR^N$, —$NR^NCOR^N$, —$SO_2R^N$, —$SO_2N(R^N)_2$, or —$NR^NSO_2R^N$, wherein;

$R^N$ is hydrogen or unsubstituted $C_{1-6}$ aliphatic; or any two $R^5$ groups, on the same substituent or different substituents, together with the atom(s) to which each $R^5$ group is bound, optionally form a 3-8-membered saturated or partially unsaturated monocyclic ring, or a 5-6 membered aryl ring having 0-3 heteroatoms independently selected from nitrogen, oxygen, or sulfur; wherein said ring is optionally substituted with 1-3 independent occurrences of $R^M$, -T-$Ar^3$, halogen, oxo, thioxo, —$OR^M$, —$SR^M$, —$N(R^M)_2$, —$NO_2$, —$C_{1-4}$haloalkyl, —$C_{1-4}$haloalkoxy, —CN, —$CO_2R^M$, —$COR^M$, —$CON(R^M)_2$, —$OCOR^M$, —$NR^MCOR^M$, —$SO_2R^M$, —$SO_2N(R^M)_2$, or —$NR^MSO_2R^M$; wherein, $R^M$ is hydrogen or unsubstituted $C_{1-6}$ aliphatic;

$R^X$ is selected from —R', halogen, =NR', —$NO_2$, —CN, —$C_{1-4}$haloalkyl, —$C_{1-4}$haloalkoxy, —OR', —SR', —N(R')$_2$, —NR'COR', —NR'CON(R')$_2$, —NR'$CO_2$R', —COR', —$CO_2$R', —OCOR', —CON(R')$_2$, —OCON(R')$_2$, —SOR', —$SO_2$R', —$SO_2$N(R')$_2$, —NR'$SO_2$R', —NR'$SO_2$N(R')$_2$, —COCOR', —COCH$_2$COR', —OP(O)(OR')$_2$, —P(O)(OR')$_2$, —OP(O)$_2$OR', —P(O)$_2$OR', —PO(R')$_2$, or —OPO(R')$_2$; wherein each occurrence of R' is independently hydrogen, $C_{1-6}$ aliphatic, $C_{3-10}$ cycloaliphatic, or a 3-8-membered saturated or partially unsaturated monocyclic ring or a 5-6 membered aryl ring having 0-3 heteroatoms independently selected from nitrogen, oxygen, or sulfur; or an 8-12 membered saturated, partially unsaturated, or fully unsaturated bicyclic ring system having 0-5 heteroatoms independently selected from nitrogen, oxygen, or sulfur; wherein each of said rings is optionally substituted with 1-3 independent occurrences of —$R^W$, -T-$Ar^1$, oxo, thioxo, —$CO_2R^W$, —$OR^W$, —$N(R^W)_2$, —$SR^W$, —$NO_2$, —$C_{1-4}$haloalkyl, —$C_{1-4}$haloalkoxy, halogen, —CN, —$C(O)N(R^W)_2$, —$NR^WC(O)R^W$, —$SO_2R^W$, —$SO_2N(R^W)_2$, —$NR^WSO_2R^W$, —$NR^WCON(R^W)_2$, —$NR^WCO_2R^W$, —$COR^W$, —$OCOR^W$, —$OCON(R^W)_2$, —$SOR^W$, —$NR^WSO_2N(R^W)_2$, —$COCOR^W$, —$COCH_2COR^W$, —$OP(O)(OR^W)_2$, —$P(O)(OR^W)_2$, —$OP(O)_2OR^W$, —$P(O)_2OR^W$, —$PO(R^W)_2$, or —$OPO(R^W)_2$; or two occurrences of $R^W$, two occurrences of R', or one $R^W$ and one R' are taken together with the atom(s) to which they are bound to optionally form a 3-8-membered saturated or partially unsaturated monocyclic ring or a 5-6 membered aryl ring having 0-3 heteroatoms independently selected from nitrogen, oxygen, or sulfur; or an 8-12 membered saturated, partially unsaturated, or fully unsaturated bicyclic ring system having 0-5 heteroatoms independently selected from nitrogen, oxygen, or sulfur; wherein said monocyclic or bicyclic ring is optionally substituted with 1-3 independent occurrences of $R^T$, -T-$Ar^3$, halogen, oxo, thioxo, —$OR^T$, —$SR^T$, —$N(R^T)_2$, —$NO_2$, —$C_{1-4}$haloalkyl, —$C_{1-4}$haloalkoxy, —CN, —$CO_2R^T$, —$COR^T$, —$CON(R^T)_2$, —$OCOR^T$, —$NR^TCOR^T$, —$SO_2R^T$, —$SO_2N(R^T)_2$, or —$NR^TSO_2R^T$;

$R^Y$ is selected from —$R^K$, halogen, —$NO_2$, —CN, —$C_{1-4}$haloalkyl, —$C_{1-4}$haloalkoxy, —OR', —SR', —N(R')$_2$, —NR'COR', —NR'CON(R')$_2$, —NR'CO$_2$R', —COR', —CO$_2$R', —OCOR', —CON(R')$_2$, —OCON(R')$_2$, —C(R')=NOR', —C(R')=NOH, —C(R')=NR', —C(R')=N—N(R')$_2$, —SOR', —SO$_2$R', —SO$_2$N(R')$_2$, —NR'SO$_2$R', —NR'SO$_2$N(R')$_2$, —COCOR', —COCH$_2$COR', —C(O)C(O)N(R'$^2$)R'—OP(O)(OR')$_2$, —P(O)(OR')$_2$, —OP(O)$_2$OR', —P(O)$_2$OR', —PO(R')$_2$, or —OPO(R')$_2$;

$R^K$ is selected from hydrogen, $C_{1-6}$ aliphatic, $C_{3-10}$ cycloaliphatic, or a 3-8-membered saturated, or partially unsaturated monocyclic ring having 0-3 heteroatoms independently selected from nitrogen, oxygen, or sulfur; or an 8-12 membered saturated or partially unsaturated bicyclic ring system having 0-5 heteroatoms independently selected from nitrogen, oxygen, or sulfur, wherein said $C_{1-6}$ aliphatic, $C_{3-10}$ cycloaliphatic, or said monocyclic or bicyclic ring is optionally substituted with 1-4 independent occurrences of —$R^W$, -T-$Ar^1$, oxo, thioxo, —$CO_2R^W$, —$OR^W$, —$N(R^W)_2$, —$SR^W$, —$NO_2$, —$C_{1-4}$haloalkyl, —$C_{1-4}$haloalkoxy, halogen, —CN, —$C(O)N(R^W)_2$, —$NR^WC(O)R^W$, —$SO_2R^W$, —$SO_2N(R^W)_2$, —$NR^WSO_2R^W$, —$NR^WCON(R^W)_2$, —$NR^WCO_2R^W$, —$COR^W$, —$OCOR^W$, —$OCON(R^W)_2$, —$SOR^W$, —$NR^WSO_2N(R^W)_2$, —$COCOR^W$, —$COCH_2COR^W$, —$OP(O)(OR^W)_2$, —$P(O)(OR^W)_2$, —$OP(O)_2OR^W$, —$P(O)_2OR^W$, —$PO(R^W)_2$, or —$OPO(R^W)_2$;

wherein any nitrogen atom in any of said rings is optionally substituted with —$R^+$, —$N(R^+)_2$, —$COR^+$, —$CO_2R^+$, —$COCOR^+$, —$COCH_2COR^+$, —$SO_2R^+$, —$SO_2N(R^+)_2$, —$C(=S)N(R^+)_2$, —$C(=NH)$—$N(R^+)_2$, or —$NR^+SO_2R^+$, wherein;

$R^+$ is hydrogen, a $C_{1-6}$ aliphatic, phenyl, —O(Ph), —CH$_2$(Ph), —(CH$_2$)$_{1-2}$(Ph), —CH=CH(Ph); or an unsubstituted 5-6 membered heteroaryl or heterocyclic ring having one to four heteroatoms independently selected from oxygen, nitrogen, or sulfur, wherein said aliphatic group or said phenyl ring of $R^+$ is optionally substituted with 1-3 independent occurrences of —NH$_2$, —NH(C$_{1-4}$ aliphatic), —N(C$_{1-4}$ aliphatic)$_2$, halogen, —C$_{1-4}$ aliphatic, —OH, —O(C$_{1-4}$ aliphatic), —NO$_2$, —CN, —CO$_2$H, —CO$_2$(C$_{1-4}$ aliphatic), —C$_{1-4}$haloalkyl, —C$_{1-4}$haloalkoxy, wherein said C$_{1-4}$ aliphatic groups of $R^+$ are unsubstituted;

$R^2$ is an unsubstituted $C_{1-4}$ aliphatic group; and $R^3$ is selected from —$Ar^2$, —C(O)NHR$^V$, —C(O)N(R$^V$)$_2$, —C(O)R$^V$, —CO$_2$R$^V$, —C(O)C(O)N(R$^V$)$_2$, —SO$_2$R$^V$, —SO$_2$N(R$^V$)$_2$, —SO$_2$NHR$^V$, —C(R$^V$)=NOR$^V$, —C(R$^V$)=NOH, or —C(R$^V$)=NR$^V$;

wherein
each R$^V$ is independently selected from -T-$Ar^1$ or a $C_{1-6}$ aliphatic group; wherein said $C_{1-6}$ aliphatic group is optionally substituted with 1-3 groups independently selected from —$R^W$, -T-$Ar^1$, oxo, thioxo, —$CO_2R^W$, —$OR^W$, —$N(R^W)_2$, —$SR^W$, —$NO_2$, —$C_{1-4}$haloalkyl, —$C_{1-4}$haloalkoxy, halogen, —CN, —$C(O)N(R^W)_2$, —$NR^WC(O)R^W$, —$SO_2R^W$, —$SO_2N(R^W)_2$, —$NR^WSO_2R^W$, —$NR^WCON(R^W)_2$, —$NR^WCO_2R^W$, —$COR^W$, —$OCOR^W$, —$OCON(R^W)_2$, —$SOR^W$, —$NR^WSO_2N(R^W)_2$, —$COCOR^W$, —$COCH_2COR^W$, —$OP(O)(OR^W)_2$, —$P(O)(OR^W)_2$, —$OP(O)_2OR^W$, —$P(O)_2OR^W$, —$PO(R^W)_2$, or —$OPO(R^W)_2$;

$Ar^2$ is a 5-6 membered heteroaryl ring having 1-4 heteroatoms independently selected from nitrogen, oxygen, or sulfur; or a 5-6 membered heterocyclic ring having 1-3 heteroatoms independently selected from nitrogen, oxygen, or sulfur; provided that said ring has a hydrogen-bond acceptor in the position adjacent to the point of attachment to Ring A; wherein $Ar^2$ is optionally substituted with 1-3 groups independent occurrences of —$R^W$, -T-$Ar^1$, oxo, thioxo, —$CO_2R^W$, —$OR^W$, —$N(R^W)_2$, —$SR^W$, —$NO_2$, —$C_{1-4}$haloalkyl, —$C_{1-4}$haloalkoxy, halogen, —CN, —$C(O)N(R^W)_2$, —$NR^WC(O)R^W$, —$SO_2R^W$, —$SO_2N(R^W)_2$, —$NR^WSO_2R^W$, —$NR^W CON(R^W)_2$, —$NR^WCO_2R^W$, —$COR^W$, —$OCOR^W$, —$OCON(R^W)_2$, —$SOR^W$, —$NR^WSO_2N(R^W)_2$, —$COCOR^W$, —$COCH_2COR^W$, —$OP(O)(OR^W)_2$, —$P(O)(OR^W)_2$, —$OP(O)_2OR^W$, —$P(O)_2OR^W$, —$PO(R^W)_2$, or —$OPO(R^W)_2$; or two substituents on adjacent positions of $Ar^2$ may be taken together to form a 3-8-membered saturated or partially unsaturated monocyclic ring or a 5-6 membered aryl ring having 0-3 heteroatoms independently selected from nitrogen, oxygen, or sulfur; wherein said 3-8-membered or said 5-6 membered ring is optionally substituted with 1-3 independent occurrences of $R^T$, -T-$Ar^3$, halogen, oxo, thioxo, —$OR^T$, —$SR^T$, —$N(R^T)_2$, —$NO_2$, —$C_{1-4}$haloalkyl, —$C_{1-4}$haloalkoxy, —CN, —$CO_2R^T$, —$COR^T$, —$CON(R^T)_2$, —$OCOR^T$, —$NR^TCOR^T$, —$SO_2R^T$, —$SO_2N(R^T)_2$, or —$NR^TSO_2R^T$;

wherein any nitrogen atom in any of said rings is optionally substituted with —$R^+$, —$N(R^+)_2$, —$COR^+$, —$CO_2R^+$, —$COCOR^+$, —$COCH_2COR^+$, —$SO_2R^+$, —$SO_2N(R^+)_2$, —$C(=S)N(R^+)_2$, —$C(=NH)$—$N(R^+)_2$, or —$NR^+SO_2R^+$; and $R^4$ is selected from hydrogen or halogen.

According to one embodiment of compounds of formula I of the present invention, $R^3$ is $Ar^2$.

According to another embodiment, suitable $Ar^2$ moieties are set forth in Table 1 below.

TABLE 1

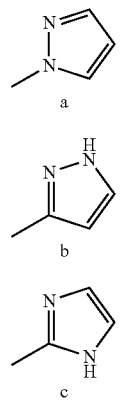

TABLE 1-continued
| | | |
|---|---|---|
| 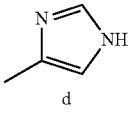 d | 5 | 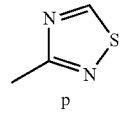 p |
| 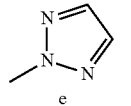 e | 10 | 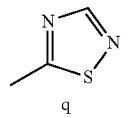 q |
| 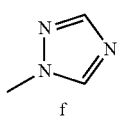 f | 15 | 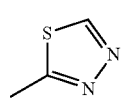 r |
| 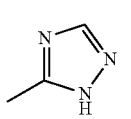 g | 20 | 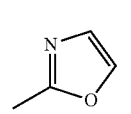 s |
| 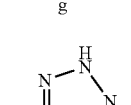 h | 25 | 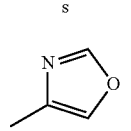 t |
| 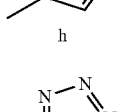 i | 30 | 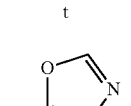 u |
| 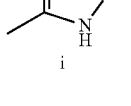 j | 35 | 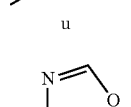 v |
| 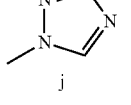 k | 40 | 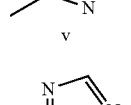 w |
| 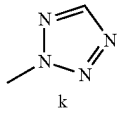 l | 45 | 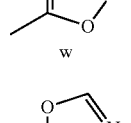 x |
| 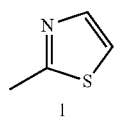 m | 50 | 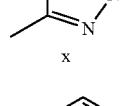 y |
| 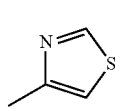 n | 55 | 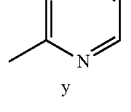 z |
| 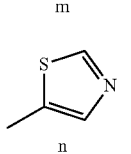 o | 60 | 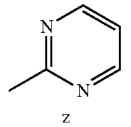 aa |
| | 65 | |

TABLE 1-continued

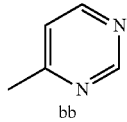
bb

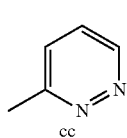
cc

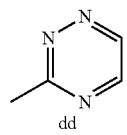
dd

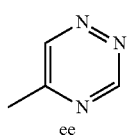
ee

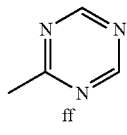
ff

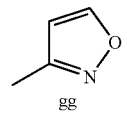
gg

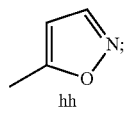
hh wherein each $Ar^2$ is optionally substituted as defined herein.

According to one embodiment, Ring $Ar^2$ of formula I is a 5-membered heteroaryl ring having 1-4 heteroatoms independently selected from nitrogen, oxygen, or sulfur, provided that said ring has a hydrogen-bond acceptor in the position adjacent to the point of attachment to Ring A, wherein said Ring A is optionally substituted as defined herein supra.

According to another embodiment, Ring $Ar^2$ of formula I is a 6-membered heteroaryl ring having 1-3 nitrogens, provided that said ring has a nitrogen atom in the position adjacent to the point of attachment to Ring A, wherein said Ring $Ar^2$ is optionally substituted as defined herein supra.

In certain embodiments, Ring $Ar^2$ moieties of formula I are selected from rings a, b, c, d, e, f, g, h, i, j, k, l, m, p, q, r, s, t, u, v, w, x, y, z, aa, bb, cc, dd, ee, ff, gg, wherein each Ring $Ar^2$ is optionally substituted as defined herein supra.

In other embodiments, the Ring $Ar^2$ moieties of formula I are selected from the following optionally substituted rings;

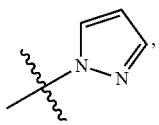 , 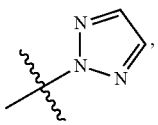 , 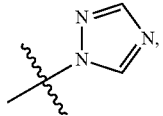 ,

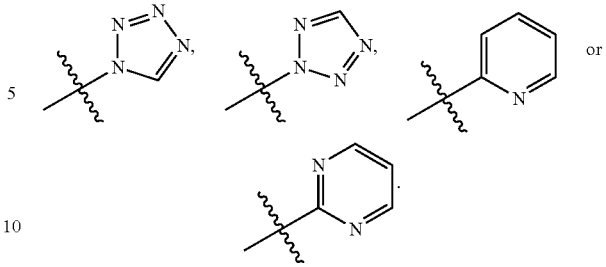

In another embodiment, the Ring $Ar^2$ moieties of formula I are selected from the following optionally substituted rings:

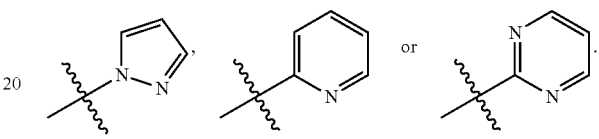

According to another embodiment, the Ring $Ar^2$ moieties of formula I are selected from the following rings:

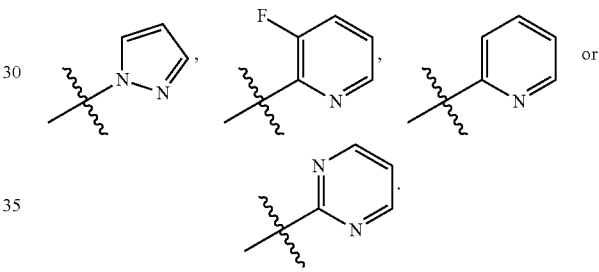

In another embodiment, the Ring $Ar^2$ moieties of formula I are selected from the following rings:

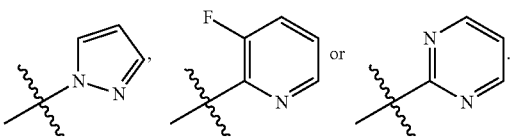 [SMILES: *n1cccn1 ; *c1ncccc1F ; *c1ncccn1]

According to another embodiment, the $R^3$ moieties of formula I are selected from $C(O)NHR^V$, $C(O)R^V$, $C(R^V)=NOR^V$, $C(R^V)=NOH$, or $CO_2R^V$, wherein: each $R^V$ is independently selected from a $C_{1-4}$ aliphatic group or $T-Ar^2$, wherein:
said $C_{1-4}$ aliphatic group is substituted with 0-2 groups independently selected from halogen, $OR^W$, or $N(R^W)_2$;
T is $(CH_2)_y$, wherein y is 0, 1, or 2; and
$Ar^2$ is selected from pyrrolidinyl, furanyl, thiazolyl, tetrahydrofuranyl, pyrimidinyl, pyrazinyl, pyridyl, piperidinyl, imidazolyl, pyridazinyl, isoxazolyl, pyrazolyl, tetrahydropyranyl, or cyclopentene, wherein:
Ar is substituted with 0-2 groups independently selected from $R^W$, oxo, $OR^W$, or $N(R^W)_2$.

According to another embodiment, the $R^3$ moieties of formula I are selected from $CO_2CH_3$, $C(R^V)=NOR^V$, $C(R^V)=NOH$, or $C(O)NHR^V$, wherein each $R^V$ is independently selected from the following groups: cyclopropyl, $CH_2CH_2$(1- methylpyrrolidin-2-yl), CH$_2$(1-ethylpyrrolidin-2-yl), CH$_2$CH$_2$pyrrolidin-1-yl, CH$_2$furan-2-yl, thiazol-2-yl, CH$_2$tetrahydrofuran-2-yl, pyrimidin-2-yl, pyrazin-2-yl, CH$_2$pyridin-2-yl, pyridin-3-yl, pyridin-4-yl, CH(CH$_3$)CH$_2$OCH$_3$, CH$_2$CF$_3$, CH$_2$CH$_3$, CH$_2$CH$_2$N(CH$_2$CH$_3$)$_2$, CH$_2$CH$_2$N(CH$_3$)$_2$, CH$_2$CH$_2$OCH$_3$, CH$_2$CCH, CH$_2$cyclopropyl, 1-ethylpiperidin-3-yl, CH(CH$_2$CH$_3$)CH$_2$OCH$_3$, CH(CH$_3$)CH$_2$OCH$_3$, dihydro-furan-2-on-3-yl, 1-methyl-1,5-dihydro-imidazol-4-on-2-yl, pyridazin-4-yl, imidazol-2-yl, 3H-pyridin-4-on-2-yl, pyrimidin-5-yl, cyclpenten-4-yl, 1-methyl-imidazol-2-yl, tetrahydropyranyl, CH$_2$(3-methyl-isoxazol-5-yl), or CH$_2$(1,3-dimethyl-pyrazol-5-yl).

According to another embodiment, R$^3$ is selected from C(R$^V$)=NOR$^V$ or C(R$^V$)=NOH.

According to another embodiment, R$^3$ is C(O)R$^V$.

According to another embodiment, the R$^2$ group of formula I is selected from methyl, ethyl, isopropyl, or cyclopropyl.

In another embodiment, the R$^2$ group of formula I is ethyl.

According to another embodiment of formula I, Z is C—R$^4$. In another embodiment, Z is C—R$^4$ and R$^4$ is hydrogen. In yet another embodiment, Z is C—R$^4$ and R$^4$ is halogen. In another embodiment, Z is C—R$^4$ and R$^4$ is fluorine.

According to another embodiment of formula I, X is C—R$^4$. In another embodiment, X is C—R$^4$ and R$^4$ is hydrogen. In yet another embodiment, X is C—R$^4$ and R$^4$ is halogen. In yet another embodiment, X is C—R$^4$ and R$^4$ is fluorine.

According to another embodiment of formula I, Z is C—R$^4$. In another embodiment, Z is C—R$^4$ and R$^4$ is hydrogen.

According to another embodiment of formula I, Z is nitrogen and X is nitrogen.

According to another embodiment of formula I, Z is nitrogen, X is C—R$^4$, and R$^4$ is hydrogen. In yet another embodiment, Z is nitrogen, X is C—R$^4$, and R$^4$ is halogen. In yet another embodiment, Z is nitrogen, X is C—R$^4$, and R$^4$ is fluorine.

According to another embodiment of formula I, X is nitrogen, Z is C—R$^4$, and R$^4$ is hydrogen. In yet another embodiment, X is nitrogen, Z is C—R$^4$, and R$^4$ is halogen. In yet another embodiment, X is nitrogen, Z is C—R$^4$, and R$^4$ is fluorine.

According to another embodiment of formula I, X is C—R$^4$, R$^4$ is hydrogen, Z is C—R$^4$, and R$^4$ is hydrogen.

In yet another embodiment of formula I, X is C—R$^4$, R$^4$ is halogen, Z is C—R$^4$, and R$^4$ is hydrogen. In yet another embodiment of formula I, X is C—R$^4$, R$^4$ is fluorine, Z is C—R$^4$, and R$^4$ is hydrogen.

In another embodiment of formula I, X is C—R$^4$, R$^4$ is hydrogen, Z is C—R$^4$, and R$^4$ is halogen. In another embodiment of formula I, X is C—R$^4$, R$^4$ is hydrogen, Z is C—R$^4$, and R$^4$ is fluorine.

According to another embodiment of formula I, R$^1$ is R$^Y$.

According to another embodiment of formula I, R$^Y$ is selected from —R$^K$, halogen, —CN, —OR', —N(R')$_2$, —NR'CON(R')$_2$, —NR'CO$_2$R', —CO$_2$R', or —CON(R')$_2$.

According to another embodiment of formula I, R$^K$ is selected from hydrogen, C$_{1-6}$ aliphatic, C$_{3-10}$ cycloaliphatic, or a 3-8-membered saturated monocyclic ring having 0-3 heteroatoms independently selected from nitrogen, oxygen, or sulfur, or an 8-12 membered saturated bicyclic ring system having 0-5 heteroatoms independently selected from nitrogen, oxygen, or sulfur.

According to another embodiment of formula I, R$^1$ is R$^Y$ and R$^Y$ is selected from:

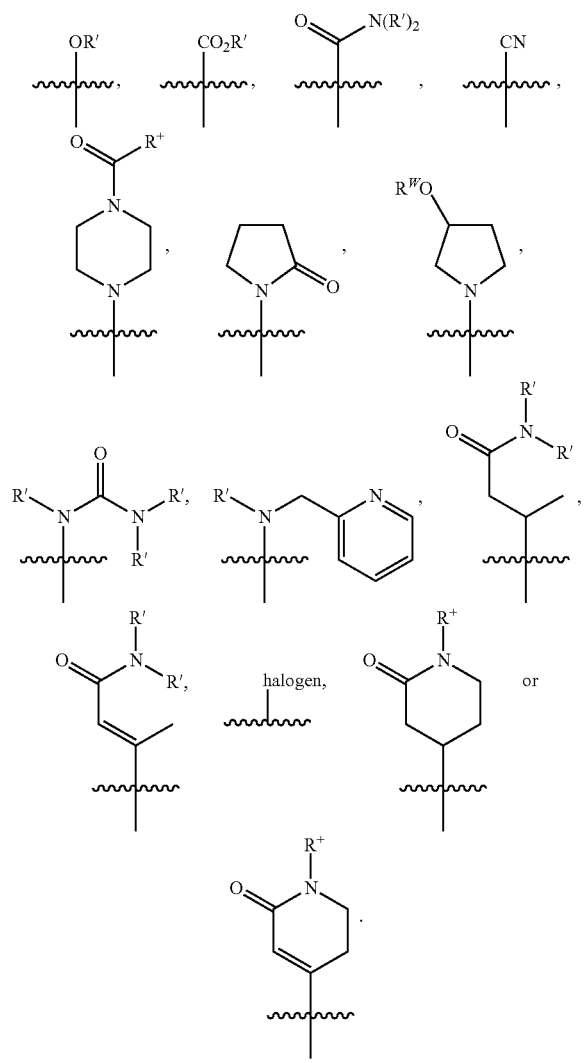

According to another embodiment of formula I, R$^1$ is R$^Y$ and R$^Y$ is selected from:

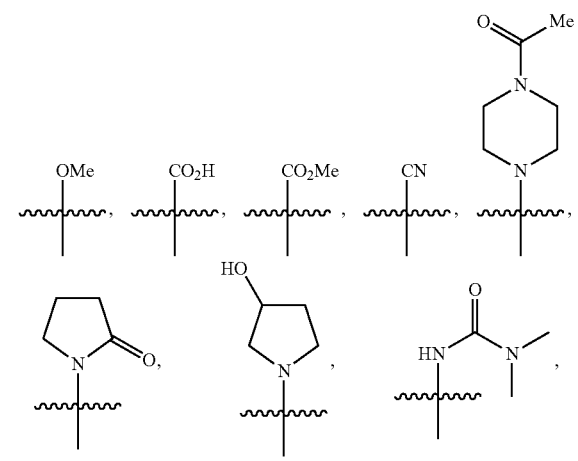

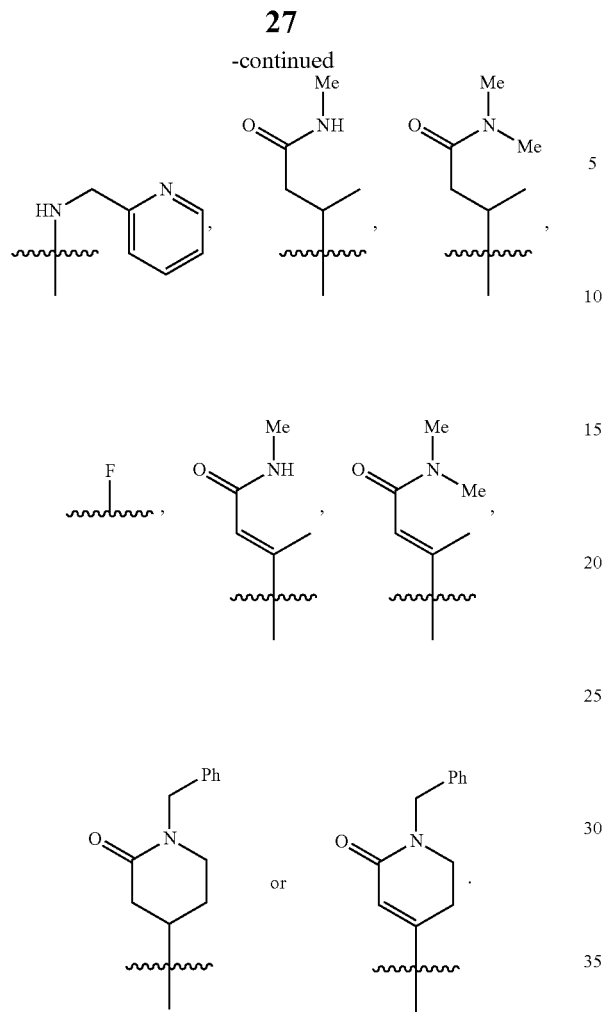

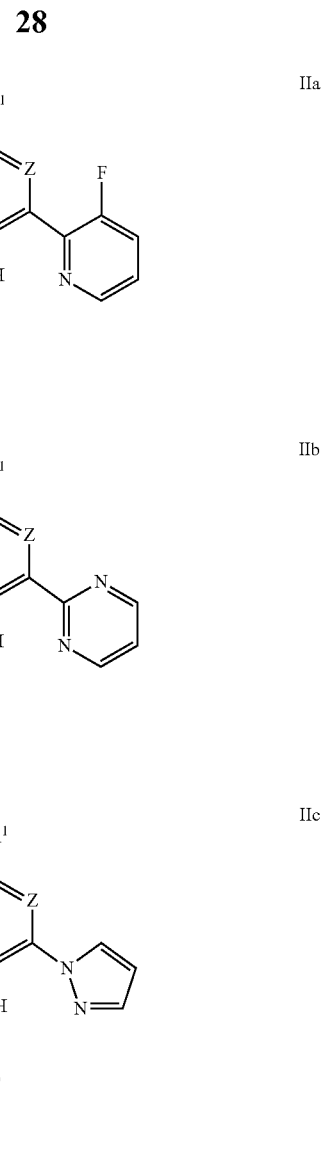

According to another embodiment of formula I, X is C—$R^4$; Z is C—$R^4$; $R^1$ is $R^Y$; $R^3$ is $Ar^2$; and $R^2$ is $C_{1-4}$ aliphatic.

According to another embodiment of formula I, X is C—$R^4$ and $R^4$ is hydrogen; Z is C—$R^4$ and $R^4$ is hydrogen or halogen; $R^1$ is $R^Y$ and $R^Y$ is selected from —$R^K$, halogen, —CN, —OR', —N(R')$_2$, —NR'CON(R')$_2$, —NR'CO$_2$R', —CO$_2$R', or —CON(R')$_2$, wherein R' is hydrogen or $C_{1-6}$ aliphatic; $R^3$ is $Ar^2$ and $Ar^2$ is an optionally substituted heterocyclic ring having 1-2-nitrogen atoms; wherein one of said nitrogen atoms is in the position adjacent to the point of attachment to Ring A; and $R^2$ is $C_{1-3}$ aliphatic.

According to another embodiment of formula I, X is C—$R^4$ and $R^4$ is hydrogen; Z is C—$R^4$ and $R^4$ is hydrogen or halogen, wherein said halogen is fluorine; $R^1$ is $R^Y$ and $R^Y$ is selected from —$R^K$, halogen, —CN, —OR', —N(R')$_2$, —NR'CON(R')$_2$, —NR'CO$_2$R', —CO$_2$R', or —CON(R')$_2$, wherein R' is hydrogen or $C_{1-6}$ aliphatic, and wherein said halogen is fluorine; $R^3$ is $Ar^2$ and $Ar^2$ is an optionally substituted pyridine, pyrimidine or pyrazole ring wherein said optional substituents are fluorine; and $R^2$ is ethyl.

According to another embodiment of formula I, the compounds of the present invention are of formula IIa, IIb, or IIc:

or a pharmaceutically acceptable salt thereof.

According to one embodiment of compounds of formula IIa, IIb, or IIc, Z is C—$R^4$.

According to another embodiment of compounds of formula IIa, IIb, or IIc, Z is C—$R^4$ and $R^4$ is hydrogen. In yet another embodiment, $R^4$ is halogen. In another embodiment, $R^4$ is fluorine.

According to one embodiment of compounds of formula IIa, IIb, or IIc, Z is nitrogen.

According to another embodiment of compounds of formula IIa, IIb, or IIc, $R^2$ is selected from methyl, ethyl, isopropyl, or cyclopropyl. In another embodiment, $R^2$ is ethyl.

According to another embodiment of compounds of formula IIa, IIb, or IIc, $R^1$ is $R^Y$ and $R^Y$ is selected from:

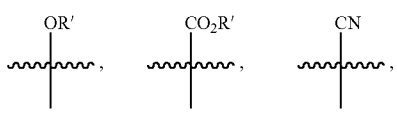

-continued
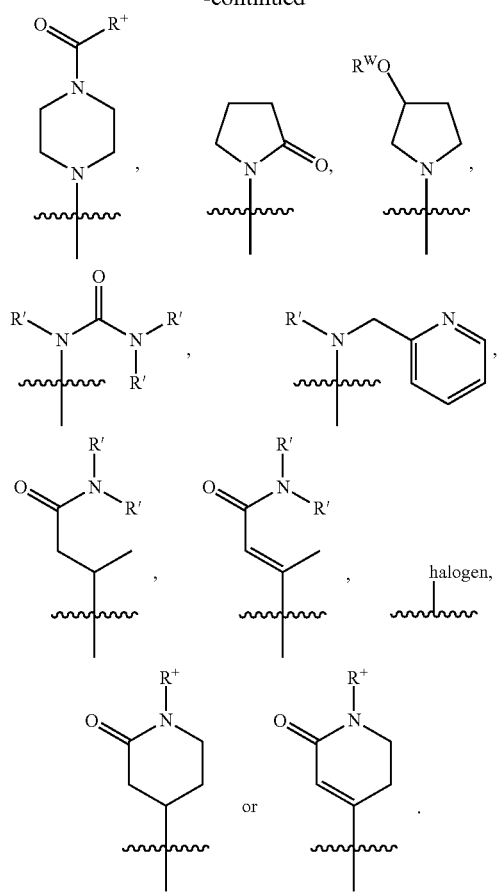
According to another embodiment of compounds of formula IIa, IIb, or IIc, $R^1$ is $R^Y$ and $R^Y$ is selected from:
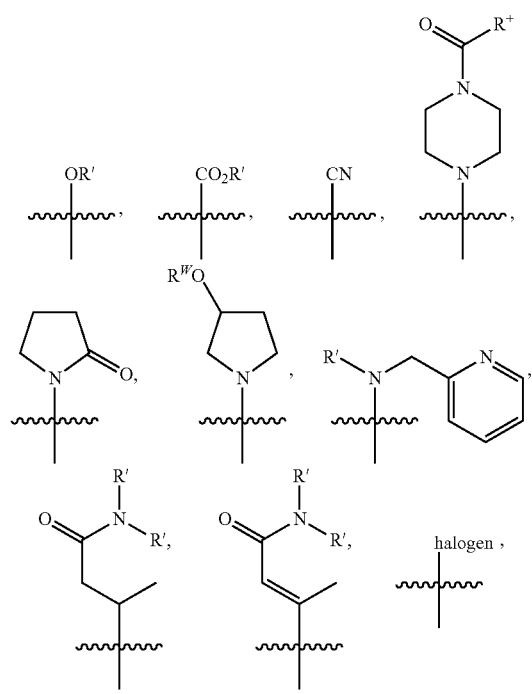
-continued
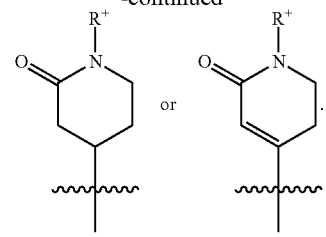
According to another embodiment of compounds of formula IIa, IIb, or IIc, $R^1$ is $R^Y$ and $R^Y$ is selected from:
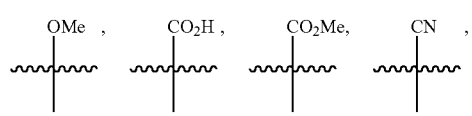
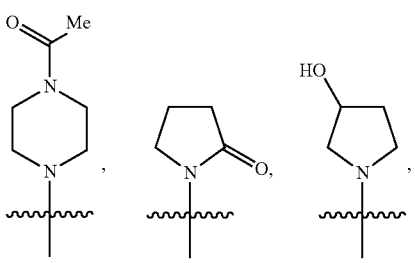
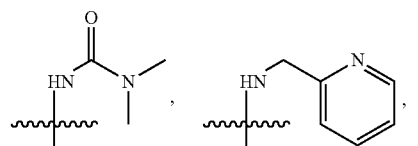
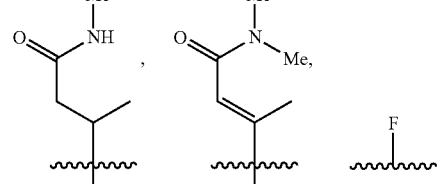
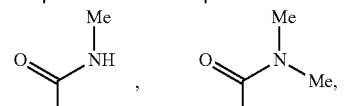
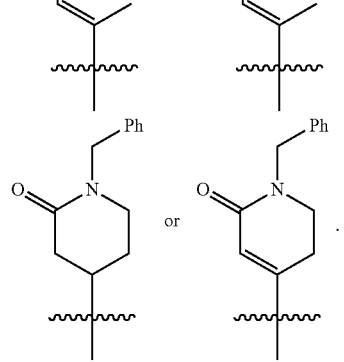

According to another embodiment of compounds of formula IIa, IIb, or IIc, $R^1$ is $R^Y$ and $R^Y$ is selected from:
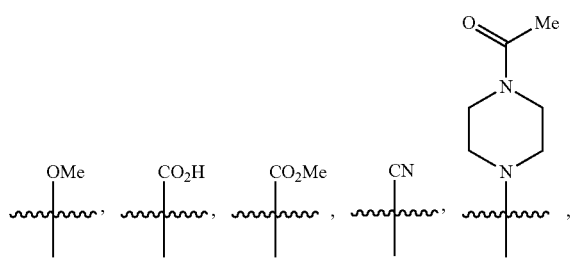
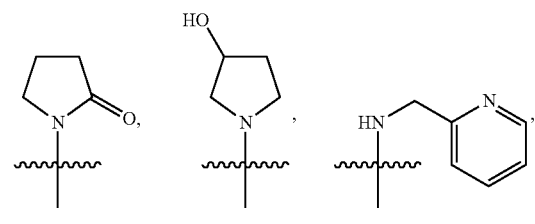
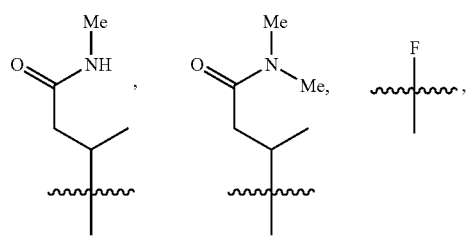
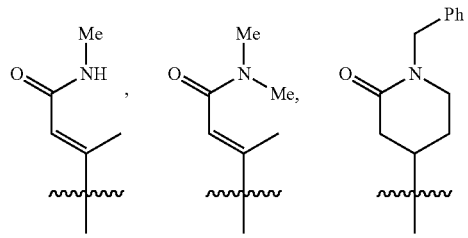
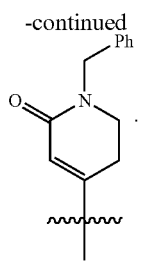
Exemplary structures of formula I are set forth in Table 2 below.
TABLE 2
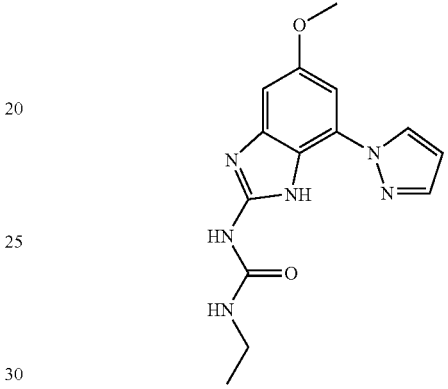
I-1
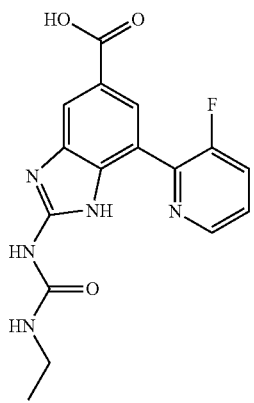 [SMILES: CCNC(=O)Nc1nc2cc(C(=O)O)cc(-c3ncccc3F)c2[nH]1]
I-2
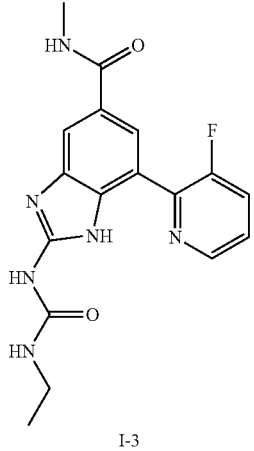
I-3

TABLE 2-continued
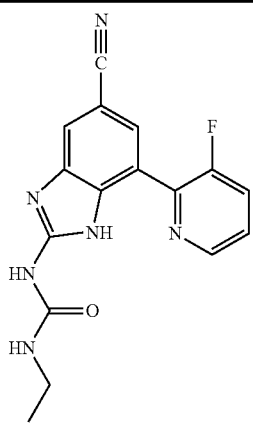
I-4
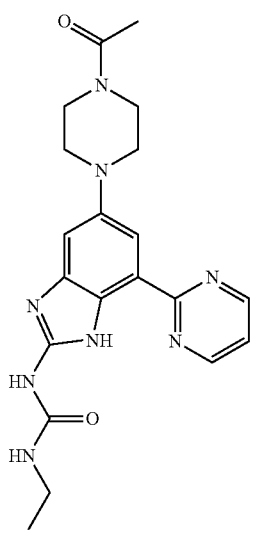 [SMILES: CCNC(=O)Nc1nc2cc(N3CCN(C(C)=O)CC3)cc(-c3ncccn3)c2[nH]1]
I-5
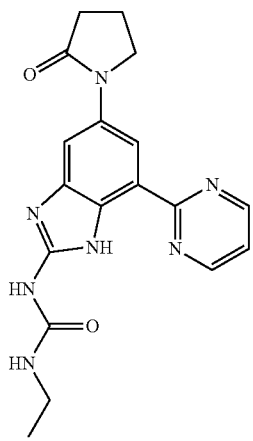 [SMILES: CCNC(=O)Nc1nc2cc(N3CCCC3=O)cc(-c3ncccn3)c2[nH]1]
I-6
TABLE 2-continued
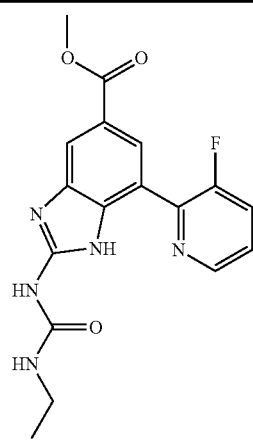
I-7
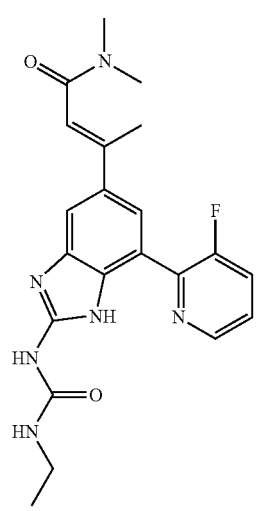 [SMILES: CCNC(=O)Nc1nc2cc(/C(C)=C/C(=O)N(C)C)cc(-c3ncccc3F)c2[nH]1]
I-8
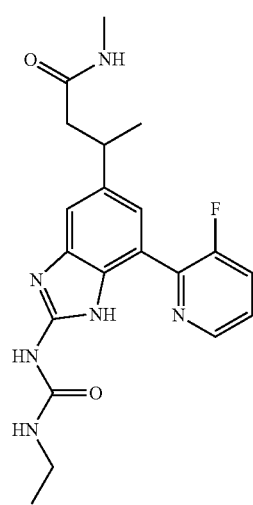 [SMILES: CCNC(=O)Nc1nc2cc(C(C)CC(=O)NC)cc(-c3ncccc3F)c2[nH]1]
I-9

TABLE 2-continued
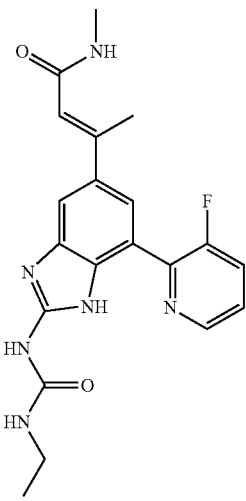 [SMILES: CCNC(=O)Nc1nc2cc(/C(C)=C/C(=O)NC)cc(-c3ncccc3F)c2[nH]1]
I-10
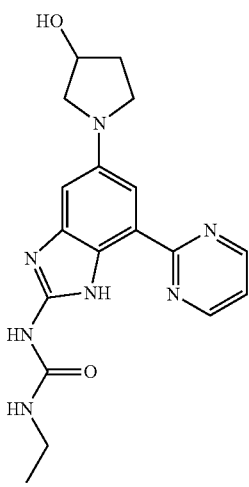 [SMILES: CCNC(=O)Nc1nc2cc(N3CCC(O)C3)cc(-c3ncccn3)c2[nH]1]
I-12
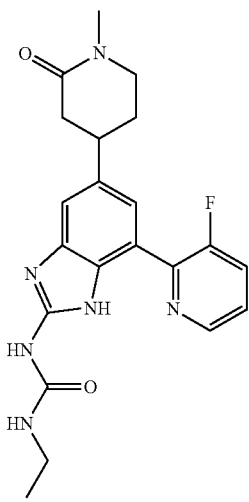 [SMILES: CCNC(=O)Nc1nc2cc(C3CCN(C)C(=O)C3)cc(-c3ncccc3F)c2[nH]1]
I-13
TABLE 2-continued
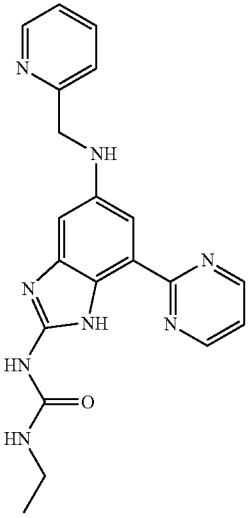 [SMILES: CCNC(=O)Nc1nc2cc(NCc3ccccn3)cc(-c3ncccn3)c2[nH]1]
I-14
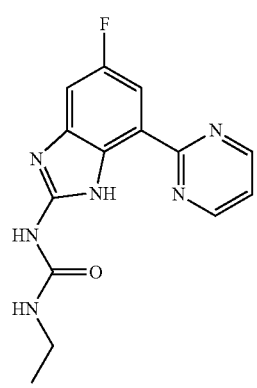 [SMILES: CCNC(=O)Nc1nc2cc(F)cc(-c3ncccn3)c2[nH]1]
I-15
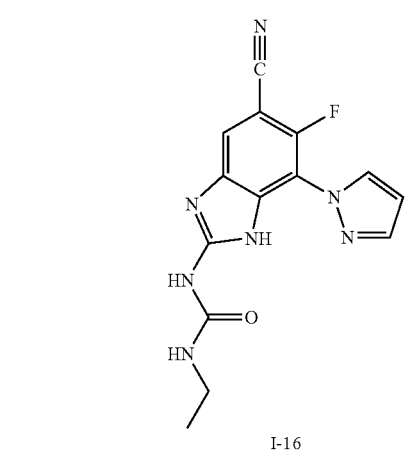
I-16

TABLE 2-continued
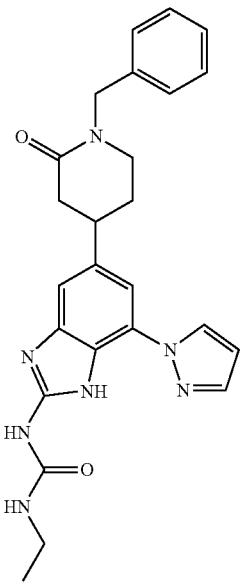 [SMILES: CCNC(=O)Nc1nc2cc(C3CCN(Cc4ccccc4)C(=O)C3)cc(-n3cccn3)c2[nH]1]
I-17
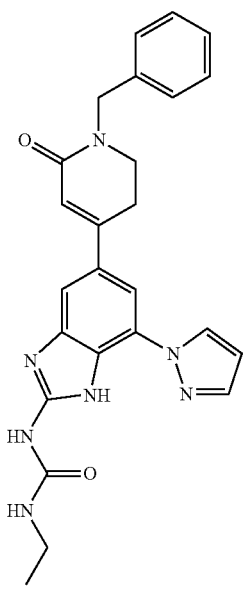 [SMILES: CCNC(=O)Nc1nc2cc(C3=CC(=O)N(Cc4ccccc4)CC3)cc(-n3cccn3)c2[nH]1]
I-18 or
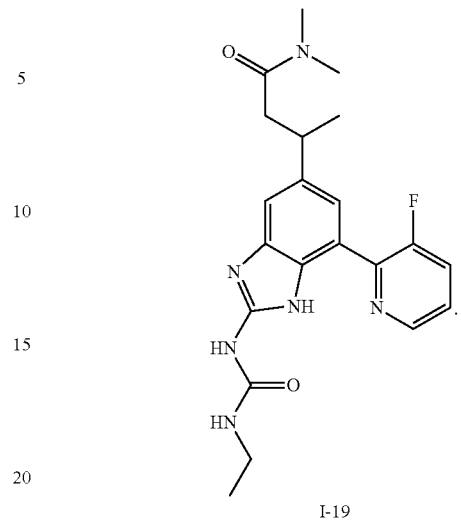
I-19
In another embodiment, the following structures correspond to the named provisos: 1-ethyl-3-(5-(2,3-dihydro-1-isopropyl-2-oxo-1H-imidazol-4-yl)-7-(pyrimidin-2-yl)-1H-benzo[d]imidazol-2-yl)urea:
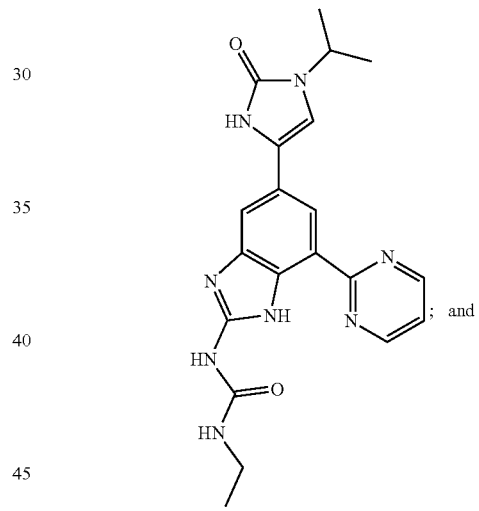
; and
1-ethyl-3-(5-(1,1-dimethylurea)-7-(pyrimidin-2-yl)-1H-benzo[d]imidazol-2-yl)urea:
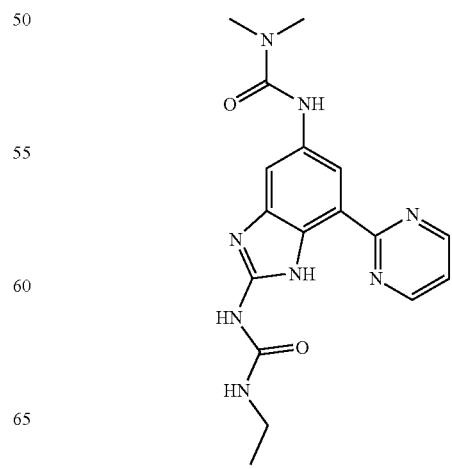

The following definitions describe terms and abbreviations used herein in the schemes and examples:

Ac acetyl
Bu butyl
Et ethyl
Ph phenyl
Me methyl
EtOAc ethyl acetate
Boc t-butyloxycarbonyl
dppf 1,1'-bis(diphenylphosphino)-ferrocene
DME 1,2-dimethoxyethane
EDC 1-(3-dimethylaminopropyl)-3-ethylcarbodiimide hydrochloride
4-DMAP 4-dimethylaminopyridine
DIPEA diisopropylethylamine
DIEA diisopropylethylamine
THF tetrahydrofuran
DMF N,N-dimethylformamide
DMSO dimethyl sulfoxide
HOAc acetic acid
TFA trifluoroacetic acid
TFAA trifluoroacetic anhydride
NMP N-methylpyrrolidinone
HOBT hydroxybenzotriazole
DCM dichloromethane
HBTU O-benzotriazol-1-yl-N,N,N',N'-tetramethyluronium hexafluorophosphate
$K_2CO_3$ potassium carbonate
$Na_2CO_3$ sodium carbonate
$Li_2CO_3$ lithium carbonate
$Cs_2CO_3$ cesium carbonate
$NaHCO_3$ sodium bicarbonate
NaOH sodium hydroxide
KOH potassium hydroxide
LiOH lithium hydroxide
atm atmospheres
rt or RT room temperature The compounds of this invention may be prepared in general by methods known to those skilled in the art for analogous compounds, as illustrated by the general Schemes 1-23 shown below and the Examples set forth infra.

Scheme 1:

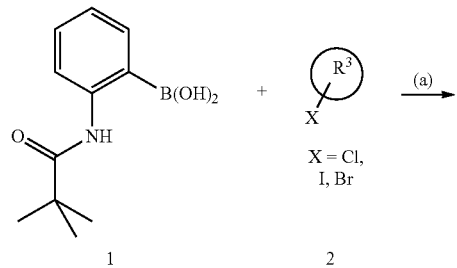

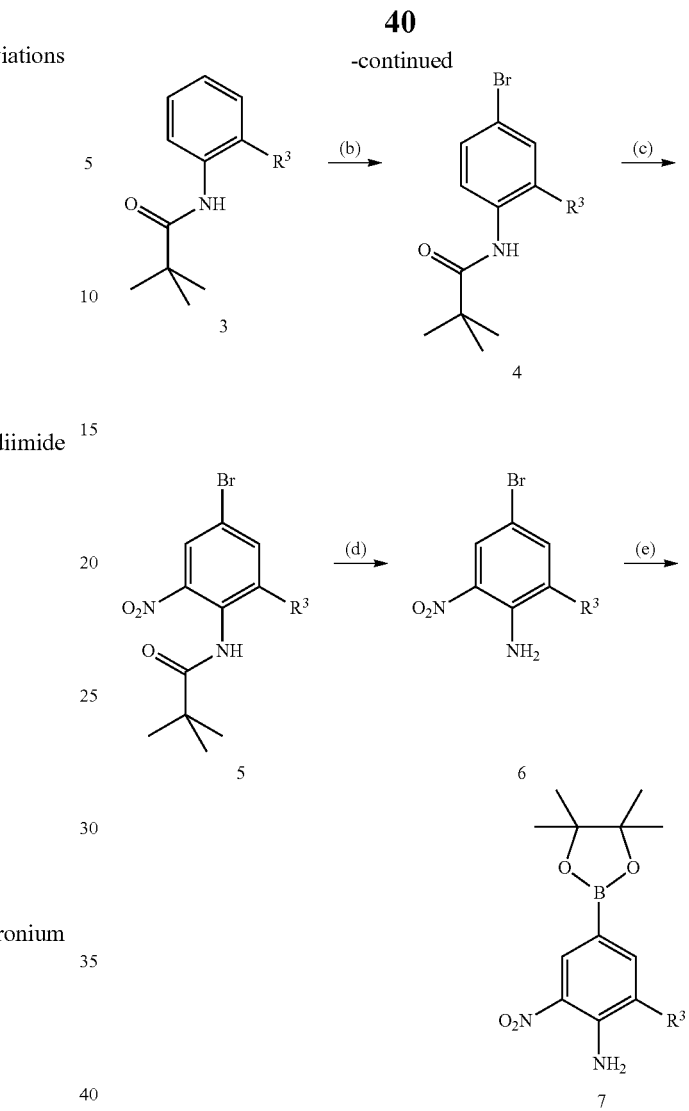

Reagents and conditions: (a) $Pd(PPh_3)_4$, $NaHCO_3$, $H_2O$, DME, Δ; (b) bromine, HOAc; (c) $HNO_3$, TFA, TFAA; (d) conc. HCl; (e) bis(pinocolato)diboron, $Pd(PPh_3)_4$, KOAc, dioxane, Δ.

Scheme 1 above shows a general method for preparing intermediate 7 useful for the further preparation of compounds of the present invention wherein $R^3$ is $Ar^2$. Compound 1 (purchased commercially from CB Research) underwent Suzuki-type coupling with commercial aryl halides (purchased from Aldrich or Manchester Organics Limited) of type 2 to form biaryl intermediate 3. Compound 3 was brominated with bromine in acetic acid to form bromide 4, then nitrated with nitric acid in the presence of trifluoroacetic acid and trifluoroacetic anhydride to form nitro intermediate 5. Acidic hydrolysis of compound 5 provided nitro aniline 6. The bromo group of compound 6 was converted into boronate ester 7 using bis(pinocolato)diboron in the presence of $Pd(PPh_3)_4$ in buffered dioxane (see, e.g., Kiyomori, A.; Marcoux, J.-F.; Buchwald, S. L., *Tetrahedron Letters, vol.* 40, (1999) 2657-2660.). Compounds 6 and 7 were further elaborated in the schemes herein below to form compounds of the present invention wherein $R^3$ is $Ar^2$.

Scheme 2:

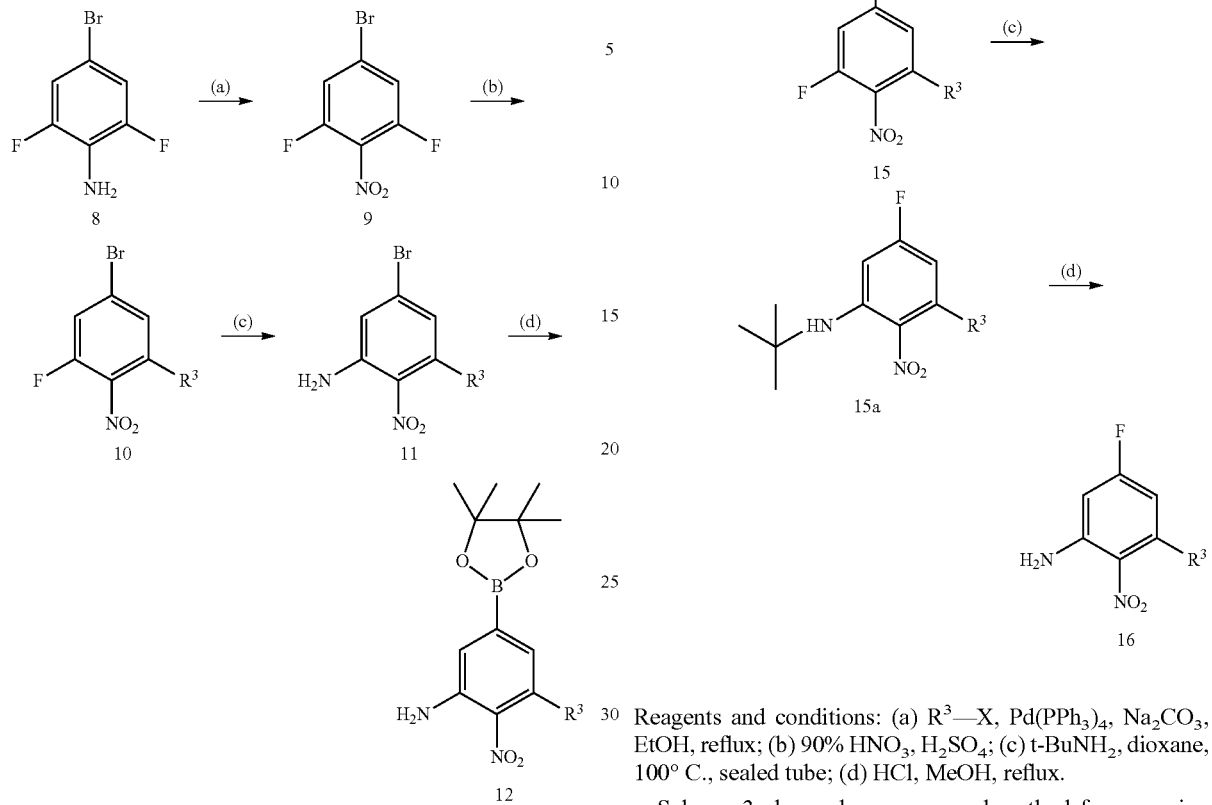

Reagents and conditions: (a) NaBO₃ monohydrate, HOAc, 55° C.; (b) R³, NaH, THF; (c) NH₃, MeOH, 50° C.; (d) bis(pinocolato)diboron, Pd(PPh₃)₄ or Pd(dppf)₂Cl₂, KOAc, dioxane, Δ.

Scheme 2 above shows a general method for preparing intermediate 12 useful for the further preparation of compounds of the present invention wherein R³ is Ar² and Ar² is a 5 or 6 membered nitrogen containing heteroaryl ring wherein one of said heteroaryl ring nitrogens is directly linked to ring A (e.g., pyrazole, imidazole, etc.). Commercially available aniline 8 was oxidized to give nitro intermediate 9. Ring R³ was introduced by anionic displacement of aryl fluoride 9 to give biaryl fluoride 10. The remaining fluoro group in compound 10 was displaced with ammonia in methanol by heating in a sealed tube to give aniline 11. Finally, the bromo group of compound II was converted into boronate ester 12 using bis(pinocolato)diboron in the presence of Pd(PPh₃)₄ in hot buffered dioxane.

Scheme 3:

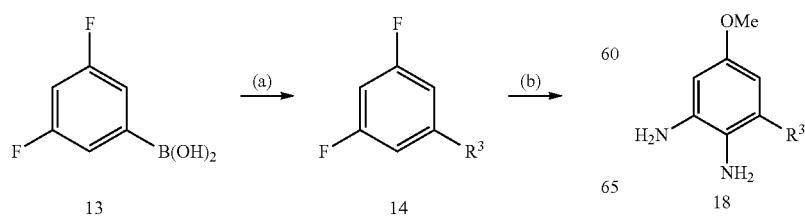

Reagents and conditions: (a) R³—X, Pd(PPh₃)₄, Na₂CO₃, EtOH, reflux; (b) 90% HNO₃, H₂SO₄; (c) t-BuNH₂, dioxane, 100° C., sealed tube; (d) HCl, MeOH, reflux.

Scheme 3 above shows a general method for preparing intermediate 16. Commercially available difluoroboronic acid 13 underwent Suzuki-type coupling with R³ halide to give biaryl difluoro analog 14. Compound 14 was nitrated with 90% nitric acid in sulfuric acid to give the difluoro nitro analog 15. Ammonia displacement of aryl fluoride 15 in a sealed tube gave t-butylamine 15a. Deprotection of the t-butyl group in 15a under acidic conditions gave aniline 16. Intermediate aniline 16 was further homologated in the schemes described herein below to give additional compounds of the present invention.

Scheme 4:

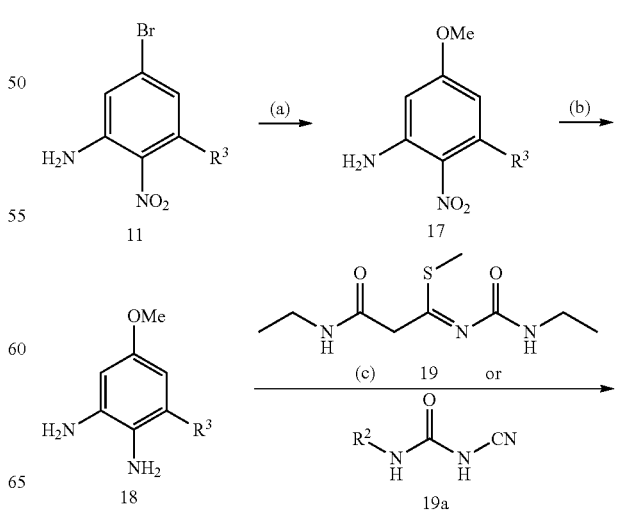

-continued

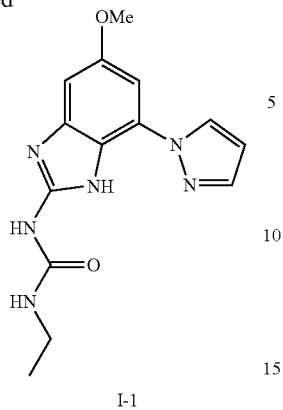

I-1

Reagents and conditions: (a) NaOMe, MeOH, DMSO, microwave, 170° C.; (b) H$_2$, Pd/C, EtOAc; (c) 19, H$_2$O, pH 3.5, dioxane, Δ.

Scheme 4 above shows a method for preparing compound I-1 wherein R$^3$ is an N-linked pyrazole. The bromo group in Compound II was displaced with sodium methoxide in methanol to give the methoxy analog 17. Reduction of the nitro group in compound 17 with 10% palladium on carbon in EtOAc under an H$_2$ atmosphere afforded diamine 18. Treatment of diamine 18 with N,N-diethylureamido-2-methyl-thiopseudourea 19 (prepared according to the method described in Example 12 below) or N'-alkyl-N-cyanourea 19a (prepared according to the method described in Example 13 below) in hot buffered water afforded compound I-1. Scheme IV is also useful for preparing other compounds of the present invention wherein R$^3$ is an Ar$^2$ group that may be introduced by direct anionic displacement of an aryl fluoride and wherein R$^1$ is R$^Y$ and R$^Y$ is selected from OR', SR', or N(R')$_2$.

Scheme 5:

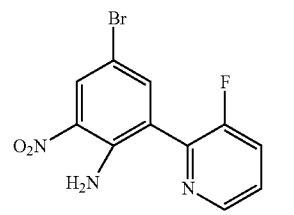

20

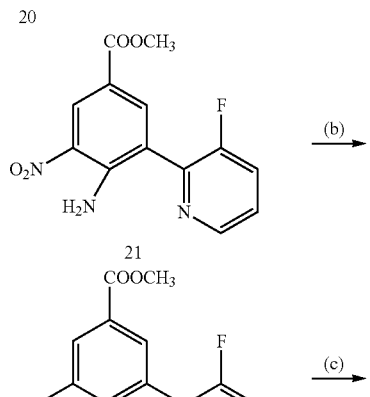

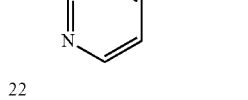

22

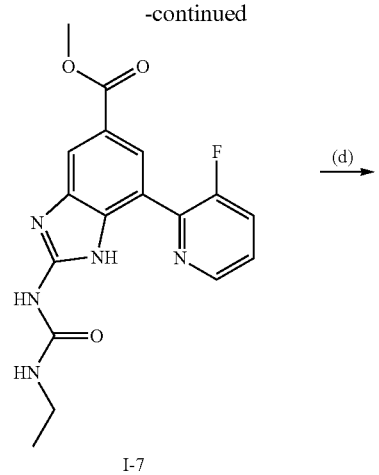

Reagents and conditions: (a) CO, Pd(PPh$_3$)$_4$, MeOH, 100° C., 12 hours; (b) H$_2$, Pd/C, MeOH, 20 hours; (c) 19, dioxane/water, pH 3.5, 100° C., 2 hours; (d) 6N HCl, 100° C., 1.5 hours.

Scheme 5 above shows a method for preparing compounds I-7 and I-2 wherein R$^3$ is a 2-fluoropyridine group and R$^1$ is R$^Y$ and R$^Y$ is CO$_2$R'. Starting intermediate 20 was prepared according to the route described in Scheme 2. The bromo group in compound 20 was carbonylated under Suzuki palladium cross coupling conditions in a sealed tube in hot methanol to give the methyl ester analog 21. Reduction of the nitro group in compound 21 with 10% palladium on carbon in methanol under an H$_2$ atmosphere afforded diamine 22. Treatment of diamine 18 with N,N-diethylureamido-2-methyl-thiopseudourea 19 in hot dioxane with buffered water afforded compound I-7. Acidic hydrolysis of I-7 at 100° C. afforded free acid I-2. Scheme 5 is also useful for preparing other compounds of the present invention wherein R$^3$ is another Ar$^2$ group and wherein R$^1$ is R$^Y$ and R$^Y$ is CO$_2$R'.

Scheme 6:

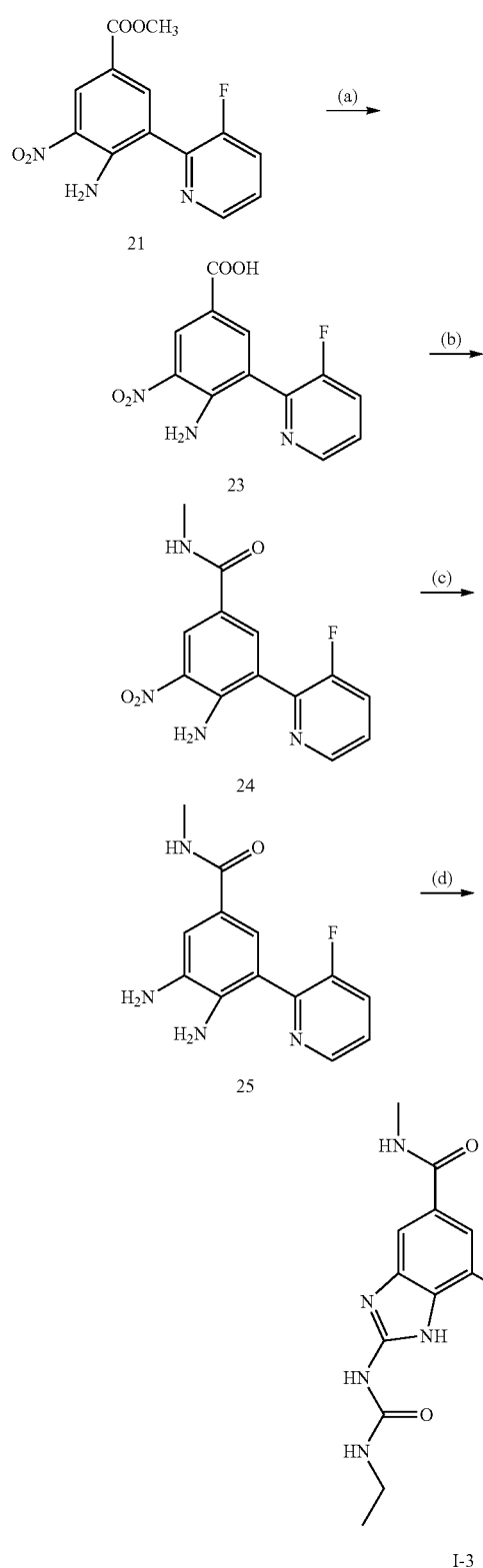

Reagents and conditions: (a) NaOH, H₂O/MeOH, reflux, 1 hr; (b) 2.0M CH₃NH₂ in THF, BOP reagent, DMF, sealed tube; (c) H₂, Pd/C, MeOH, 12 hours; (d) 19, dioxane/water, pH 3.5, 100° C., 2 hours.

Scheme 6 above shows a method for preparing compound I-3 wherein $R^3$ is a 2-fluoropyridine group and $R^1$ is $R^Y$ and $R^Y$ is CON(R')₂. Starting intermediate 21 was prepared according to the route described in Scheme 5. Basic hydrolysis of compound 21 yielded free acid 23 which was subsequently coupled with methylamine in THF (2.0M soln) using BOP reagent (benzotriazol-1-yloxy-tris(dimethylamino)-phosphonium hexafluorophosphate, Aldrich) in a sealed tube to afford amide analog 24. Reduction of the nitro group in compound 24 with 10% palladium on carbon in methanol under an H₂ atmosphere afforded diamine 25. Treatment of diamine 25 with N,N-diethylureamido-2-methyl-thiopseudourea 19 in hot dioxane with buffered water afforded compound I-3. Scheme 6 is also useful for preparing other compounds of the present invention wherein $R^3$ is another $Ar^2$ group and wherein $R^1$ is $R^Y$ and $R^Y$ is CON(R')₂.

Scheme 7:

-continued

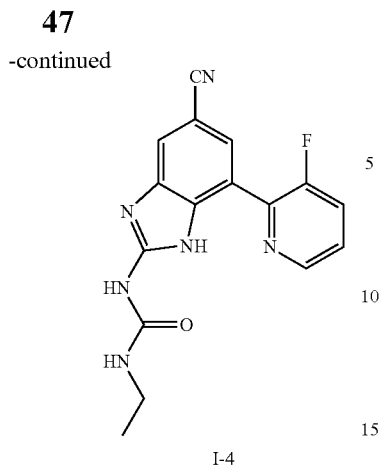

I-4

Reagents and conditions: (a) NH₂OH—HCl salt, Et₃N, DMF, BOP; (b) PBr₃, benzene, 100° C. 30 minutes; (c) H₂, Pd/C, MeOH, 10 minutes; (d) 19, dioxane/water, pH 3.5, 100° C., 2 hours.

Scheme 7 above shows a method for preparing compound I-4 wherein $R^3$ is a 2-fluoropyridine group and $R^1$ is $R^Y$ and $R^Y$ is CN. Starting intermediate acid 23 was prepared according to the route described in Scheme 6. Conversion of acid 23 to hydroxyamide 24 was accomplished with ammonium hydroxide with BOP reagent in DMF. Subsequent dehydration of hydroxyamide 24 with PBr₃ in refluxing benzene afforded nitrile 27. Reduction of the nitro group in compound 27 with 10% palladium on carbon in methanol under an H₂ atmosphere for 10 minutes afforded diamine 28. Treatment of diamine 28 with N,N-diethylureamido-2-methyl-thiopseudourea 19 in hot dioxane with buffered water afforded compound I-4.

Scheme 8:

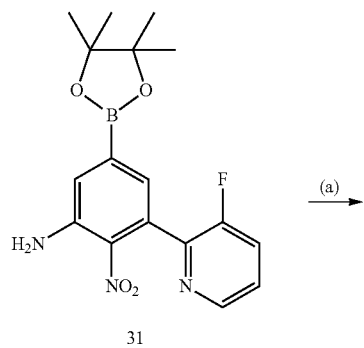

Reagents and conditions: (a) N-phenyltrifluoromethanesulfonimide, Et₃N, DMF, 16 hours, RT.

Scheme 8 above shows a method for preparing pyridone triflate 30 used in Scheme 9 below for the preparation of compound I-13.

Scheme 9:

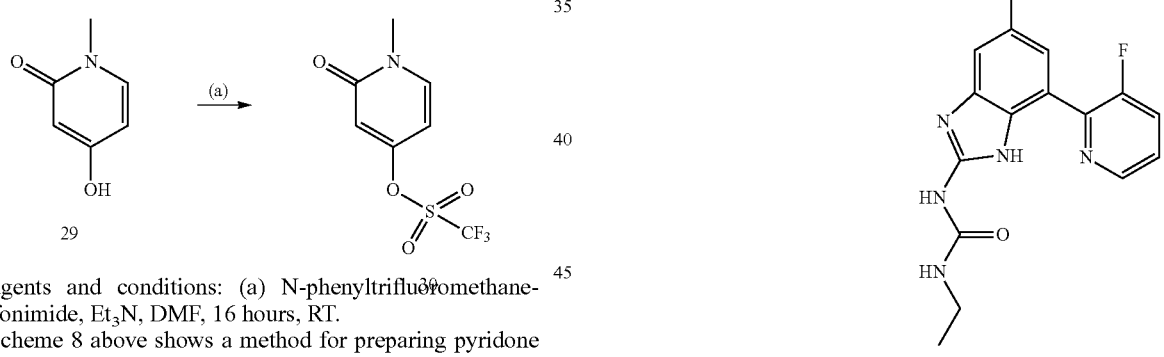

I-13

Reagents and conditions: (a) 30, Pd(PPh₃)₄, Na₂CO₃, LiCl, DMF, 95° C., 4 hours; (b) H₂ (45 psi), 10% Pd/C, (1:3) MeOH/EtOAc, 1 hour; (c) 19, dioxane/water, pH 3.5, 100° C., 4 hours.

Scheme 9 above shows a method for preparing compound I-13 wherein $R^3$ is a 2-fluoropyridine group and $R^1$ is an N-methyl piperidone. Starting boronate 31 was prepared according to the route described in Scheme 3. Coupling of the boronate 31 with pyridone triflate 30 (prepared according to the procedure listed in Scheme 8) was accomplished using Suzuki-type cross coupling conditions to give compound 32. Subsequent reduction of the nitro group with concomitant reduction of the pyridinone under hydrogenation conditions afforded diamine compound 33. Treatment of diamine 33 with N,N-diethylureamido-2-methyl-thiopseudourea 19 in hot dioxane with buffered water afforded compound I-13.

Scheme 10:
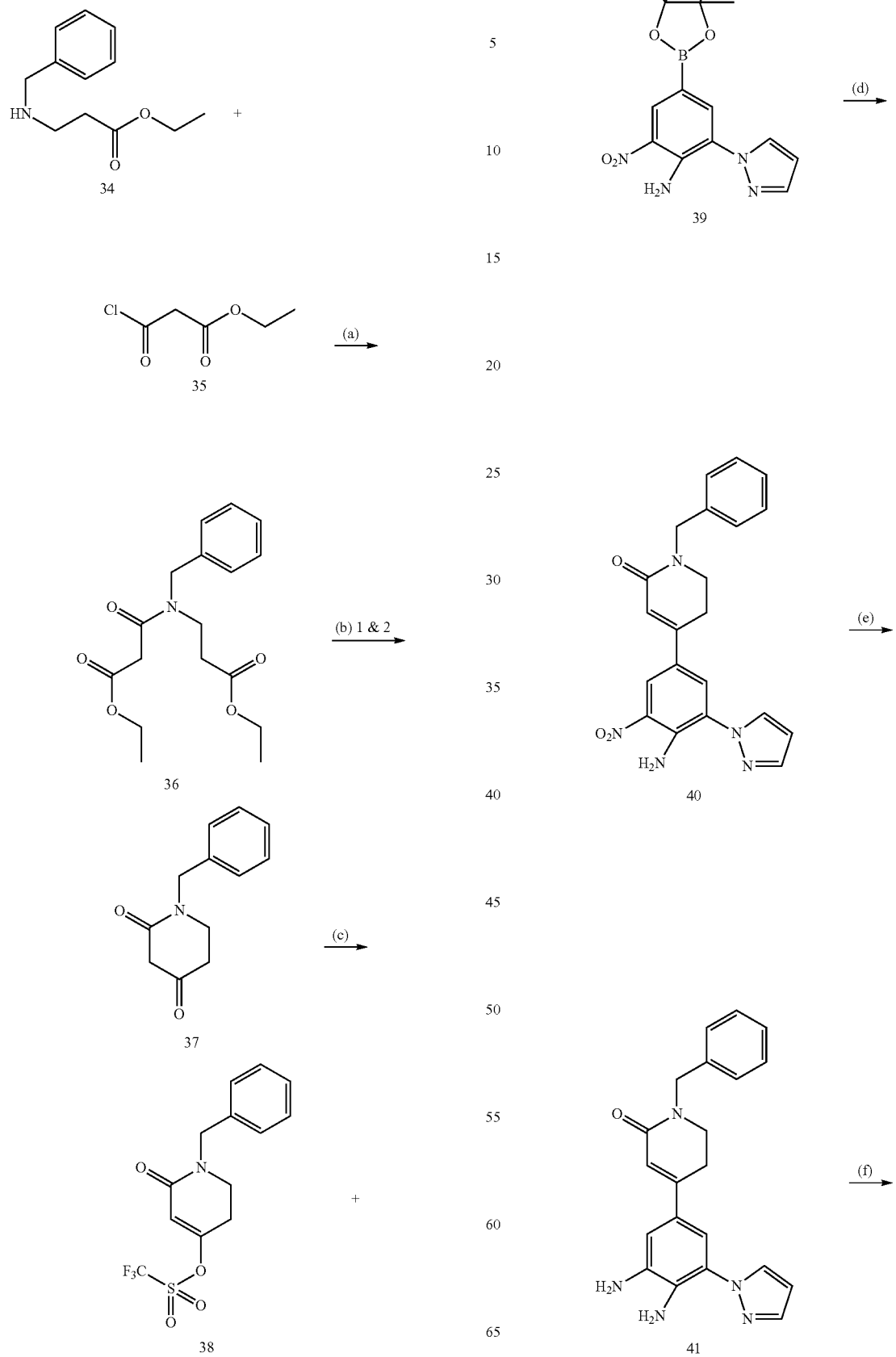

-continued

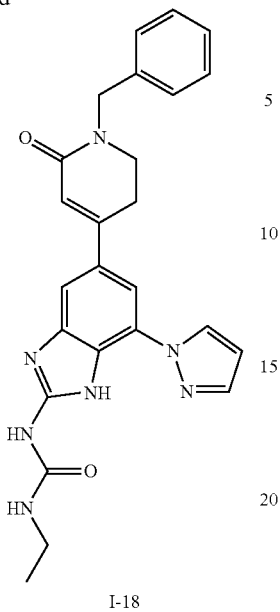

I-18

Reagents and conditions: (a) Et₃N, CH₂Cl₂, 0° C.; (b) 1. Na/EtOH, 120° C., 3 hours; 2. HCl/CH₃CN, trace H₂O, 120° C., 4 hours; (c) N-phenyltrifluoromethanesulfonimide, Et₃N, CH₂Cl₂; (d) 39, Pd(PPh₃)₄, 2.0 N Na₂CO₃, LiCl, DME, Δ; (e) H₂ (1 atm), 10% Pd/C, MeOH, 0° C., 5 minutes; (f) 19, dioxane/water, pH 3.5, 100° C., 2 hours.

Scheme 10 above shows a method for preparing compound I-18. Alkylation of benzyl amine analog 34 (purchased from Lancaster) with ethyl malonyl chloride 35 with triethylamine as base in methylene chloride at 0° C. substituted benzyl amine intermediate 36. Cyclization followed by decarboxylation gave N-benzyl piperidine dione 37. Triflate 38 was prepared according to the procedure listed in scheme 8. Coupling of the boronate 39 (prepared according to the procedure listed in scheme 1) with pyridone triflate 38 was accomplished using Suzuki-type cross coupling conditions to give compound 40. Subsequent reduction of the nitro group under cold catalytic hydrogenation conditions afforded diamine compound 41. Treatment of diamine 41 with N,N-diethylureamido-2-methyl-thiopseudourea 19 in hot dioxane with buffered water afforded compound I-18.

Scheme 11:

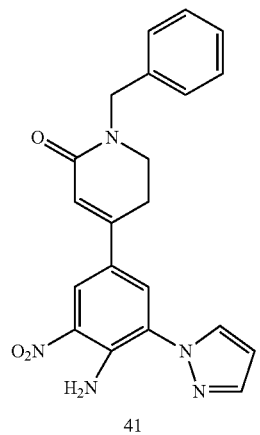

41

-continued

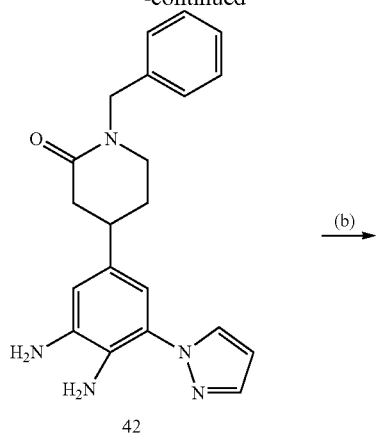

42

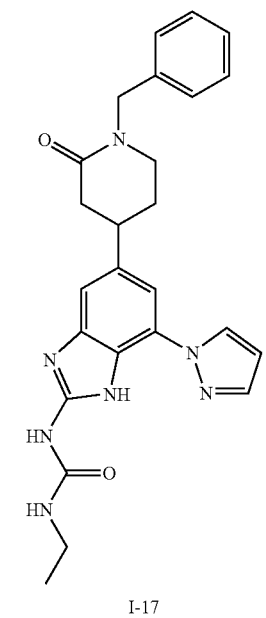

I-17

Reagents and conditions: (a) H₂ (1 atm), 10% Pd/C, MeOH, RT, 12 hours; (b) 19, dioxane/water, pH 3.5, 100° C., 2 hours.

Scheme 11 above shows a method for preparing compound I-17. Reduction of intermediate 41 (prepared according to the method described in scheme 10) led to saturated piperidone diamine 42. Treatment of diamine 42 with N,N-diethylureamido-2-methyl-thiopseudourea 19 in hot dioxane with buffered water afforded compound I-17.

Scheme 12:

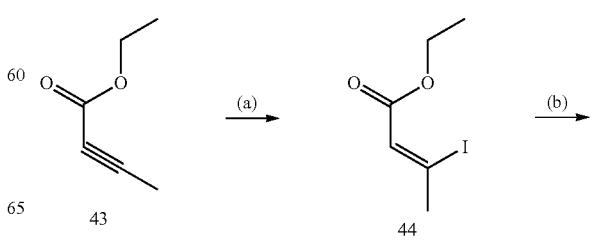

43     44

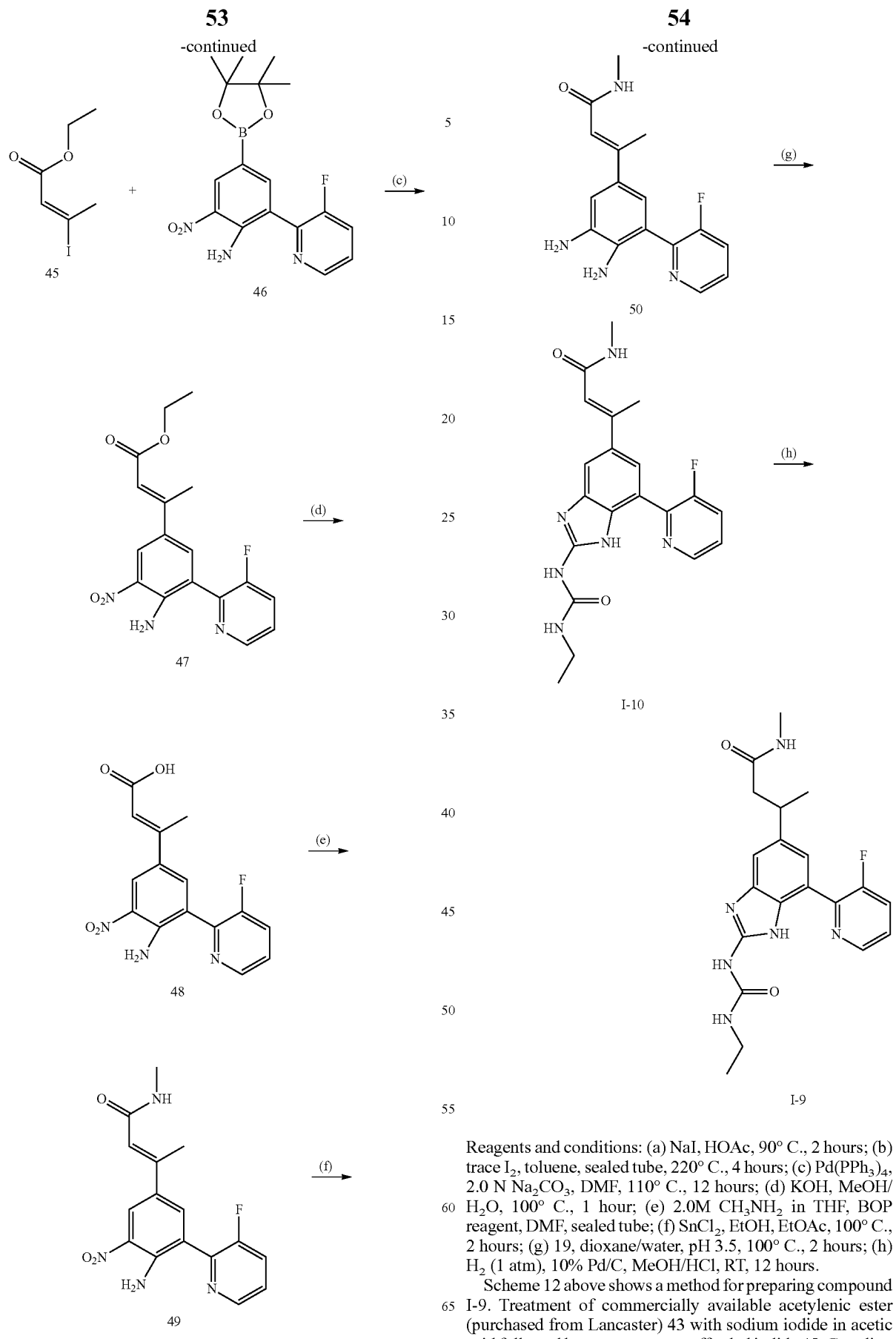

Reagents and conditions: (a) NaI, HOAc, 90° C., 2 hours; (b) trace $I_2$, toluene, sealed tube, 220° C., 4 hours; (c) $Pd(PPh_3)_4$, 2.0 N $Na_2CO_3$, DMF, 110° C., 12 hours; (d) KOH, MeOH/$H_2O$, 100° C., 1 hour; (e) 2.0M $CH_3NH_2$ in THF, BOP reagent, DMF, sealed tube; (f) $SnCl_2$, EtOH, EtOAc, 100° C., 2 hours; (g) 19, dioxane/water, pH 3.5, 100° C., 2 hours; (h) $H_2$ (1 atm), 10% Pd/C, MeOH/HCl, RT, 12 hours.

Scheme 12 above shows a method for preparing compound I-9. Treatment of commercially available acetylenic ester (purchased from Lancaster) 43 with sodium iodide in acetic acid followed by rearrangement afforded iodide 45. Coupling of the boronate 46 (prepared according to the procedure listed in scheme 1) with vinyl iodide 45 under Heck conditions gave compound 47. Basic hydrolysis of the methyl ester in compound 47 yielded free acid 48 which was subsequently coupled with methylamine in THF (2.0M soln) using BOP reagent (benzotriazol-1-yloxy-tris(dimethylamino)-phosphonium hexafluorophosphate, Aldrich) in a sealed tube to afford amide analog 24. Reduction of the nitro group in compound 24 with tin chloride in refluxing ethanol afforded diamine 50. Treatment of diamine 50 with N,N-diethylureamido-2-methyl-thiopseudourea 19 in hot dioxane with buffered water afforded compound I-10. Subsequent reduction of the olefin in compound I-10 under catalytic hydrogenation conditions afforded saturated analog I-9.

Scheme 13:

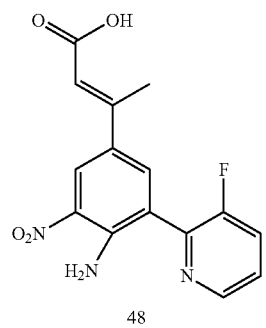

48

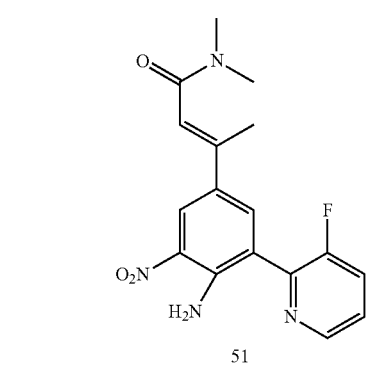

51

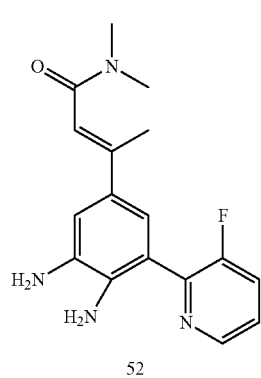

52

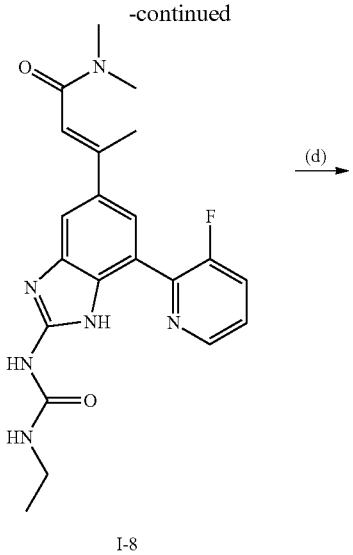

I-8

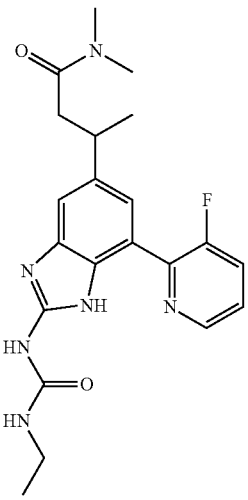

I-19

Reagents and conditions: (a) 2.0M Me$_2$NH in THF, BOP reagent, DMF, sealed tube; (b) SnCl$_2$, EtOH, EtOAc, 100° C., 2 hours; (c) 19, dioxane/water, pH 3.5, 100° C., 2 hours; (d) H$_2$ (1 atm), 10% Pd/C, MeOH/HCl, RT, 12 hours.

Scheme 13 above shows a method for preparing compounds I-8 and I-19. Free acid 48 (prepared according to scheme 12) was coupled with dimethylamine in THF (2.0M soln) using BOP reagent (benzotriazol-1-yloxy-tris(dimethylamino)-phosphonium hexafluorophosphate, Aldrich) in a sealed tube to afford amide analog 51. Reduction of the nitro group in compound 51 with tin chloride in refluxing ethanol afforded diamine 52. Treatment of diamine 52 with N,N-diethylureamido-2-methyl-thiopseudourea 19 in hot dioxane with buffered water afforded compound I-8. Subsequent reduction of the olefin in compound I-8 under catalytic hydrogenation conditions afforded saturated analog I-19.

Scheme 14:

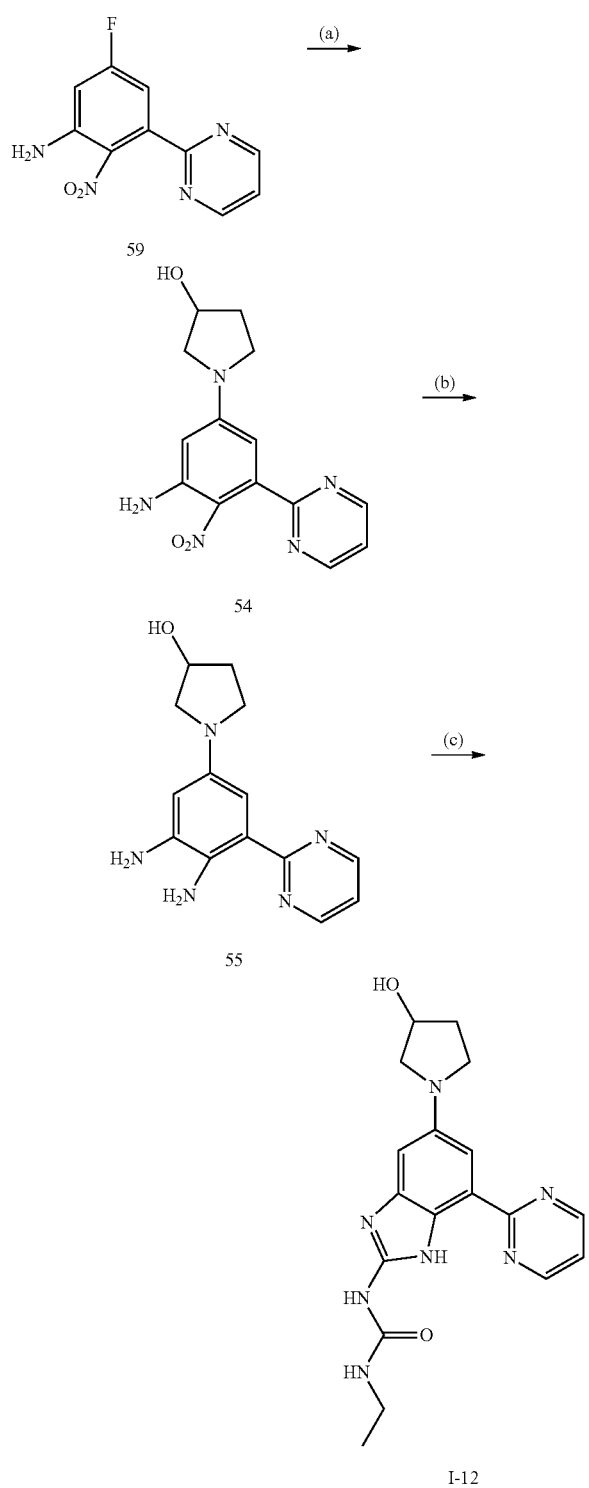

Reagents and conditions: (a) 3-hydroxypyrrolidine, dioxane, 160° C., 1 hour; (b) H$_2$ (45 psi), 10% Pd/C, (1:3) MeOH/EtOAc, RT; (c) 19, dioxane/water, pH 3.5, 100° C., 2 hours.

Scheme 14 above shows a method for preparing compound I-12. Aryl fluoride 59 (prepared according to schemes 3 and 16 using 2-chloropyrimidine to introduce R$^3$) was displaced with 3-hydroxypyrrolidine in refluxing dioxane for 1 hour to give a good yield of intermediate 54. Reduction of the nitro group in compound 54 with Pd/C under 4 atm of H$_2$ afforded diamine 55. Treatment of diamine 55 with N,N-diethylurea-mido-2-methyl-thiopseudourea 19 in hot dioxane with buffered water afforded compound I-12.

Scheme 15:

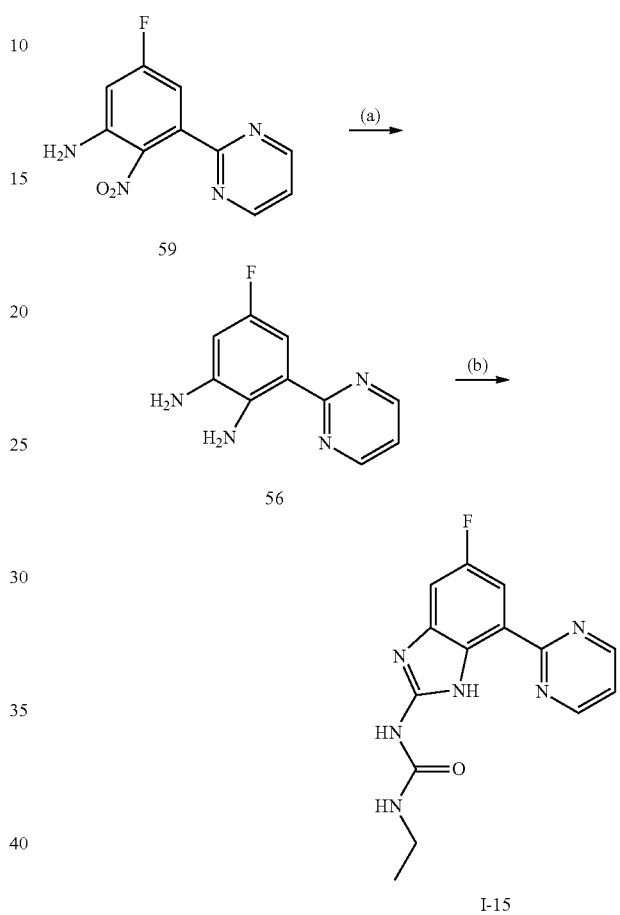

Reagents and conditions: (a) H$_2$ (45 psi), 10% Pd/C, (1:3) MeOH/EtOAc, RT; (c) 19, dioxane/water, pH 3.5, 100° C., 2 hours.

Scheme 15 above shows a method for preparing compound I-15. The nitro group of aryl fluoride 59 (prepared according to schemes 3 and 16 using 2-chloropyrimidine to introduce R$^3$) was reduced with Pd/C under 4 atm of H$_2$ to afford diamine 56. Treatment of diamine 56 with N,N-diethylurea-mido-2-methyl-thiopseudourea 19 in hot dioxane with buffered water afforded compound I-15.

Scheme 16:

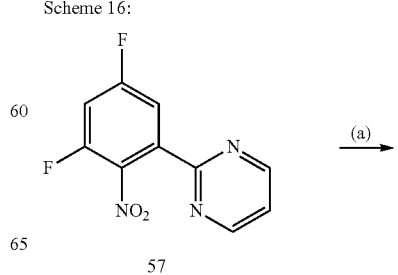

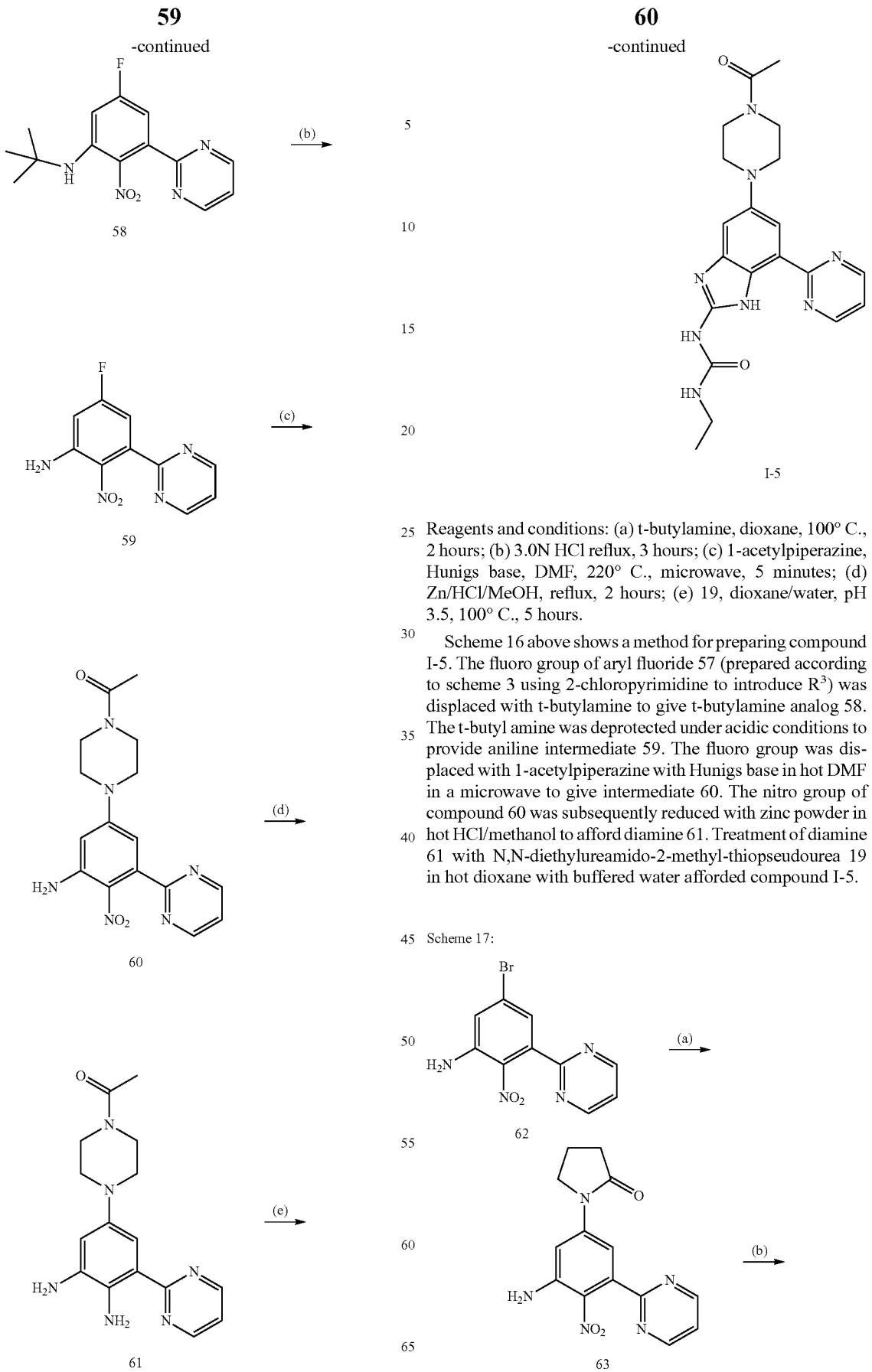

Reagents and conditions: (a) t-butylamine, dioxane, 100° C., 2 hours; (b) 3.0N HCl reflux, 3 hours; (c) 1-acetylpiperazine, Hunigs base, DMF, 220° C., microwave, 5 minutes; (d) Zn/HCl/MeOH, reflux, 2 hours; (e) 19, dioxane/water, pH 3.5, 100° C., 5 hours.

Scheme 16 above shows a method for preparing compound I-5. The fluoro group of aryl fluoride 57 (prepared according to scheme 3 using 2-chloropyrimidine to introduce $R^3$) was displaced with t-butylamine to give t-butylamine analog 58. The t-butyl amine was deprotected under acidic conditions to provide aniline intermediate 59. The fluoro group was displaced with 1-acetylpiperazine with Hunigs base in hot DMF in a microwave to give intermediate 60. The nitro group of compound 60 was subsequently reduced with zinc powder in hot HCl/methanol to afford diamine 61. Treatment of diamine 61 with N,N-diethylureamido-2-methyl-thiopseudourea 19 in hot dioxane with buffered water afforded compound I-5.

Scheme 17:

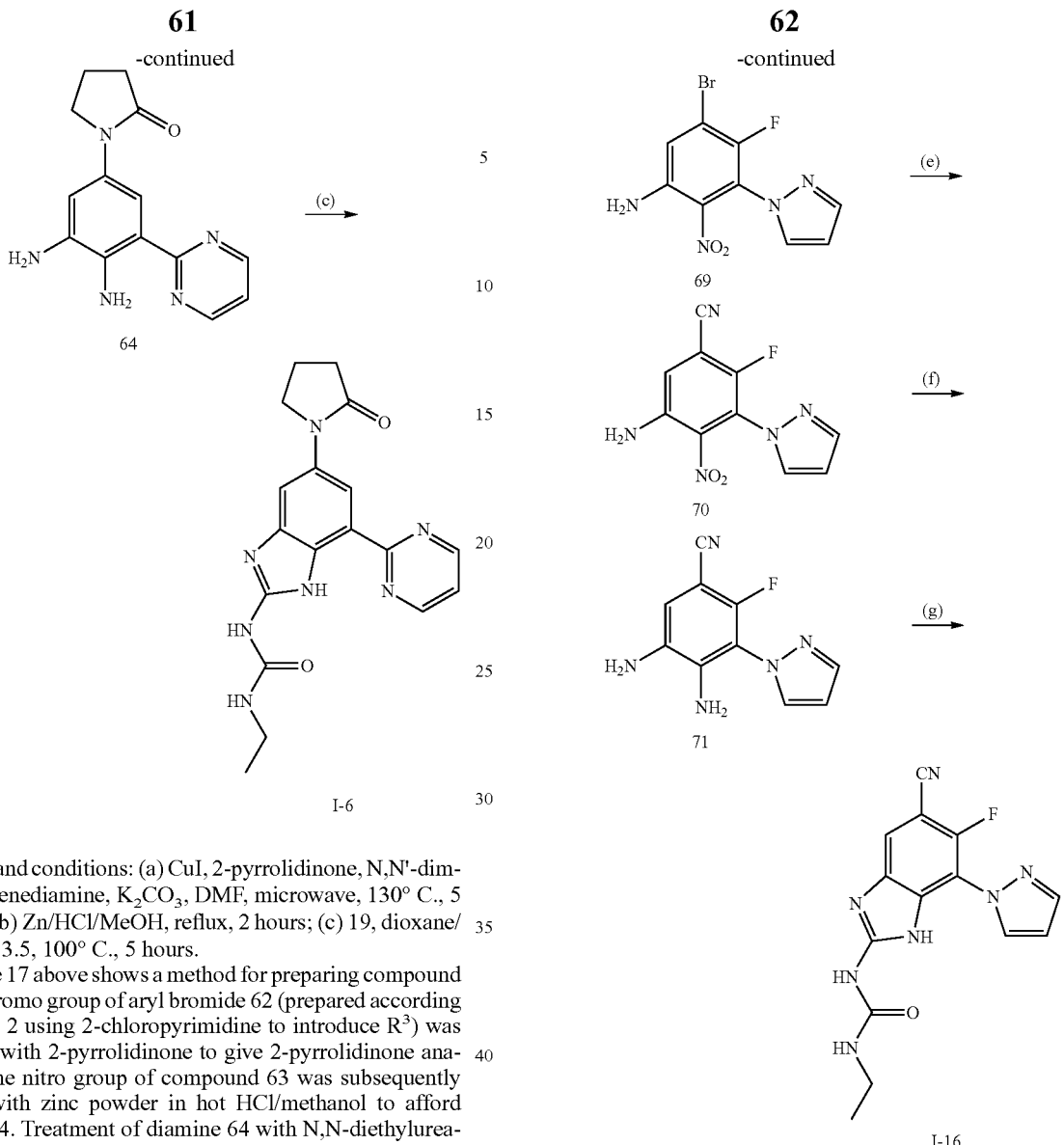

Reagents and conditions: (a) CuI, 2-pyrrolidinone, N,N'-dimethylethylenediamine, K$_2$CO$_3$, DMF, microwave, 130° C., 5 minutes; (b) Zn/HCl/MeOH, reflux, 2 hours; (c) 19, dioxane/water, pH 3.5, 100° C., 5 hours.

Scheme 17 above shows a method for preparing compound I-6. The bromo group of aryl bromide 62 (prepared according to scheme 2 using 2-chloropyrimidine to introduce R$^3$) was displaced with 2-pyrrolidinone to give 2-pyrrolidinone analog 63. The nitro group of compound 63 was subsequently reduced with zinc powder in hot HCl/methanol to afford diamine 64. Treatment of diamine 64 with N,N-diethylureamido-2-methyl-thiopseudourea 19 in hot dioxane with buffered water afforded a good yield of compound I-6.

Scheme 18:

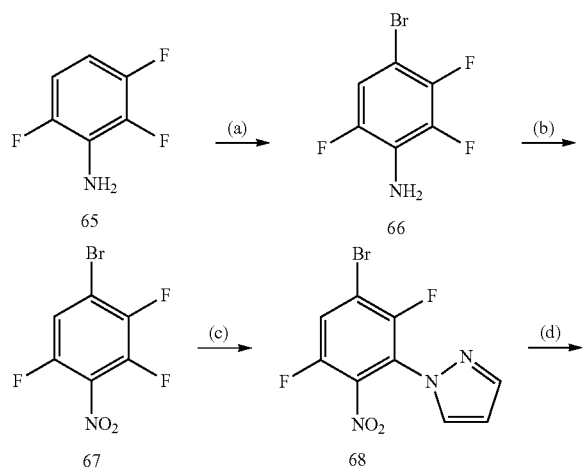

Reagents and conditions: (a) N-bromosuccinimide, DMF, RT, 12 hours; (b) NaBO$_3$ monohydrate, acetic acid, 55° C., 4 hours; (c) NaH, pyrazole, THF, 0° C., 30 minutes; (d) NH$_3$, methanol, 80° C., sealed tube, 18 hours; (e) CuCN, DMF, reflux, 2.5 hours; (f) 10% Pd/C, H$_2$ (1 atm), HCl/methanol, 2 hours; (g) 19, dioxane/water, pH 3.5, 100° C., 12 hours.

Scheme 18 above shows a method for preparing compound I-16. 2,3,6,-Trifluoroaniline 65 (Aldrich) was brominated with NBS in DMF to give aryl bromide 66. The amino group in compound 66 was oxidized with sodium perborate monohydrate to give the nitro analog 67. One fluoro group in compound 67 was displaced with pyrazole anion in THF to give the pyrazole analog 68. Another fluoro group in intermediate 68 was displaced with ammonia to give aniline 69. The bromo group in compound 69 was displaced with copper cyanide to give the cyano intermediate 70. The nitro group of compound 70 was subsequently reduced with 10% Pd/C under 1 atm of H$_2$ to afford diamine 71. Treatment of diamine 71 with N,N-diethylureamido-2-methyl-thiopseudourea 19 in hot dioxane with buffered water gave compound I-16.

Scheme 19:

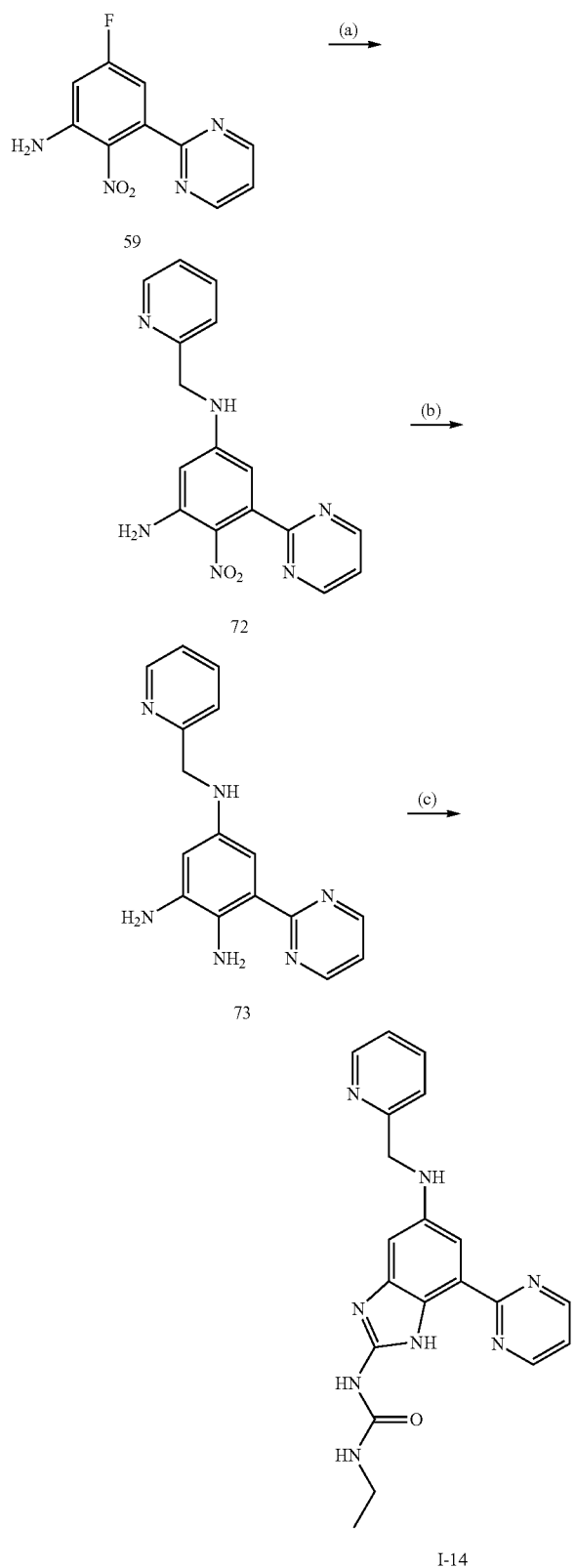

Reagents and conditions: (a) 2-(aminomethyl)pyridine, DMSO, 150° C., 6 hours; (b) Raney-Nickel, MeOH, H$_2$ (1 atm), 2 hours; (c) 19, dioxane/water, pH 3.5, 100° C., 3 hours.

Scheme 19 above shows a method for preparing compound I-14. The fluoro group of aryl fluoride 59 (prepared according to schemes 3 and 16 using 2-chloropyrimidine to introduce R$^3$) was displaced with 2-(aminomethyl)pyridine (Aldrich) to give 2-(aminomethyl)pyridine 72. The nitro group of compound 72 was subsequently reduced with Raney-nickel under H$_2$ (1 atm) to afford diamine 73. Treatment of diamine 73 with N,N-diethylureamido-2-methyl-thiopseudourea 19 in hot dioxane with buffered water afforded a good yield of compound I-14.

Scheme 20:

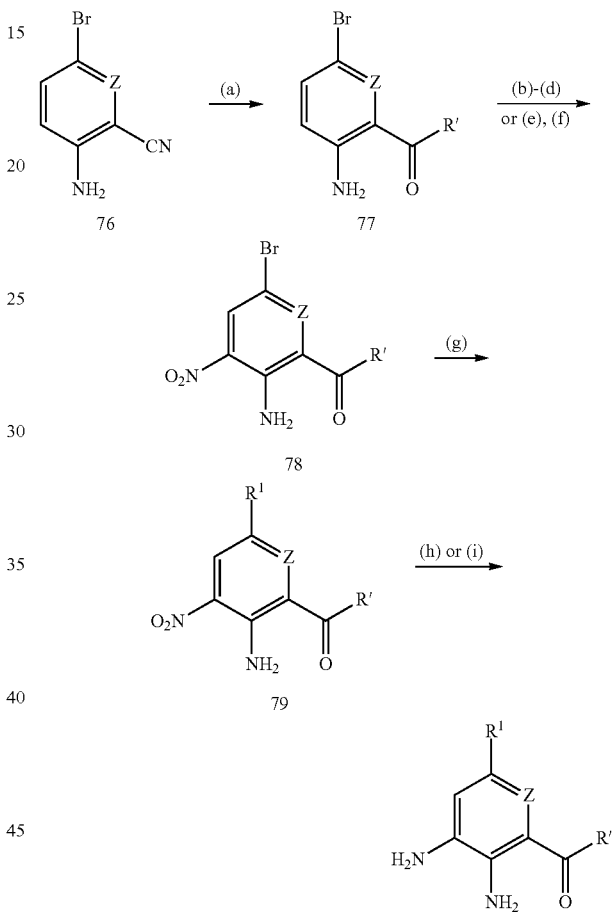

Reagents and conditions: (a) R-magnesium halide, THF, 0° C. to rt; (b) Ac$_2$O, 80° C. (c); HNO$_3$; (d) 6N aq. HCl; (e) trifluoroacetic acid anhydride then KNO$_3$; (f) Na$_2$CO$_3$, MeOH/H$_2$O (9:1), 65° C.; (g) R'-boronate, Pd(PPh$_3$)$_4$, 1N aq. NaHCO$_3$, DME, 90° C. or any amenable procedure from schemes 1-20 to introduce R$^1$; (h) SnCl$_2$.2H$_2$O, EtOH, reflux; and (i) Na$_2$S$_2$O$_4$, EtOH/H$_2$O (3:1), 90° C.

Scheme 20 above shows general method for preparing compounds of formula I wherein R$^3$ is R$^Y$ and R$^Y$ is C(O)R'. The cyano compound 76 is treated with R-magnesium halide to form the ketone 77. The nitro compound 78 is prepared from 77 by treating with acetic anhydride, then nitric acid. Alternatively, 78 can be prepared by treating 77 with trifluoroacetic anydride and potassium nitrate. The nitro compound 78 is then treated with the boronate, as described above, to form compound 79. The nitro group of compound 79 is reduced to form the diamine compound 80 either with SnCl$_2$ (step h) or Na$_2$S$_2$O$_4$ (step i). The diamine compound 80 can then be used to prepare compounds of formula I, wherein R$^3$ is C(O)R', by methods substantially similar to those set forth at Schemes 1 through 20 above.

Scheme 21:

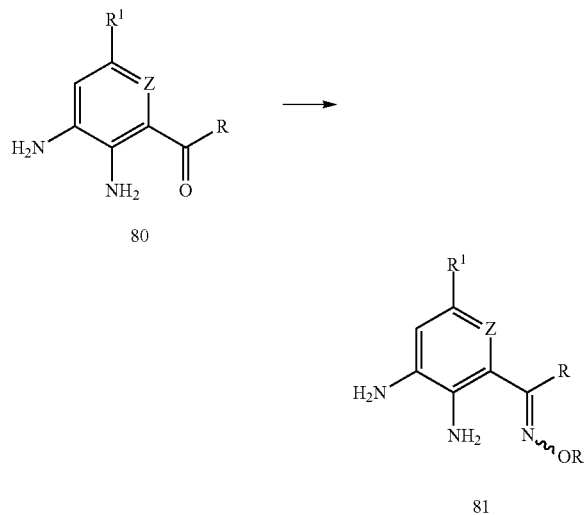

Scheme 21 above shows general method for preparing compounds of formula I wherein R$^3$ is C(R)=NOR'. The ketone compound 80 is treated with potassium acetate and HCl.NH—OR$^1$ to form the oxime compound 81. Compound 81 can then be used to prepare compounds of formula I wherein R$^3$ is C(R')=NOR' using methods substantially similar to those set forth for Schemes 1-20 above.

Scheme 22:

Scheme 22 above shows general method for preparing compounds of formula I wherein Z is C—R$^4$, R$^4$ is F and R$^3$ is CO$_2$R'. Compound 85 is prepared from commercially available starting materials by methods substantially similar to those described by Kim, K. S., et al, *J. Med. Chem.* 1993, 36, 2335. Compound 86 is prepared by treating compound 85 with bromine in acetic acid. Compounds of the present invention wherein R$^3$ is CO$_2$R' can be prepared from compound 86 by methods substantially similar to those described above at Schemes 1 through 20 above.

Scheme 23:

Scheme 23 above shows a general method for preparing N'-alkyl-N-cyanoureas (for example, compound 19a wherein R$^2$ in formula I is ethyl) useful in the preparation of the compounds of the present invention. Cyanamide 88 is treated with ethyl isocyanate 87 in the presence of base to afford, after acidification, compound 19a. Although N'-ethyl-N-cyanourea is depicted, one of skill in the art would understand that a variety of alkyl isocyanates would be amenable to the reaction conditions of Scheme 23 to form a variety of N'-alkyl-N-cyanoureas.

One of skill in the art would recognize that a variety of compounds of the present invention may be prepared according to the general method of Schemes 1 through 23 above, and the synthetic Examples set forth below.

The compounds of this invention are potent inhibitors of gyrase and Topo IV as determined by enzymatic assay. These compounds have also been shown to have antimicrobial activity in an antimicrobial susceptibility assay. The activity of a compound utilized in this invention as an inhibitor of gyrase or Topo IV may be assayed in vitro, in vivo or in a cell line according to methods known in the art. The details of the conditions used for both the enzymatic and the antimicrobial susceptibility assays are set forth in the Examples below.

According to another embodiment, the invention provides a composition comprising a compound of this invention or a pharmaceutically acceptable salt thereof and a pharmaceutically acceptable carrier, adjuvant, or vehicle. The amount of compound in the compositions of this invention is such that is effective to detectably inhibit gyrase, Topo IV, or to measurably decrease bacterial quantity, in a biological sample or in a patient. Preferably the composition of this invention is formulated for administration to a patient in need of such composition. Most preferably, the composition of this invention is formulated for oral administration to a patient.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of gyrase and/or Topo IV activity in a biological sample is useful for a variety of purposes that are known to one of skill in the art. Examples of such purposes include, but are not limited to, blood transfusion, organ-transplantation, biological specimen storage, and biological assays.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "detectably inhibit", as used herein means a measurable change in gyrase, or Topo IV, activity between a sample comprising said composition and gyrase, or Topo IV, and an equivalent sample comprising gyrase, or Topo IV in the absence of said composition.

As used herein, the term "measurably decrease bacterial quantity", as used herein means a measurable change in the number of bacteria between a sample containing said composition and a sample containing only bacteria.

The term "preventing a bacterial infection in a patient" means the prophylatic use of an antibiotic, such as a gyrase inhibitor of the present invention, to prevent a bacterial infection. Treatment with a gyrase inhibitor could be done prophylactically to prevent an infection caused by an organism that is susceptible to the gyrase inhibitor. One general set of conditions where prophylactic treatment could be considered is when an individual is more vulnerable to infection due to, for example, weakened immunity, surgery, trauma, presence of an artificial device in the body (temporary or permanent), an anatomical defect, exposure to high levels of bacteria or possible exposure to a disease-causing pathogen. Examples of factors that could lead to weakened immunity include chemotherapy, radiation therapy, diabetes, advanced age, HIV infection, and transplantation. An example of an anatomical defect would be a defect in the heart valve that increases the risk of bacterial endocarditis. Examples of artificial devices include artificial joints, surgical pins, catheters, etc. Another set of situations where prophylactic use of a gyrase inhibitor might be appropriate would be to prevent the spread of a pathogen between individuals (direct or indirect). A specific example of prophylactic use to prevent the spread of a pathogen is the use of a gyrase inhibitor by individuals in a healthcare institution (for example a hospital or nursing home).

A "pharmaceutically acceptable salt" means any non-toxic salt of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of gyrase and/or Topo IV.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\text{ alkyl})_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of bacterial infections caused by bacteria such as *Streptococcus pneumoniae, Streptococcus pyogenes, Enterococcus faecalis, Enterococcus faecium, Klebsiella pneumoniae, Enterobacter* sps., *Proteus* sps., *Pseudomonas aeruginosa, E. coli, Serratia marcesens, Staphylococcus aureus,* Coag. Neg. Staph, *Haemophilus influenzae, Bacillus anthracis, Mycoplasma pneumoniae, Moraxella catarralis, Chlamydia pneumoniae, Legionella pneumophila, Mycobacterium tuberculosis, Staphylococcus epidermidis,* or *Helicobacter pylori*.

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of resistant bacterial infections caused by bacteria such as Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*, Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*, Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplasma pneumoniae*, Isoniazid resistant *Mycobacterium tuberculosis*, Rifampin resistant *Mycobacterium tuberculosis*, Methicillin resistent Coagulase negative staphylcocci, Fluoroquinolone resistant Coagulase negative staphylcocci, Glycopeptide intermediate resistant *Staphylococcus aureus*, Vancomycin resistant *Staphylococcus aureus*, Hetero vancomycin intermediate resistant *Staphylococcus aureus*, Hetero vancomycin resistant *Staphylococcus aureus*, Macrolide-Lincosamide-Streptogramin resistant *Staphylococcus*, β-lactam resistant *Enterococcus faecalis*, β-lactam resistant *Enterococcus faecium*, Ketolide resistant *Streptococcus pneumoniae*, Ketolide resistant *Streptococcus pyogenes*, Macrolide resistant *Streptococcus pyogenes*, or Vancomycin resistant *staphylococcus epidermidis*.

Typically, the pharmaceutical compositions of this invention will be administered from about 1 to 5 times per day or alternatively, as a continuous infusion. Or, alternatively, the compositions of the present invention may be administered in a pulsatile formulation. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula I and one or more additional therapeutic or prophylactic agents, both the compound and the additional agent should be present at dosage levels of between about 10% to 80% of the dosage normally administered in a monotherapy regime.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence or disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated". Such agents include, but are not limited to, an antibiotic, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin, an anti-vascular hyperproliferation compound, or an agent which increases the susceptibility of bacterial organisms to antibiotics.

Agents, which increase the susceptibility of bacterial organisms to antibiotics, are known. For example, U.S. Pat. No. 5,523,288, U.S. Pat. No. 5,783,561 and U.S. Pat. No. 6,140,306 describe methods of using bactericidal/permeability-increasing protein (BPI) for increasing antibiotic susceptibility of gram-positive and gram-negative bacteria. Agents that increase the permeability of the outer membrane of bacterial organisms have been described by Vaara, M. in *Microbiological Reviews* (1992) pp. 395-411, and the sensitization of gram-negative bacteria has been described by Tsubery, H., et al, in *J. Med. Chem.* (2000) pp. 3085-3092.

According to one embodiment, the present invention provides a method of inhibiting gyrase or Topo IV activity in a biological sample, comprising the step of contacting said biological sample with a compound of formula I or a composition comprising a compound of formula I and a pharmaceutically acceptable carrier, adjuvant, or vehicle.

According to one embodiment, the present invention provides a method of inhibiting gyrase and Topo IV activity in a biological sample, comprising the step of contacting said biological sample with a compound of formula I or a composition comprising a compound of formula I and a pharmaceutically acceptable carrier, adjuvant, or vehicle.

According to another embodiment, the present invention provides a method of inhibiting gyrase or Topo IV activity in a patient, comprising the step of administering to said patient a compound of formula I or a composition comprising a compound of formula I and a pharmaceutically acceptable carrier, adjuvant, or vehicle.

According to another embodiment, the present invention provides a method of inhibiting gyrase and Topo IV activity in a patient, comprising the step of administering to said patient a compound of formula I or a composition comprising a compound of formula I and a pharmaceutically acceptable carrier, adjuvant, or vehicle.

According to another embodiment, the present invention provides a method of inhibiting Topo IV in a biological sample.

According to another embodiment, the present invention provides a method of decreasing bacterial quantity in a biological sample.

According to another embodiment, the present invention provides a method of decreasing bacterial quantity in a patient, comprising the step of administering to said patient a compound of formula I or a composition comprising a compound of formula I and a pharmaceutically acceptable carrier, adjuvant, or vehicle.

According to another embodiment, the present invention provides a method of preventing, treating, or lessening the severity of a bacterial infection in a patient, comprising the step of administering to said patient a compound of formula I or a composition comprising a compound of formula I and a pharmaceutically acceptable carrier, adjuvant, or vehicle. In another embodiment, the present invention provides a method wherein the bacterial infection to be treated or prevented is characterized by the presence of a susceptible bacterial organism.

According to another embodiment, the methods of the present invention are useful to treat patients in the veterinarian field including, but not limited to, zoo, laboratory, and farm animals including primates, rodents, and birds. Examples of said animals include, but are not limited to, guinea pigs, hamsters, gerbils, rat, mice, rabbits, dogs, cats, horses, pigs, sheep, cows, goats, deer, rhesus monkeys, monkeys, tamarinds, apes, baboons, gorillas, chimpanzees, orangutans, gibbons, ostriches, chickens, turkeys, ducks, and geese.

In another embodiment, the present invention provides a method wherein the bacterial infection to be treated or prevented is characterized by the presence of one or more of the following: *Streptococcus pneumoniae, Streptococcus pyogenes, Enterococcus faecalis, Enterococcus faecium, Klebsiella pneumoniae, Enterobacter* sps., *Proteus* sps., *Pseudomonas aeruginosa, E. coli, Serratia marcesens, Staphylococcus aureus*, Coag. Neg. Staph, *Haemophilus influenzae, Bacillus anthracis, Mycoplasma pneumoniae, Moraxella catarralis, Chlamydia pneumoniae, Legionella pneumophila, Mycobacterium tuberculosis, Staphylococcus epidermidis*, or *Helicobacter pylori*.

In another embodiment, the present invention provides a method wherein the bacterial infection to be treated or prevented is characterized by the presence of one or more of the following: *Streptococcus pneumoniae, Enterococcus faecalis*, or *Staphylococcus aureus*.

In another embodiment, the present invention provides a method wherein the bacterial infection to be treated or prevented is characterized by the presence of one or more of the following: *E. coli, Moraxella catarralis*, or *Haemophilus influenzae*.

In another embodiment, the present invention provides a method wherein the bacterial infection to be treated or prevented is characterized by the presence of one or more of the following: Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*, Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*, Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplama pneumoniae*, Isoniazid resistant *Mycobacterium tuberculosis*, Rifampin resistant *Mycobacterium tuberculosis*, Methicillin resistant Coagulase negative staphylcocci, Fluoroquinolone resistant Coagulase negative staphylcocci, Glycopeptide intermediate resistant *Staphylococcus aureus*, Vancomycin resistant *Staphylococcus aureus*, Hetero vancomycin intermediate resistant *Staphylococcus aureus*, Hetero vancomycin resistant *Staphylococcus aureus*, Macrolide-Lincosamide-Streptogramin resistant *Staphylococcus*, β-lactam resistant *Enterococcus faecalis*, β-lactam resistant *Enterococcus faecium*, Ketolide resistant *Streptococcus pneumoniae*, Ketolide resistant *Streptococcus pyogenes*, Macrolide resistant *Streptococcus pyogenes*, or Vancomycin resistant *staphylococcus epidermidis*.

According to another embodiment of the methods of the present invention, the Methicillin resistant Staphylococci are selected from Methicillin resistant *Staphylococcus aureus*, Methicillin resistant *Staphylococcus epidermidis*, or Methicillin resistant Coagulase negative *staphylcoccus*.

According to another embodiment of the methods of the present invention, the Fluoroquinolone resistant Staphylococci are selected from Fluoroquinolone resistant *Staphylococcus aureus*, Fluoroquinolone resistant *Staphylococcus epidermidis*, or Fluoroquinolone resistant Coagulase negative *staphylcoccus*.

According to another embodiment of the methods of the present invention, the Glycopepetide resistant Staphylococci are selected from Glycopeptide intermediate resistant *Staphylococcus aureus*, Vancomycin resistant *Staphylococcus aureus*, Vancomycin intermediate *Staphylococcus aureus*, Hetero vancomycin intermediate resistant *Staphylococcus aureus*, or Hetero vancomycin resistant *Staphylococcus aureus*.

According to another embodiment of the methods of the present invention, the Macrolide-Lincosamide-Streptogramin resistant Staphylococci is Macrolide-Lincosamide-Streptogramin resistant *Staphylococcus aureus*.

According to another embodiment of the methods of the present invention, the Linezolid resistant Enterococci are selected from Linezolid resistant *Enterococcus faecalis*, or Linezolid resistant *Enterococcus faecium*.

According to another embodiment of the methods of the present invention, the Glycopepetide resistant Enterococci are selected from Vancomycin resistant *Enterococcus faecium* or Vancomycin resistant *Enterococcus faecalis*.

According to another embodiment of the methods of the present invention, the β-lactam resistant *Enterococcus faecalis* and β-lactam resistant *Enterococcus faecium*.

According to another embodiment of the methods of the present invention, the Penicillin resistant Streptococci include Penicillin resistant *Streptococcus pneumoniae*.

According to another embodiment of the methods of the present invention, the Macrolide resistant Streptococci is Macrolide resistant *Streptococcus pneumonia*.

According to another embodiment of the methods of the present invention, the Ketolide resistant Streptococci are selected from Macrolide resistant *Streptococcus pneumoniae* and Ketolide resistant *Streptococcus pyogenes*.

According to another embodiment of the methods of the present invention, the Fluoroquinolone resistant Streptococci is Fluoroquinolone resistant *Streptococcus pneumoniae*.

According to another embodiment of the methods of the present invention, the β-lactam resistant *Haemophilus* is β-lactam resistant *Haemophilus influenzae*.

According to another embodiment of the methods of the present invention, the Fluoroquinolone resistant *Haemophilus* is Fluoroquinolone resistant *Haemophilus influenzae*.

According to another embodiment of the methods of the present invention, the Macrolide resistant *Haemophilus* is Macrolide resistant *Haemophilus influenzae*.

According to another embodiment of the methods of the present invention, the Macrolide resistant *Mycoplasma* is Macrolide resistant *Mycoplama pneumoniae*.

According to another embodiment of the methods of the present invention, the Isoniazid resistant *Mycobacterium* is Isoniazid resistant *Mycobacterium tuberculosis*.

According to another embodiment of the methods of the present invention, the Rifampin resistant *Mycobacterium* is Rifampin resistant *Mycobacterium tuberculosis*.

According to another embodiment of the methods of the present invention, the β-lactam resistant *Moraxella* is β-lactam resistant *Moraxella catarrhalis*.

According to another embodiment of the methods of the present invention, the bacterial infection is characterized by the presence of one or more of the following: Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*, Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*, Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplama pneumoniae*, Isoniazid resistant *Mycobacterium tuberculosis*, or Rifampin resistant *Mycobacterium tuberculosis*.

According to another embodiment of the methods of the present invention, the bacterial infection is characterized by the presence of one or more of the following: Methicillin resistant *Staphylococcus aureus*, Methicillin resistant *Staphylococcus epidermidis*, Methicillin resistant Coagulase negative staphylcocci, Fluoroquinolone resistant *Staphylococcus aureus*, Fluoroquinolone resistant *Staphylococcus epidermidis*, Fluoroquinolone resistant Coagulase negative staphylcocci, Vancomycin resistant *Staphylococcus aureus*, Glycopeptide intermediate resistant *Staphylococcus aureus*, Vancomycin resistant *Staphylococcus aureus*, Vancomycin intermediate resistant *Staphylococcus aureus*, Hetero vancomycin intermediate resistant *Staphylococcus aureus*, Hetero vancomycin resistant *Staphylococcus aureus*, Vancomycin resistant *Enterococcus faecium*, Vancomycin resistant *Enterococcus faecalis*, Penicillin resistant *Streptococcus pneumoniae*, Macrolide resistant *Streptococcus pneumoniae*, Fluoroquinolone resistant *Streptococcus pneumoniae*, Macrolide resistant *Streptococcus pyogenes*, or β-lactam resistant *Haemophilus influenzae*.

According to another embodiment of the present invention, the methods further comprise the step of administering to the patient one or more additional therapeutic antibacterial agents other than a compound of the present invention (see, e.g. http://www.fda.gov/cvm).

According to another embodiment of the present invention, the methods further comprise the step of administering to said patient one or more additional therapeutic agents either as part of a multiple dosage form together with said compound or as a separate dosage form wherein said one or more additional therapeutic agents include an antibiotic selected from a natural penicillin, a penicillinase-resistant penicillin, an antipseudomonal penicillin, an aminopenicillin, a first generation cephlosporin, a second generation cephalosporin, a third generation cephalosporin, a fourth generation cephalosporin, a carbapenem, a cephamycin, a monobactam, a quinolone, a fluoroquinolone, an aminoglycoside, a macrolide, a ketolide, a tetracycline, a glycopeptide, a streptogramin, an oxazolidone, a rifamycin, or other antibiotics.

According to another embodiment of the present invention, the methods further comprise the step of administering to said human one or more additional therapeutic agents either as part of a multiple dosage form together with said compound or as a separate dosage form wherein said one or more additional therapeutic agents include an antibiotic selected from a natural penicillin, a penicillinase-resistant penicillin, an antipseudomonal penicillin, an aminopenicillin, a first generation cephlosporin, a second generation cephalosporin, a third generation cephalosporin, a fourth generation cephalosporin, a carbapenem, a cephamycin, a monobactam, a quinolone, a fluoroquinolone, an aminoglycoside, a macrolide, a ketolide, a tetracycline, a glycopeptide, a streptogramin, an oxazolidone, a rifamycin, or other antibiotics.

According to another embodiment of the present invention, the methods further comprise the step of administering to said patient one or more additional therapeutic agents either as part of a multiple dosage form together with said compound or as a separate dosage form wherein said one or more additional therapeutic agents are selected from a natural penicillin including Benzathine penicillin G, Penicillin G and Penicillin V, from a penicillinase-resistant penicillin including Cloxacillin, Dicloxacillin, Nafcillin and Oxacillin, from a antipseudomonal penicillin including Carbenicillin, Mezlocillin, Pipercillin, Pipercillin/tazobactam, Ticaricillin and Ticaricillin/Clavulanate, from an aminopenicillin including Amoxicillin, Ampicillin and Ampicillin/Sulbactam, from a first generation cephalosporin including Cefazolin, Cefadroxil, Cephalexin and Cephadrine, from a second generation cephalosporin including Cefaclor, Cefaclor-CD, Cefamandole, Cefonacid, Cefprozil, Loracarbef and Cefuroxime, from a third generation cephalosporin including Cefdinir, Cefixime, Cefoperazone, Cefotaxime, Cefpodoxime, Ceftazidime, Ceftibuten, Ceftizoxme and Ceftriaxone, from a fourth generation cephalosporin including Cefepime, from a Cephamycin including Cefotetan and Cefoxitin, from a carbapenem including Imipenem and Meropenem, from a monobactam including Aztreonam, from a quinolone including Cinoxacin, Nalidixic acid, Oxolininc acid and Pipemidic acid, from a fluoroquinolone including Cirpofloxacin, Enoxacin, Gatifloxacin, Grepafloxacin, Levofloxacin, Lomefloxacin, Moxifloxacin, Norfloxacin, Ofloxacin and Sparfloxacin, from an aminoglycoside including Amikacin, Gentamicin, Kanamycin, Neomycin, Netilmicin, Spectinomycin, Streptomycin and Tobramycin, from a macrolide including Azithromycin, Clarithromycin and Erythromycin, from a ketolide including Telithromycin, from a Tetracycline including Chlortetracycline, Demeclocycline, Doxycycline, Minocycline and Tetracycline, from a glycopeptide including Oritavancin, Teicoplanin and Vancomycin, from a streptogramin including Dalfopristin/quinupristin, from an oxazolidone including Linezolid, from a Rifamycin including Rifabutin and Rifampin and from other antibiotics including bactitracin, chloramphenicol, clindamycin, isoniazid, metronidazole, polymyxin B, pyrazinamide, and trimethoprim/sulfamethoxazole.

According to another embodiment of the present invention, the methods further comprise the step of administering to said human one or more additional therapeutic agents either as part of a multiple dosage form together with said compound or as a separate dosage form wherein said one or more additional therapeutic agents are selected from a natural penicillin including Benzathine penicillin G, Penicillin G and Penicillin V, from a penicillinase-resistant penicillin including Cloxacillin, Dicloxacillin, Nafcillin and Oxacillin, from a antipseudomonal penicillin including Carbenicillin, Mezlocillin, Pipercillin, Pipercillin/tazobactam, Ticaricillin and Ticaricillin/Clavulanate, from an aminopenicillin including Amoxicillin, Ampicillin and Ampicillin/Sulbactam, from a first generation cephalosporin including Cefazolin, Cefadroxil, Cephalexin and Cephadrine, from a second generation cephalosporin including Cefaclor, Cefaclor-CD, Cefamandole, Cefonacid, Cefprozil, Loracarbef and Cefuroxime, from a third generation cephalosporin including Cefdinir, Cefixime, Cefoperazone, Cefotaxime, Cefpodoxime, Ceftazidime, Ceftibuten, Ceftizoxme and Ceftriaxone, from a fourth generation cephalosporin including Cefepime, from a Cephamycin including Cefotetan and Cefoxitin, from a carbapenem including Imipenem and Meropenem, from a monobactam including Aztreonam, from a quinolone including Cinoxacin, Nalidixic acid, Oxolininc acid and Pipemidic acid, from a fluoroquinolone including Cirpofloxacin, Enoxacin, Gatifloxacin, Grepafloxacin, Levofloxacin, Lomefloxacin, Moxifloxacin, Norfloxacin, Ofloxacin and Sparfloxacin, from an aminoglycoside including Amikacin, Gentamicin, Kanamycin, Neomycin, Netilmicin, Spectinomycin, Streptomycin and Tobramycin, from a macrolide including Azithromycin, Clarithromycin and Erythromycin, from a ketolide including Telithromycin, from a Tetracycline including Chlortetracycline, Demeclocycline, Doxycycline, Minocycline and Tetracycline, from a glycopeptide including Oritavancin, Teicoplanin and Vancomycin, from a streptogramin including Dalfopristin/quinupristin, from an oxazolidone including Linezolid, from a Rifamycin including Rifabutin and Rifampin and from other antibiotics including bactitracin, chloramphenicol, clindamycin, isoniazid, metronidazole, polymyxin B, pyrazinamide, and trimethoprim/sulfamethoxazole.

According to another embodiment of the present invention, the methods further comprise the step of administering to said patient one or more additional therapeutic agents either as part of a multiple dosage form together with said compound or as a separate dosage form wherein said one or more additional therapeutic agents are selected from a natural penicillin including Penicillin G, from a penicillinase-resistant penicillin including Nafcillin and Oxacillin, from an antipseudomonal penicillin including Pipercillin/tazobactam, from an aminopenicillin including Amoxicillin, from a first generation cephalosporin including Cephalexin, from a second generation cephalosporin including Cefaclor, Cefaclor-CD and Cefuroxime, from a third generation cephalosporin including Ceftazidime and Ceftriaxone, from a fourth generation cephalosporin including Cefepime, from a fluoroquinolone including Cirpofloxacin, Gatifloxacin, Levofloxacin and Moxifloxacin, from an aminoglycoside including Tobramycin, from a macrolide including Azithromycin and Clarithromycin, from a Tetracycline including Doxycycline, from a glycopeptide including Vancomycin, from a Rifamycin including Rifampin and from other antibiotics including isoniazid, pyrazinamide, or trimethoprim/sulfamethoxazole.

According to another embodiment of the present invention, the methods further comprise the step of administering to said human one or more additional therapeutic agents either as part of a multiple dosage form together with said compound or as a separate dosage form wherein said one or more additional therapeutic agents are selected from a natural penicillin including Penicillin G, from a penicillinase-resistant penicillin including Nafcillin and Oxacillin, from an antipseudomonal penicillin including Pipercillin/tazobactam, from an aminopenicillin including Amoxicillin, from a first generation cephalosporin including Cephalexin, from a second generation cephalosporin including Cefaclor, Cefaclor-CD and Cefuroxime, from a third generation cephalosporin including Ceftazidime and Ceftriaxone, from a fourth generation cephalosporin including Cefepime, from a fluoroquinolone including Cirpofloxacin, Gatifloxacin, Levofloxacin and Moxifloxacin, from an aminoglycoside including Tobramycin, from a macrolide including Azithromycin and Clarithromycin, from a Tetracycline including Doxycycline, from a glycopeptide including Vancomycin, from a Rifamycin including Rifampin and from other antibiotics including isoniazid, pyrazinamide, or trimethoprim/sulfamethoxazole.

According to another embodiment, the present invention provides a method of preventing, treating, or lessening the severity of a bacterial infection in a patient wherein the bacterial infection to be treated or prevented is selected from one or more of the following: upper respiratory infections, lower respiratory infections, ear infections, pleuropulmonary and bronchial infections, urinary tract infections, intra-abdominal infections, cardiovascular infections, a blood stream infection, sepsis, CNS infections, skin and soft tissue infections, GI infections, bone and joint infections, genital infections, eye infections, or granulomatous infections. In another embodiment, the bacterial infection to be treated is selected from one or more of the following: pharyngitis, sinusitis, otitis externa, otitis media, bronchitis, empyema, pneumonia, cystitis and pyelonephritis, renal calculi, prostatitis, peritonitis, dialysis-associated peritonitis, visceral abscesses, endocarditis, myocarditis, pericarditis, transfusion-associated sepsis, meningitis, encephalitis, brain abscess, osteomyelitis, arthritis, genital ulcers, urethritis, vaginitis, cervicitis, gingivitis, conjunctivitis, keratitis, endophthalmitisa, or an infection of febrile neutropenic patients.

According to another embodiment, the invention provides a method for treating or preventing a susceptible bacterial organism in a patient wherein said method further comprises the step of administering to said patient an additional therapeutic agent either as part of a multiple dosage form together with said compound or as a separate dosage form.

According to another embodiment, the invention provides a method for treating or preventing a susceptible bacterial organism in a patient wherein said method further comprises the step of administering to said patient an agent that increases the susceptibility of bacterial organisms to antibiotics.

According to another embodiment of the present invention, the methods further comprise the step of administering to a patient, one or more additional therapeutic agents that increase the susceptibility of bacterial organisms to antibiotics.

According to another embodiment of the present invention, the methods further comprise the step of administering to a human, one or more additional therapeutic agents that increase the susceptibility of bacterial organisms to antibiotics.

According to another embodiment of the present invention, the methods further comprise the step of administering to a patient, one or more additional therapeutic agents that increase the susceptibility of bacterial organisms to antibiotics including a biofilm inhibitor.

According to another embodiment of the present invention, the methods further comprise the step of administering to a human, one or more additional therapeutic agents that increase the susceptibility of bacterial organisms to antibiotics including a biofilm inhibitor.

The pharmaceutical compositions and methods of this invention will be useful generally for controlling bacterial infections in vivo. Examples of bacterial organisms that may be controlled by the compositions and methods of this invention include, but are not limited to, the following organisms: *Streptococcus pneumoniae, Streptococcus pyogenes, Enterococcus faecalis, Enterococcus faecium, Klebsiella pneumoniae, Enterobacter sps. Proteus sps. Pseudomonas aeruginosa, E. coli, Serratia marcesens, Staphylococcus aureus,* Coag. Neg. Staph, *Haemophilus infuenzae, Bacillus anthracis, Mycoplasma pneumoniae, Moraxella catarralis, H. influenzae, Chlamydia pneumoniae, Legionella pneumophila, Mycobacterium tuberculosis, Helicobacter pylori, Staphylococcus epidermidis. Chlamydia pneumoniae, Legionella pneumophila, Mycobacterium tuberculosis,* or *Helicobacter pylori.*

In another embodiment, the pharmaceutical compositions and methods of this invention will be useful generally for controlling bacterial infections in vivo caused by the following the following organisms: *Streptococcus pneumoniae, Streptococcus pyogenes, Enterococcus faecalis, Enterococcus faecium, Staphylococcus aureus,* Coag. Neg. Staph, *Haemophilus infuenzae, Bacillus anthracis, Mycoplasma pneumoniae, Moraxella catarralis, H. influenzae, Chlamydia pneumoniae, Legionella pneumophila, Mycobacterium tuberculosis, Helicobacter pylori, Staphylococcus epidermidis. Chlamydia pneumoniae, Legionella pneumophila, Mycobacterium tuberculosis, Staphylococcus saprophyticus,* or *Helicobacter pylori.*

In another embodiment, the pharmaceutical compositions and methods of this invention will be useful generally for controlling bacterial infections in vivo caused by the following the following organisms: *Streptococcus pneumoniae, Streptococcus pyogenes, Enterococcus faecalis, Enterococcus faecium, Staphylococcus aureus,* Coag. Neg. *Staph, Bacillus anthracis, Staphylococcus epidermidis, Staphylococcus saprophyticus,* or *Mycobacterium tuberculosis.*

The compositions and methods will therefore be useful for controlling, treating or reducing the advancement, severity or effects of nosocomial or non-nosocomial infections. Examples of nosocomial and non-nosocomial infections include but are not limited to upper respiratory infections, lower respiratory infections, ear infections, pleuropulmonary and bronchial infections, urinary tract infections, intra-abdominal infections, cardiovascular infections, a blood stream infection, sepsis, CNS infections, skin and soft tissue infections, GI infections, bone and joint infections, genital infections, eye infections, or granulomatous infections. Examples of specific bacterial infections include but are not limited to pharyngitis, sinusitis, otitis externa, otitis media, bronchitis, empyema, pneumonia, cystitis and pyelonephritis, renal calculi, prostatitis, peritonitis, dialysis-associated peritonitis, visceral abscesses, endocarditis, myocarditis, pericarditis, transfusion-associated sepsis, meningitis, encephalitis, brain abscess, osteomyelitis, arthritis, genital ulcers, urethritis, vaginitis, cervicitis, gingivitis, conjunctivitis, keratitis, endophthalmitisa, or an infection of febrile neutropenic patients.

The term "pharmaceutically effective amount" refers to an amount effective in treating or ameliorating a bacterial infection in a patient. The term "prophylactically effective amount" refers to an amount effective in preventing or substantially lessening a bacterial infection in a patient.

The compounds of this invention may be employed in a conventional manner for controlling bacterial infections levels in vivo and for treating diseases or reducing the advancement or severity of effects that are mediated by bacteria. Such methods of treatment, their dosage levels and requirements may be selected by those of ordinary skill in the art from available methods and techniques.

For example, a compound of this invention may be combined with a pharmaceutically acceptable adjuvant for administration to a patient suffering from a bacterial infection or disease in a pharmaceutically acceptable manner and in an amount effective to lessen the severity of that infection or disease.

Alternatively, the compounds of this invention may be used in compositions and methods for treating or protecting individuals against bacterial infections or diseases over extended periods of time. The compounds may be employed in such compositions either alone or together with other compounds of this invention in a manner consistent with the conventional utilization of enzyme inhibitors in pharmaceutical compositions. For example, a compound of this invention may be combined with pharmaceutically acceptable adjuvants conventionally employed in vaccines and administered in prophylactically effective amounts to protect individuals over an extended period of time against bacterial infections or diseases.

The compounds of formula I may also be co-administered with other antibiotics to increase the effect of therapy or prophylaxis against various bacterial infections. When the compounds of this invention are administered in combination therapies with other agents, they may be administered sequentially or concurrently to the patient. Alternatively, pharmaceutical or prophylactic compositions according to this invention comprise a combination of a compound of formula I and another therapeutic or prophylactic agent.

The additional therapeutic agents described above may be administered separately, as part of a multiple dosage regimen, from the inhibitor-containing composition. Alternatively, these agents may be part of a single dosage form, mixed together with the inhibitor in a single composition.

In order that this invention be more fully understood, the following examples are set forth. These examples are for the purpose of illustration only and are not to be construed as limiting the scope of the invention in any way.

EXAMPLES

Example 1

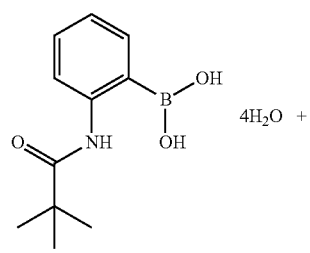

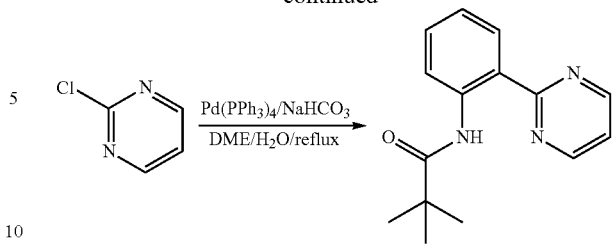

2,2-Dimethyl-N-(2-pyrimidin-2-yl-phenyl)-propionamide

A 5 L flask was charged with the above depicted boronic acid as a tetrahydrate (281.4 grams, 960 mmoles), 2-chloropyrimidine (100 g, 874 mmoles), NaHCO$_3$ (146.8 grams, 1.746 moles), and Pd(PPh$_3$)$_4$ (10.0 grams, 8.72 mmoles). Water (1 L) and dimethoxyethane (1 L) were added, and the mixture was heated slowly to 83° C. (internal temperature) over a 1 hour period with overhead stirring. After ~2 hours all solids had dissolved. The reaction was allowed to stir for 8 hours. The mixture was cooled to room temperature and stirred overnight after which time a thick precipitate had formed. The crude mixture was diluted with water (2 L) and stirred for an additional 2 hours after which time the mixture was filtered and the solids were washed sequentially with water, 0.1N NaOH, and water again. The solids were then dried under high vacuum at 50° C. to afford the title compound (~233 grams) as a tan powder.

Example 2

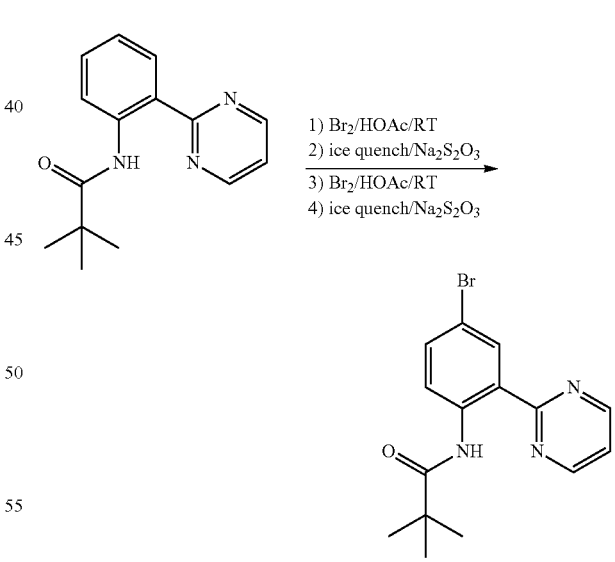

N-(4-Bromo-2-pyrimidin-2-yl-phenyl)-2,2-dimethylpropionamide

To a room temperature suspension of 2,2-dimethyl-N-(2-pyrimidin-2-yl-phenyl)-propionamide (~117 grams, 437 mmoles) in acetic acid (1 L) was added bromine (67 mL, 1.31 moles) as a solution in 100 mL of acetic acid over a 1 hour period. The heterogeneous mixture was stirred at room temperature for 5 hours over which time a thick precipitate formed. The mixture was then poured over ice, diluted with 1N Na$_2$S$_2$O$_3$ (2 L), and stirred for 1 hour. The solids were filtered, resuspended in water (2 L), stirred for 1 hour, then filtered and washed with water again. The resulting solids were pumped to dryness at 50° C., resuspended in HOAc (1 L), and treated with bromine (22 mL, 430 mmoles) in acetic acid solution (20 mL) over a 20 minute period. The resulting heterogeneous mixture was stirred for 5 hours, then quenched and treated as described above. The resulting solids were vacuum dried at 50° C. to afford the title compound (165 grams) as a tan powder.

Example 3

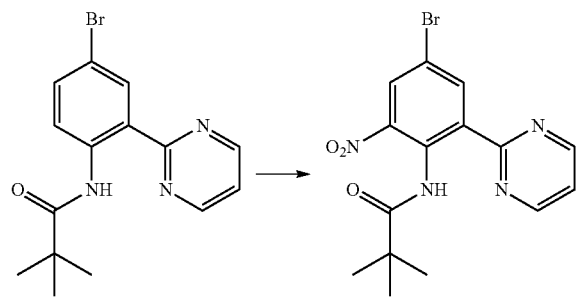 [SMILES: CC(C)(C)C(=O)Nc1ccc(Br)cc1-c1ncccn1 ; CC(C)(C)C(=O)Nc1c(-c2ncccn2)cc(Br)cc1[N+](=O)[O-]]

N-(4-Bromo-2-nitro-6-pyrimidin-2-yl-phenyl)-2,2-dimethyl-propionamide

To a 5° C. suspension of N-(4-bromo-2-pyrimidin-2-yl-phenyl)-2,2-dimethyl-propionamide (32.6 grams, 97.5 mmoles) in TFA (400 mL) was added 90% nitric acid (70 mL, 1.46 mmoles) over a 30 minute period. The mixture was then allowed to warm to room temperature and stir for a total of 2 hours. The crude reaction (now homogenous) was poured into ice producing a pasty mass. The mixture was diluted to 2 L total volume with water, treated with 500 mL of methanol, and vigorously stirred for 12 hours. The resulting solids were filtered, washed with copious amounts of water, then vacuum dried at 50° C. to afford the title compound (29.9 grams, 81% yield) as a tan powder.

Example 4

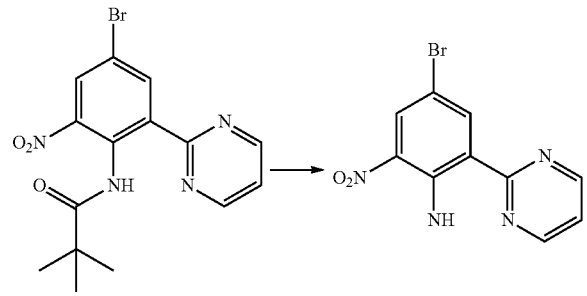 [SMILES: CC(C)(C)C(=O)Nc1c(-c2ncccn2)cc(Br)cc1[N+](=O)[O-] ; Nc1c(-c2ncccn2)cc(Br)cc1[N+](=O)[O-]]

4-Bromo-2-nitro-6-pyrimidin-2-yl-phenylamine

A suspension of N-(4-bromo-2-nitro-6-pyrimidin-2-yl-phenyl)-2,2-dimethyl-propionamide (29.9 grams, 78.8 mmoles) in conc. HCl (200 mL) was refluxed for 8 hours. The partially homogeneous crude reaction was then cooled to room temperature, diluted with water (500 mL), and the resulting precipitate was stirred for 1 hour. The solids were then filtered, washed with water, and vacuum dried at 50° C. to afford the title compound (21.1 grams, 91% yield) as an orange powder.

Example 5

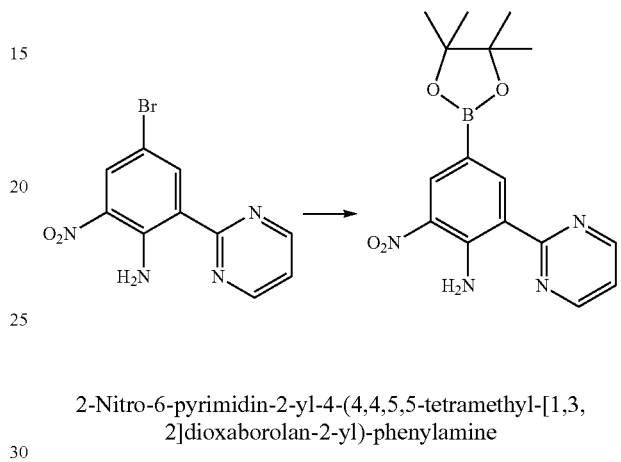

2-Nitro-6-pyrimidin-2-yl-4-(4,4,5,5-tetramethyl-[1,3,2]dioxaborolan-2-yl)-phenylamine A mixture of 4-bromo-2-nitro-6-pyrimidin-2-yl-phenylamine (1.82 g, 6.2 mmol), bis(pinacolato)diboron (3.144 g, 12.4 mmol), PdCl$_2$dppf$_2$ (453 mg, 0.6 mmol) and KOAc (3.03 g, 31 mmol) in dioxane (60 ml) was heated at 105° C. for 2.5 hours. The reaction was filtered and washed with dichloromethane. The combined filtrates were concentrated under vacuum and water (100 ml) was added to the residue. Extraction with dichloromethane (3×50 ml), drying and concentration gave a residue, which was washed with ether-hexane to afford the title compound (2.07 g, 98%).

Example 6

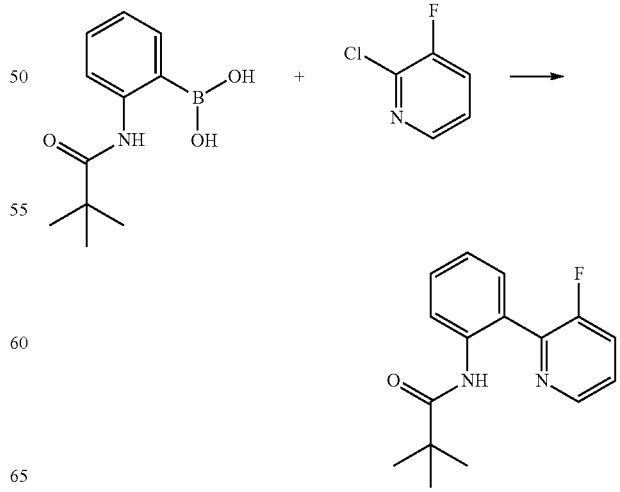

N-[2-(3-Fluoro-pyridin-2-yl)-phenyl]-2,2-dimethyl-propionamide

A 3 L flask was charged with the above depicted boronic acid as a tetrahydrate (92.1 grams, 314 mmoles), chlorofluoropyridine (37.6 g, 286 mmoles), NaHCO$_3$ (48.0 grams, 572 mmoles), and Pd(PPh$_3$)$_4$ (3.3 grams, 2.86 mmoles). Water (300 mL) and dimethoxyethane (300 mL) were added, and the mixture was heated slowly to 83° C. (internal temperature) over a 1 hour period with overhead stirring. After ~2 hours all solids had dissolved. The reaction was allowed to stir for 10 hours. The mixture was cooled to room temperature and stirred overnight after which time a thick gum had formed. The crude mixture was diluted with water (2 L) and stirred for an additional 2 hours. The mixture was then allowed to rest without stirring until the gum had settled to the bottom of the flask. The liquid phase was removed via vacuum, then replaced with 0.1N NaOH and stirred for 15 minutes. The gum was allowed to settle and the liquid removed via vacuum. The gum was then similarly washed three times with water, then transferred to a 1 neck flask as an acetone solution. The mixture was concentrated in vacuo and azeotroped five times with ethyl acetate.

Example 7

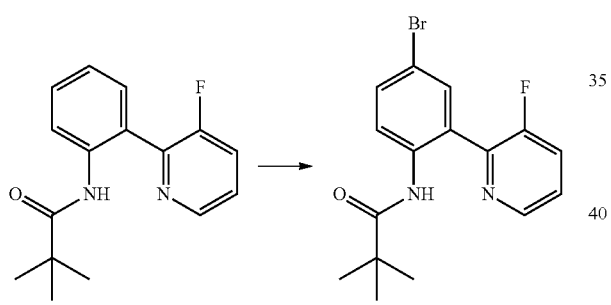

N-[4-Bromo-2-(3-fluoro-pyridin-2-yl)-phenyl]-2,2-dimethyl-propionamide

To a room temperature suspension of N-[2-(3-fluoro-pyridin-2-yl)-phenyl]-2,2-dimethyl-propionamide (~77 mmoles) in acetic acid (300 mL) was added bromine (12 mL, 228 mmoles) as a solution in 50 mL of acetic acid over a 1 hour period. The heterogeneous mixture was stirred at room temperature for 5 hours over which time a thick precipitate formed. The mixture was then poured over ice, diluted with 1N Na$_2$S$_2$O$_3$ (500 mL), and stirred for 1 hour. The solids were filtered, re-suspended in water (2 L), stirred for 1 hour, then filtered and washed with water again. The resulting solids were pumped to dryness at 50° C., re-suspended in HOAc (400 mL), and treated with bromine (4 mL, 76 mmoles) in acetic acid solution (20 mL) over a 20 minute period. The resulting heterogeneous mixture was stirred for 5 hours, then quenched and treated as described above. The resulting solids were vacuum dried at 50° C. to afford the title compound (19.1 grams, 72%) as a tan powder.

Example 8

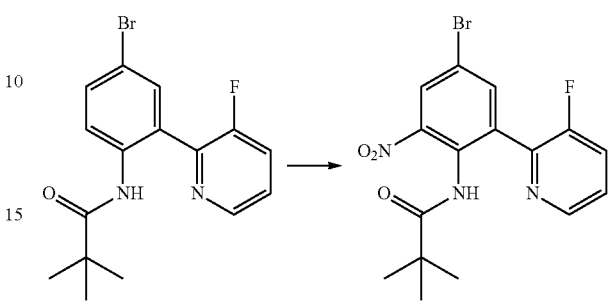

N-[4-Bromo-2-(3-fluoro-pyridin-2-yl)-6-nitro-phenyl]-2,2-dimethyl-propionamide To a suspension of N[4-bromo-2-(3-fluoro-pyridin-2-yl)-phenyl]-2,2-dimethyl-propionamide (6.45 grams, 18.4 mmoles) in TFA (100 mL) and TFAA (25.5 mL, 183.6 mmole), at 0° C., was added a TFA solution (30 mL) of 90% fuming nitric acid (2.46 mL, 55.1 mmoles) over a 45 minute period. The mixture was then stirred at 0° C. for a total of 4 hours. The crude reaction (now homogenous) was poured into ice producing a pasty mass. The mixture was diluted to 500 mL total volume with water, treated with 50 mL of methanol, and vigorously stirred for 12 hours. The resulting solids were filtered, washed with copious amounts of water, then dried in vacuo at 50° C. to afford the title compound (6.1 grams, 82% yield) as a tan powder.

Example 9

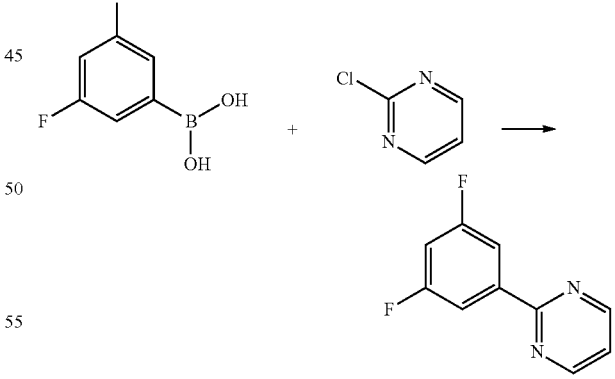

2-(3,5-Difluoro-phenyl)-pyrimidine

A solution of the difluoroboronic acid (5.4 g, 34.1 mmoles) and 2-chloropyrimidine (3.0 g, 26.2 mmoles) in ethanol (50 mL) was treated with Na$_2$CO$_3$ (3.6 g, 34.1 mmoles) and Pd(PPh$_3$)$_4$ (1.5 g, 1.31 mmoles) then heated at reflux for 3 days. The resulting mixture was then diluted with EtOAc, Silica gel added, and the resulting slurry stirred for 3 hours at room temperature. The crude mixture was then filtered through a silica gel pad with EtOAc, concentrated in vacuo, and flash chromatographed (silica gel, 19/1-14/1-9/1-7/1 hexanes/EtOAc gradient) to afford the title compound (1.38 g, 27%) as a white solid. $^1$H NMR (dmso-d$_6$, 500 MHz): 8.95 (d, 2H); 7.98 (m, 2H); 7.57 (dd, 1H); 7.48 (m, 1H).

Example 10

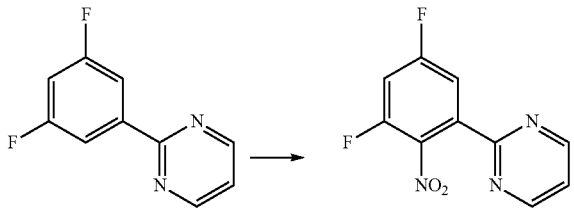 [SMILES: Fc1cc(F)cc(-c2ncccn2)c1 ; O=[N+]([O-])c1c(F)cc(F)cc1-c1ncccn1]

2-(3,5-Difluoro-2-nitro-phenyl)-pyrimidine

To a room temperature solution of 2-(3,5-difluoro-phenyl)-pyrimidine (1.2 g, 6.24 mmole) in H$_2$SO$_4$ (3 mL) was added 90% HNO$_3$ (0.375 mL, 9.37 mmoles) over 10 seconds via syringe. The resulting mixture was stirred at room temperature for 1 hour then poured into ice. The resulting heterogeneous mixture was then diluted with water, warmed to room temperature, and filtered. The solids were washed with water and dried in vacuo to afford the title compound (1.53 g, 100%) as a tan solid. $^1$H NMR (dmso-d$_6$, 500 MHz): 8.92 (d, 2H); 8.67 (m, 1H); 7.94 (m, 1H); 7.65 (dd, 1H).

Example 11

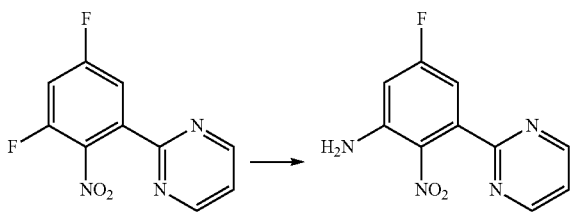 [SMILES: O=[N+]([O-])c1c(F)cc(F)cc1-c1ncccn1 ; Nc1cc(F)cc(-c2ncccn2)c1[N+](=O)[O-]]

5-Fluoro-2-nitro-3-pyrimidin-2-yl-phenylamine

To a solution of 2-(3,5-difluoro-2-nitro-phenyl)-pyrimidine (1.5 g, 6.32 mmoles) in dioxane (10 mL) was added tBuNH$_2$ (6.6 mL, 63.24 mmoles) at room temperature. The mixture was heated to 100° C. in a sealed tube for 10 hours. The mixture was then cooled to room temperature, poured into water, and the solids stirred for 1 hour. The mixture was filtered, solids washed with water until filtrate was clear. The crude product was then diluted in MeOH, 6N HCl added, and the resulting mixture heated at reflux for 3 hours. The reaction was cooled to room temperature and poured into ice. The resulting heterogeneous mixture was warmed to room temperature, filtered, solids washed with water until filtrate ran clear, and dried in vacuo to afford the title compound (1.33 g, 90%) as an orange powder. $^1$H NMR (dmso-d$_6$, 500 MHz): 8.87 (d, 2H); 7.52 (dd, 1H); 7.08 (dd, 1H); 6.86 (dd, 1H); 6.60 (s, 2H).

Example 12

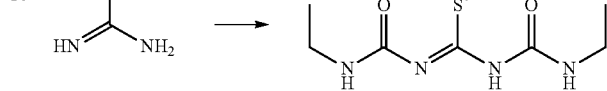

N,N-Diethlyureamido-2-methyl-2-thiopseudourea

To a mixture of 2-methyl-2-thiopseudourea sulfate (2.0 g, 7.18 mmol) in water (3 mL) was added ethyl isocyanate (1.137 mL, 14.37 mmol) followed by dropwise 6N NaOH to a stable pH 8. After 1 hour at pH8 the biphasic solution was diluted with aqueous saturated sodium bicarbonate and extracted into ethyl acetate (3×100 mL). The combined organic layers were washed with brine and dried over sodium sulfate, filtered then concentrated in vacuo to afford the title compound as a pungent oil (1.54 g, 92.7%). TLC (50% Ethyl acetate/methylene chloride) and $^1$H NMR suggests that the material is a mixture of mono and diacyl pseudourea. $^1$H NMR (500 Mhz, CDCl$_3$) ∂1.18(m2, 6H), 2.31 and 2.41 (2 s, 3H), 3.28 (m, 4H).

Example 13

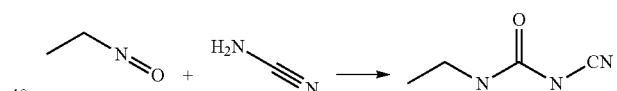

N'-Ethyl-N-cyanourea

To a 20° C. solution of sodium hydroxide (1.5 M aqueous, 50 mL, 75.02 mmol) was added cyanamide (8.5 g, 202.25 mmol) then ethyl isocyanate (4 mL, 50.56 mmol) was added in a dropwise fashion over 10 minutes. After stirring for 30 minutes, additional sodium hydroxide (3M, 25 mL. 75.02 mmol) and ethyl isocyanate (4 mL, 50.56 mmol) were added. The resulting solution was then aged for a minimum of 30 minutes before using directly without isolation.

Example 14

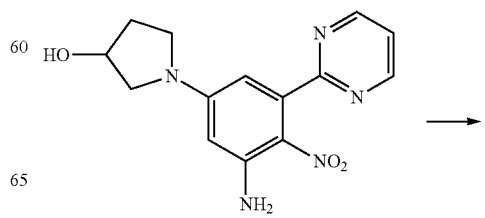

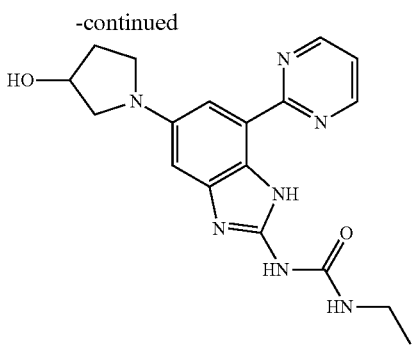

1-Ethyl-3-(5-(3-hydroxypyrrolidin-1-yl)-7-(pyrimidin-2-yl)-1H-benzo[d]imidazol-2-yl)urea (compound I-12)

A suspension of 1-(3-amino-4-nitro-5-(pyrimidin-2-yl)phenyl)pyrrolidin-3-ol (400 mg, 1.33 mmol) and 10% palladium on carbon (100 mg) in ethyl acetate/methanol (20 mL+5 mL) was placed in a Parr hydrogenator under a hydrogen pressure of 45 psi. The mixture was shaken for 2 hours, filtered, and the filtrate concentrated in vacuo. The resulting residue was diluted with buffer (15 ml pH=3.5), and 19a (2.96 mL, 1M) was added. The mixture was heated at 95° C. for 3 hours. The mixture was dilute with water, basified with sat. NaHCO$_3$. The solid was collected, washed with water, and dried in vacuo to afford 100 mg compound I-12. $^1$H NMR+LC/MS were consistent with the desired structure (see Table 3 infra).

Example 15

We have prepared other compounds of formula I by methods substantially similar to those described in Schemes 1 through 23, Examples 1 through 14, and by methods known in the art. The characterization data for these compounds is summarized in Table 3 below and includes LC/MS (observed) and $^1$H NMR data.

Mass Spec. samples were analyzed on a Micro Mass ZQ, ZMD, Quattro LC, or Quattro II mass spectrometer operated in single MS mode with electro spray ionization. Samples were introduced into the mass spectrometer using flow injection. (FIA) or chromatography. Mobile phase for all mass spec. analysis consisted of acetonitrile-water mixtures with 0.2% formic acid as a modifier. Method A consisted of a 5-45% CH$_3$CN (0.2% formic acid)/H$_2$O (0.2% formic acid) gradient. Method B consisted of a 10-60% CH$_3$CN (0.2% formic acid)/H$_2$O (0.2% formic acid) gradient. Method C consisted of a 10-90% CH$_3$CN (0.2% formic acid)/H$_2$O (0.2% formic acid) gradient.

HPLC method A utilized to obtain the reported retention time is as follows:
Column: YMC Pro C18 column, 4.6×50 mm
Linear Gradient: 10% CH$_3$CN—H$_2$O to 90% CH$_3$CN—H$_2$O over 3 minutes with 5 minutes run time (0.2% formic acid)
Flow Rate: 1.5 ml/min
Detection: Diode Array HPLC method B or C utilized to obtain the reported retention time is as follows:
Column: YMC Pro C18 column, 2.0×50 mm
Linear Gradient: 5% CH$_3$CN—H$_2$O to 45% CH$_3$CN—H$_2$O for method B or 10% CH$_3$CN—H$_2$O to 60% CH$_3$CN—H$_2$O for method C over 5 minutes with 7 minutes run time (0.2% formic acid)
Flow Rate: 1.5 ml/min
Detection: Diode Array As used herein, the term "Rt(min)" refers to the HPLC retention time, in minutes, associated with the compound.

$^1$H NMR spectra were recorded at 500 MHz using a Bruker AMX 500 instrument. $^1$H NMR data was found to be consistent in each case with the compound structure.

TABLE 3

Example 16
Characterization Data For Selected Compounds of Formula I

| Compound No. I- | LC/MS, R$_t$ (min). Method A, B, C, or FIA | M + 1 (obs) | $^1$H NMR |
|---|---|---|---|
| 1 | 196 (C) | 300.9 | (CD$_3$OD): 8.5 (s, 1H), 7.9 (s, 1H), 7.3 (s, 1H), 7.0 (s, 1H), 6.6 (d, 1H), 3.9 (s, 3H), 3.3 (q, 2H), 1.2 (t, 3H) ppm. |
| 2 | 6.68 (A) | 343.9 | (CD$_3$OD): 8.88 (s, IH), 8.70 (br s, 1H), 8.33 (s, 1H), 7.87 (dd, 1H), 7.58 (m, 1H), 3.37 (q, 2H), 1.25 (t, 3H) ppm. |
| 3 | 6.32 (A) | 357.1 | (CD$_3$OD): 1.13 (t, 3H), 1.3 (t, 3H) 3.24 (q, 2H), 3.37 (q, 2H), 7.82 (s, 1H), 7.82 (s, 1H), 7.96 (t, 1H), 8.19 (s, 1H), 8.56 (s, 1H), 8.62 (d, 1H), 8.82 (d, 1H), 9.15 (s, 1H), 11.02(s, 1H) |
| 4 | 6.32 (A) | 324.9 | (CD$_3$OD): 8.73 (br s, 1H), 8.42 (s, 1H), 8.06 (s, 1H), 7.89 (dd, 1H), 7.62 (ddd, 1H), 3.37 (q, 2H), 1.24 (t, 3H) ppm. |
| 5 | 1.83 (C) | 409.2 | (DMSO-d6): 1.15 (t, 3H), 2.07 (s, 3H), 3.16-3.21 (m, 2H), 3.22-3.29 (m. 4H), 3.64-3.69 (m, 4H), 7.32-7.35 (m, 1H), 7.56 (t, 1H), 7.82-7.88 (m, 1H), 8.06-8.09 (m, 1H), 9.03 (d, 2) ppm. |
| 6 | 196 (C) | 366.1 | (DMSO-d6): 1.15 (t, 3H), 2.09-2.17 (m, 2H), 2.34 (s, 3H), 2.56 (t, 2H), 3.23-3.30 (m, 2H), 3-97 (t, 2H), 7.56 (t, 1H), 7.76 (s, br., 1H), 8.15 (s, 1H), 8.55 (s, 1H), 9.05 (d, 2) ppm. |
| 7 | 7.64 (A) | 358.1 | (CD$_3$OD): 8.88 (s, 1H), 8.71 (d, 1H), 8.34 (s, 1H), 7.89 (dd, 1H), 7.60(ddd, 1H), 4.00(s, 3H), 3.38 (q, 2H), 1.24 (t, 3H) ppm. |
| 8 | 5.03 (B) | 411.2 | (CD$_3$OD): 8.58 (d, 1H), 8.16 (s, 1H), 7.77 (dd, 1H), 7.70 (s, 1H), 7.49 (m, 1H), 6.48 (s, 1H), 3.36 (q, 2H), 3.16 (s, 3H), 3.08 (s, 3H), 2.28 (s, 3H), 1.25 (t, 3H) ppm. |
| 9 | 4.68 (B) | 399.2 | (CD$_3$OD): 9.17-7.49 (m, 5H), 3.49 (m, 1H), 3.31 (m, 2H), 2.70-2.51 (m, 5H), 1.54-1.18(m, 6H) ppm. |

TABLE 3-continued

Example 16
Characterization Data For Selected Compounds of Formula I

| Compound No. I- | LC/MS, $R_t$ (min). Method A, B, C, or FIA | M + 1 (obs) | $^1$H NMR |
|---|---|---|---|
| 10 | 4.80 (B) | 397.2 | (CD$_3$OD): 8.54 (s, 1H), 8.02 (s, 1H), 7.72 (dd, 1H), 7.58 (s, 1H), 7.46 (s, 1H), 6.22 (s, 1H), 3.32 (q, 2H), 2.84 (s, 3H), 2.81 (s, 3H), 2.49 (s, 3H), 1.24 (t, 3H) ppm. |
| — | — | — | — |
| 12 | 1.9 (C) | 368 | (CD$_3$OD): 8.95 (d, 2H), 7.79 (d, 1H), 7.44 (t, 1H), 6.83 (d, 1H), 4.61 (t, 1H), 3.61 (m, 2H), 3.47 (m, 1H), 3.33 (m, 3H), 2.24 (m, 1H), 2.12 (m, 1H), 1.24 (t, 3H) ppm. |
| 13 | 2.0 (C) | 411 | (CD$_3$OD): 8.70 (d, 1H), 8.04 (s, 1H), 7.86 (dd, 1H), 7.63 (s, 1H), 7.57 (m, 1H), 3.48-3.13 (m, 5H), 3.03 (s, 3H), 2.75 (m, 1H), 2.60(m, 1H), 2.18 (m, 2H), 1.23 (t, 3H) ppm. |
| 14 | 2.20 (A) | 389 | (DMSO-d6): 12.52 (s, 1H); 11.05 (s, 1H); 9.01 (d, 2H); 8.67 (d, 1H); 8.02 (m, 1H); 7.86 (m,1H); 7.84 (d, 1H); 7.62 (m, 1H); 7.54 (t, 1H); 7.49 (m, 1H); 6.90 (s, 1H); 4.61 (s, 2H); 3.24 (dq, 2H); 1.14 (t, 3H) ppm. |
| 15 | 2.23 (C) | 301 | (DMSO-d6): 12.02 (s, 1H); 9.97 (s, 1H); 9.03 (d, 2H); 7.89 (dd, 1H); 7.51 (t, 1H); 7.38 (dd, 1H); 7.25 (s, 1H): 3.25 (dq, 2H); 1.13 (t, 3H), ppm. |
| 16 | FIA | 314.1 | (CD$_3$OD): 1.22 (1, 3H), 3.35 (q, 2H), 6.70-6.75 (m, 1H), 7.87 (d, 1H). 7.98-8.02 (m, 1H), 8.44-8.48 (m, 1H) ppm. |
| 17 | 5.39 (C) | 458.2 | (CDCl$_3$): 8.20 (br s, 1H), 7.72 (s, 1H), 7.34-7.27 (m, 6H), 7.18 (br s, 1H), 6.44 (s, 1H), 4.76 (d, 1H), 4.55 (d, 1H), 3.36-3.19 (m, 4H), 2.95-2.91 (m, 2H), 2.71 (dd, 2H), 2.14 (br d, 2H), 2.02-1.95 (m, 2H), 1.19(t, 3H) ppm. |
| 18 | 5.48 (C) | 356.2 | (CD$_3$OD): 7.81 (s, 1H), 7.58 (s, 1H), 7.38-7.29 (m, 7H), 6.57 (t, 1H), 6.42 (s, 1H), 4.71 (s, 2H), 3.57 (t, 2H), 3.37-3.32 (q, 2H), 2.95 (t, 2H), 1.24 (t, 3H) |
| 19 | 4.86 (C) | 413.2 | (CD$_3$OD): 8.65 (s, 1H), 8.05 (s, 1H), 7.82 (dd, 1H), 7.59 (s, 1H), 7.52 (br s, 1H), 3-49 (m, 1H), 3.36 (q, 2H), 3.02 (s, 3H), 2.91-2.70 (m, 2H), 2.86 (s, 3H), 1.42 (d, 3H), 1.23 (t, 3H) ppm. |

DNA Gyrase ATPase Assay

The ATP hydrolysis activity of DNA gyrase was measured by coupling the production of ADP through pyruvate kinase/lactate dehydrogenase to the oxidation of NADH. This method has been described previously (Tamura and Gellert, 1990, *J. Biol. Chem.*, 265, 21342).

ATPase assays were carried out at 30° C. in buffered solutions containing 100 mM TRIS pH 7.6, 1.5 mM MgCl$_2$, 150 mM KCl. The coupling system contains (final concentrations) 2.5 mM phosphoenol pyruvate, 200 µM nicotinamide adenine dinucleotide (NADH), 1 mM DTT, 30 ug/ml pyruvate kinase, and 10 ug/ml lactate dehydrogenase. 40 nanomolar enzyme and a DMSO solution of the inhibitor to a final concentration of 4% was added and the reaction mixture was allowed to incubate for 10 minutes at 30° C. The reaction was then started by the addition of ATP to a final concentration of 0.9 mM and the rate of NADH disappearance at 340 nanometers was measured over the course of 10 minutes. The Ki values were determined from rate versus concentration profiles.

Compounds of the present invention were found to inhibit *E. coli* Gyrase. Table 4 shows the range of Ki inhibitory activity for selected compounds of this invention in the *E. coli* Gyrase ATPase assay. The compound numbers correspond to the compound numbers in Table 2. Compounds having an activity designated as "A" provided a Ki inhibition value equal to or above 0.100 micromolar. Compounds having an activity designated as "B" provided a Ki inhibition value between 0.050 micromolar and 0.100 micromolar. Compounds having an activity designated as "C" provided a Ki inhibition value equal to or below 0.050 micromolar. The term "ND" means no data.

TABLE 4

Example 17
*E. coli* Gyrase Ki Inhibition
Ranges of Selected Compounds

| No. I- | Activity |
|---|---|
| 1 | B |
| 2 | A |
| 3 | C |
| 4 | B |
| 5 | C |
| 6 | C |
| 7 | C |
| 8 | B |
| 9 | A |
| 10 | C |
| 11 | ND |
| — | — |
| 13 | C |
| 14 | B |
| 15 | C |
| 16 | C |
| 17 | A |
| 18 | C |
| 19 | A |

DNA Topo IV ATPase Assay:

The conversion of ATP to ADP by TopoIV enzyme was coupled to the conversion of NADH to NAD+ and measured by the change in absorbance at 340 nm. Topo4 was incubated with inhibitor (4% DMSO final) in buffer for 10 minutes at 30° C. Reaction was initiated with ATP and rates were monitored continuously for 20 minutes at 30° C. on a Molecular Devices SpectraMAX plate reader. The inhibition constant, Ki, was determined from plots of rate vs. [Inhibitor] fit to the Morrison Equation for tight binding inhibitors.

*S. aureus* TopoIV Buffer: 100 mM Tris 7.5, 2 mM MgCl$_2$, 200 mM K●Glutamate, 2.5 mM phosphoenol pyruvate, 0.2 mM NADH, 1 mM DTT, 4.25 µg/mL linearized DNA, 50 µg/mL BSA, 30 µg/mL pyruvate kinase, and 10 µg/mL lactate dehyrodgenase (LDH).

E. coli TopoIV Buffer: 100 mM Tris 7.5, 6 mM $MgCl_2$, 20 mM KCl, 2.5 mM phosphoenol pyruvate, 0.2 mM NADH, 10 mM DTT, 5.25 µg/mL linearized DNA, 50 µg/mL BSA, 30 µg/mL pyruvate kinase, and 10 µg/mL lactate dehyrogenase (LDH).

Compounds of the present invention were found to inhibit S. aureus TopoIV. Table 5 shows the range of Ki inhibitory activity for selected compounds of this invention in the S. aureus TopoIV inhibition assay. The compound numbers correspond to the compound numbers in Table 2. Compounds having an activity designated as "A" provided a Ki inhibition value equal to or above 0.500 micromolar. Compounds having an activity designated as "B" provided a Ki inhibition value between 0.250 micromolar and 0.500 micromolar. Compounds having an activity designated as "C" provided a Ki inhibition value equal to or below 0.250 micromolar. The term "ND" means no data.

TABLE 5

Example 18
S. aureus Topo IV Ki Inhibition
Ranges of Selected Compounds

| No. I- | Activity |
|---|---|
| 1 | ND |
| 2 | ND |
| 3 | ND |
| 4 | ND |
| 5 | ND |
| 6 | ND |
| 7 | ND |
| 8 | C |
| 9 | A |
| 10 | C |
| 11 | ND |
| 13 | C |
| 14 | A |
| 15 | A |
| 16 | A |
| 17 | C |
| 18 | C |
| 19 | A |

Susceptibility Testing in Liquid Media

Compounds of this invention were also tested for antimicrobial activity by susceptibility testing in liquid media. Such assays were performed within the guidelines of the latest NCCLS document governing such practices: "M7-A5 Methods for dilution Antimicrobial Susceptibility Tests for Bacteria that Grow Aerobically; Approved Standard—Fifth Edition (2000)". Other publications such as "Antibiotics in Laboratory Medicine" (Edited by V. Lorian, Publishers Williams and Wilkins, 1996) provide essential practical techniques in laboratory antibiotic testing. Essentially, several discrete bacterial colonies of Staphylococcus aureus, Streptococcus pneumoniae, Haemophilus influenzae, or Enterococcus faecalis (3 to 7) from a freshly streaked plate were transferred to an appropriate rich broth medium such as MHB, and supplemented where appropriate for the more fastidious organisms. This was grown overnight to high density followed by a 1 or 2-thousand-fold dilution to give an inoculation density of between $5 \times 10^5$ and $5 \times 10^6$ CFU per mL. Alternatively, the freshly picked colonies can be incubated at 37° C. for about 4 to 8 hours until the culture equals or exceeds a turbidity of a 0.5 McFarland standard (approximately $1.5 \times 10^8$ cells per mL) and diluted to give the same CFU per mL as above. In a more convenient method, the inoculum was prepared using a commercially available mechanical device (the BBL PROMPT System) that involves touching five colonies directly with a wand, containing cross-hatch grooves at its bottom, followed by suspension of the bacteria in an appropriate volume of saline. Dilution to the appropriate inoculum cell density was made from this cell suspension. The broth used for testing consists of MHB supplemented with 50 mg per L of $Ca^{2+}$ and 25 mg per L of $Mg^{2+}$. Standard dilution panels of control antibiotics were made and stored as in the NCCLS standard M7-A5, the dilution range typically being in the 128 µg per mL to 0.015 µs per mL (by 2-fold serial dilution). The test compounds were dissolved and diluted fresh for experimentation on the same day; the same or similar ranges of concentration as above being used. The test compounds and controls were dispensed into a multiwell plate and test bacteria added such that the final inoculation was approximately $5 \times 10^4$ CFU per well and the final volume was 100 µL. The plates were incubated at 35° C. overnight (16 to 20 hours) and checked by eye for turbidity or quantitated with a multiwell plate reader. The endpoint minimal inhibitory concentration (MIC) is the lowest concentration of drug at which the microorganism tested (Staphylococcus aureus, Streptococcus pneumoniae, Haemophilus influenzae, or Enterococcus faecalis) does not grow. Such determinations were also compared to the appropriate tables contained in the above two publications to ensure that the range of antibacterial activity is within the acceptable range for this standardized assay.

Compounds of the present invention were found to have antimicrobial activity in the above-described S. aureus, S. pneumoniae, H. influenzae, and E. faecalis MIC assays. Table 6 shows the results of these MIC assays for selected compounds of this invention. The compound numbers correspond to the compound numbers in Table 2. Compounds having an activity level designated as "C" provided an MIC of less than 1 µg/mL; compounds having an activity level designated as "B" provided an MIC of between 1 and 7 µg/mL; compounds having an activity level designated as "A" provided an MIC of greater than 7 µg/mL.

TABLE 6

S. aureus, S. pneumoniae, H. influenzae,
and E. faecalis MIC Ranges of Selected
Compounds

| No. Ia- | S. aureus | S. pneumoniae | H. influenzae | E. faecalis |
|---|---|---|---|---|
| 1 | A | B | A | A |
| 2 | A | A | A | A |
| 3 | A | C | A | C |
| 4 | A | C | A | B |
| 5 | A | C | A | B |
| 6 | A | C | A | B |
| 7 | A | B | A | B |
| 8 | A | C | A | B |
| 9 | A | B | A | A |
| 10 | A | C | A | C |
| 11 | A | B | A | B |
| 13 | B | C | A | C |
| 14 | A | C | A | B |
| 15 | A | B | A | B |
| 16 | A | B | A | A |
| 17 | B | C | A | B |

TABLE 6-continued

S. aureus, S. pneumoniae, H. influenzae, and E. faecalis MIC Ranges of Selected Compounds

| No. Ia- | S. aureus | S. pneumoniae | H. influenzae | E. faecalis |
|---|---|---|---|---|
| 18 | C | C | A | C |
| 19 | A | B | A | B |

While we have described a number of embodiments of the present invention, it is apparent that our basic constructions may be altered to provide other embodiments that utilize the products and processes of this invention.

We claim:
1. A compound of formula I:

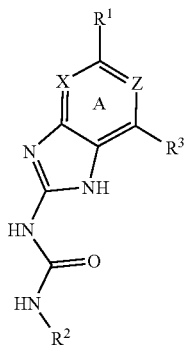

or a pharmaceutically acceptable salt thereof, wherein:
Z is selected from nitrogen or C—$R^4$;
X is selected from nitrogen or C—$R^4$;
$R^1$ is Q-Rx or $R^Y$; wherein
  Q is a $C_1$-$C_6$ aliphatic wherein up to three methylene units of Q are optionally and independently replaced by —NH—, —NR—, —O—, —S—, —$CO_2$—, —OC(O)—, —C(O)CO—, —C(O)—, —C(S)—, —C(O)NH—, —C(O)NR—, —C(=N—CN), —NHCO—, —NRCO—, —NHC(O)O—, —NRC(O)O—, —$SO_2$NH—, —$SO_2$NR—, —NHSO$_2$—, —NRSO$_2$—, —NHC(O)NH—, —NRC(O)NH—, —NHC(O)NR—, —NRC(O)NR, —OC(O)NH—, —OC(O)NR—, —NHSO$_2$NH—, —NRSO$_2$NH—, —NHSO$_2$NR—, —NRSO$_2$NR—, —SO— or —$SO_2$—; wherein
  Q is optionally substituted with 1-3 independent occurrences of RQ;
  R is selected from $C_{1-6}$ aliphatic, $C_{3-10}$ cycloaliphatic, $C_{3-10}$ cycloaliphatic, or a 3-8 membered saturated or partially unsaturated monocyclic ring, or a 5-6 membered monocyclic aryl ring; each ring having 0-3 heteroatoms independently selected from nitrogen, oxygen, or sulfur; or an 8-12 membered saturated, partially unsaturated, or fully unsaturated bicyclic ring system having 0-5 heteroatoms independently selected from nitrogen, oxygen, or sulfur; wherein said monocyclic or bicyclic ring is optionally substituted with 1-3 independent occurrences of $R^T$, -T-$Ar^1$, halogen, oxo, thioxo, —$OR^T$, —$SR^T$, —N($R^T$)$_2$, —$NO_2$, —$C_{1-4}$haloalkyl, —$C_{1-4}$haloalkoxy, —CN, —$CO_2R^T$, —$COR^T$, —$CON(R^T)_2$, —$OCOR^T$, —$NR^TCOR^T$, —$SO_2R^T$, —$SO_2N(R^T)_2$, or —$NR^TSO_2R^T$; wherein each $R^T$ is independently hydrogen or unsubstituted $C_{1-6}$ aliphatic; or
any two $R^T$ or two R groups, on the same substituent or different substituents, together with the atom(s) to which each group is bound, optionally form a 3-8 membered saturated or partially unsaturated monocyclic ring, or a 5-6 membered monocyclic aryl ring having 0-3 heteroatoms independently selected from nitrogen, oxygen, or sulfur; wherein said monocyclic ring is optionally substituted with 1-3 independent occurrences of $R^R$, -T-$Ar^1$, halogen, oxo, thioxo, —$OR^R$, —$SR^R$, —$N(R^R)_2$, —$NO_2$, —$C_{1-4}$haloalkyl, —$C_{1-4}$haloalkoxy, —CN, —$CO_2R^R$, —$COR^R$, —$CON(R^R)_2$, —$OCOR^R$, —$NR^RCOR^R$, —$SO_2R^R$, —$SO_2N(R^R)_2$, or —$NR^RSO_2R^R$; wherein
  each $R^R$ is independently hydrogen or unsubstituted $C_{1-6}$ aliphatic;
T is $(CH_2)_y$;
y is 0, 1, or 2;
$Ar^1$ is selected from:
(a) a 3-8 membered saturated or partially unsaturated ring;
(b) a 5-6 membered aryl ring;
(c) a 3-7 membered heterocyclic ring having 1-3 heteroatoms independently selected from nitrogen, oxygen, or sulfur;
(d) a 5-6 membered heteroaryl ring having 1-4 heteroatoms independently selected from nitrogen, oxygen, or sulfur; or
(e) an 8-12 membered saturated, partially unsaturated, or fully unsaturated bicyclic ring system having 0-5 heteroatoms independently selected from nitrogen, oxygen, or sulfur; wherein
$Ar^1$ is optionally substituted with 1-3 independent occurrences of —$R^W$, oxo, thioxo, —$CO_2R^W$, —$OR^W$, —$N(R^W)_2$, —$SR^W$, —$NO_2$, halogen, —CN, —$C_{1-4}$haloalkyl, —$C_{1-4}$haloalkoxy, —$C(O)N(R^W)_2$, —$NR^WC(O)R^W$, —$SO_2R^W$, —$SO_2N(R^W)_2$, —$NR^WSO_2R^W$, —$NR^WCON(R^W)_2$, —$NR^WCO_2R^W$, —$COR^W$, —$OCOR^W$, —$OCON(R^W)_2$, —$SOR^W$, —$NR^WSO_2N(R^W)_2$, —$COCOR^W$, —$COCH_2COR^W$, —OP(O)($OR^W)_2$, —P(O)($OR^W)_2$, —OP(O)$_2OR^W$, —P(O)$_2OR^W$, —PO($R^W)_2$, or —OPO($R^W)_2$;
each occurrence of $R^W$ is independently selected from hydrogen, $C_{1-6}$ aliphatic, a 3-8 membered saturated or partially unsaturated monocyclic ring, or a 5-6 membered monocyclic aryl ring; each ring having 0-4 heteroatoms independently selected from nitrogen, oxygen, or sulfur; wherein said $C_{1-6}$ aliphatic, said 3-8 membered or 5-7 membered monocyclic ring is optionally substituted with 1-3 independent occurrences of $R^S$, -T-$Ar^3$, halogen, oxo, thioxo, —$OR^S$, —$SR^S$, —$N(R^S)_2$, —$NO_2$, —$C_{1-4}$haloalkyl, —$C_{1-4}$haloalkoxy, —CN, —$CO_2R^S$, —$COR^S$, —$CONHR^S$, —$OCOR^S$, —$NR^S$-$COR^S$, —$SO_2R^S$, —$SO_2N(R^S)_2$, or —$NR^SSO_2R^S$; wherein
$R^S$ is hydrogen or unsubstituted $C_{1-6}$ aliphatic; and
$Ar^3$ is selected from:
(a) a 3-8 membered saturated or partially unsaturated ring;
(b) a 5-6 membered aryl ring;
(c) a 3-7 membered heterocyclic ring having 1-3 heteroatoms independently selected from nitrogen, oxygen, or sulfur; or
(d) a 5-6 membered heteroaryl ring having 1-4 heteroatoms independently selected from nitrogen, oxygen, or sulfur; or (e) an 8-12 membered saturated, partially unsaturated, or fully unsaturated bicyclic ring system having 0-5 heteroatoms independently selected from nitrogen, oxygen, or sulfur; wherein $Ar^3$ is optionally substituted with 1-3 independent occurrences of —$R^J$, oxo, thioxo, —$CO_2R^J$, —$OR^J$, —$N(R^J)_2$, —$SR^J$, —$NO_2$, halogen, —CN, —$C_{1-4}$haloalkyl, —$C_{1-4}$haloalkoxy, —C(O)N($R^J)_2$, —$NR^JC(O)R^J$, —$SO_2R^J$, —$SO_2N(R^J)_2$, —$NR^JSO_2R^J$, —$NR^JCON(R^J)_2$, —$NR^JCO_2R^J$, —$COR^J$, —$OCOR^J$, —$OCON(R^J)_2$, —$SOR^J$, —$NR^JSO_2N(R^J)_2$, —$COCOR^J$, —$COCH_2COR^J$, —$OP(O)(OR^J)_2$, —$P(O)(OR^J)_2$, —$OP(O)_2OR^J$, —$P(O)_2OR^J$, —$PO(R^J)_2$, or —$OPO(R^J)_2$;

each occurrence of $R^J$ is independently selected from hydrogen, $C_{1-6}$ aliphatic, a 3-8 membered saturated or partially unsaturated monocyclic ring, or a 5-6 membered monocyclic aryl ring; each ring having 0-4 heteroatoms independently selected from nitrogen, oxygen, or sulfur; wherein said $C_{1-6}$ aliphatic, said 3-8 membered or 5-6 membered monocyclic ring is optionally substituted with 1-3 independent occurrences of $R^I$, halogen, oxo, thioxo, —$OR^I$, —$SR^I$, —$N(R^I)_2$, —$NO_2$, —$C_{1-4}$haloalkyl, —$C_{1-4}$haloalkoxy, —CN, —$CO_2R^I$, —$COR^I$, —$CONHR^I$, —$OCOR^I$, —$NR^ICOR^I$, —$SO_2R^I$, —$SO_2N(R^I)_2$, or —$NR^ISO_2R^I$; wherein $R^I$ is hydrogen or unsubstituted $C_{1-6}$ aliphatic;

$R^Q$ is selected from halogen, L, -($L_n$)—$R^S$, -($L_n$)—$N(R^S)_2$, -($L_n$)—$SR^S$, -($L_n$)—$OR^S$, -($L_n$)—($C_{3-10}$ cycloaliphatic), -($L_n$)—($C_{6-10}$ aryl), -($L_n$)-(5-10 membered heteroaryl), -($L_n$)-(5-10 membered heterocyclyl), oxo, thioxo, —$C_{1-4}$ haloalkoxy, —$C_{1-4}$haloalkyl, -($L_n$)—$NO_2$, -($L_n$)—CN, -($L_n$)—$CF_3$, -($L_n$)—$OCF_3$, —$CO_2R^S$, —$COR^S$, —$OC(O)R^S$ or —$NR^SC(O)R^S$; wherein n is 0 or 1; or any two $R^Q$ or two $R^S$ groups, or any combination of an $R^Q$ group with an R or $R^S$ group on the same substituent or different substituents, together with the atom(s) to which each group is bound, optionally form a 3-8 membered saturated or partially unsaturated monocyclic ring, or a 5-6 membered monocyclic aryl ring; each ring having 0-3 heteroatoms independently selected from nitrogen, oxygen, or sulfur; wherein any of said monocyclic ring is optionally substituted with 1-3 independent occurrences of $R^O$, -T-$Ar^3$, halogen, oxo, thioxo, —$OR^O$, —$SR^I$, —$N(R^O)_2$, —$NO_2$, —$C_{1-4}$haloalkyl, —$C_{1-4}$haloalkoxy, —CN, —$CO_2R^O$, —$COR^O$, —$CON(R^O)_2$, —$OCOR^O$, —$NR^OCOR^O$, —$SO_2R^O$, —$SO_2N(R^O)_2$, or —$NR^OSO_2R^O$; wherein $R^O$ is hydrogen or unsubstituted $C_{1-6}$ aliphatic;

L is $C_{1-6}$ aliphatic wherein up to three methylene units are replaced by —NH—, —$NR^5$—, —O—, —S—, —$CO_2$—, —OC(O)—, —C(O)CO—, —C(O)—, —C(S)—, —C(O)NH—, —C(O)$NR^5$—, —C(=N—CN), —NHCO—, —$NR^5$CO—, —NHC(O)O—, —$NR^5$C(O)O—, —$SO_2$NH—, —$SO_2NR^5$—, —$NHSO_2$—, —$NR^5SO_2$—, —NHC(O)NH—, —$NR^5$C(O)NH—, —NHC(O)$NR^5$—, —$NR^5$C(O)$NR^5$, —OC(O)NH—, —OC(O)$NR^5$—, —$NHSO_2$NH—, —$NR^5SO_2$NH—, —$NHSO_2NR^5$—, —$NR^5SO_2NR^5$—, —SO— or —$SO_2$—; wherein $R^5$ is selected from $C_{1-6}$ aliphatic, $C_{3-10}$ cycloaliphatic, or a 3-8-membered saturated or partially unsaturated monocyclic ring, or a 5-6 membered aryl ring; each ring having 0-3 heteroatoms independently selected from nitrogen, oxygen, or sulfur; or an 8-12 membered saturated, partially unsaturated, or fully unsaturated bicyclic ring system having 0-5 heteroatoms independently selected from nitrogen, oxygen, or sulfur; wherein each of said rings is optionally substituted with 1-3 independent occurrences of $R^N$, -T-$Ar^3$, halogen, oxo, —$OR^N$, —$SR^N$, —$N(R^N)_2$, —$NO_2$, —$C_{1-4}$haloalkyl, —$C_{1-4}$haloalkoxy, —CN, —$CO_2R^N$, —$COR^N$, —$CON(R^N)_2$, —$OCOR^N$, —$NR^NCOR^N$, —$SO_2R^N$, —$SO_2N(R^N)_2$, or —$NR^NSO_2R^N$, wherein;

$R^N$ is hydrogen or unsubstituted $C_{1-6}$ aliphatic; or any two $R^5$ groups, on the same substituent or different substituents, together with the atom(s) to which each $R^5$ group is bound, optionally form a 3-8-membered saturated or partially unsaturated monocyclic ring, or a 5-6 membered aryl ring having 0-3 heteroatoms independently selected from nitrogen, oxygen, or sulfur; wherein said ring is optionally substituted with 1-3 independent occurrences of $R^M$, -T-$Ar^3$, halogen, oxo, thioxo, —$OR^M$, —$SR^M$, —$N(R^M)_2$, —$NO_2$, —$C_{1-4}$haloalkyl, —$C_{1-4}$haloalkoxy, —CN, —$CO_2R^M$, —$COR^M$, —$CON(R^M)_2$, —$OCOR^M$, —$NR^MCOR^M$, —$SO_2R^M$, —$SO_2N(R^M)_2$, or —$NR^MSO_2R^M$; wherein, $R^M$ is hydrogen or unsubstituted $C_{1-6}$ aliphatic;

$R^X$ is selected from —R', halogen, =NR', —$NO_2$, —CN, —$C_{1-4}$haloalkyl, —$C_{1-4}$haloalkoxy, —OR', —SR', —N(R')$_2$, —NR'COR', —NR'CON(R')$_2$, —NR'$CO_2$R', —COR', —$CO_2$R', —OCOR', —CON(R')$_2$, —OCON(R')$_2$, —SOR', —$SO_2$R', —$SO_2$N(R')$_2$, —NR'$SO_2$R', —NR'$SO_2$N(R')$_2$, —COCOR', —$COCH_2$COR', —OP(O)(OR')$_2$, —P(O)(OR')$_2$, —OP(O)$_2$OR', —P(O)$_2$OR', —PO(R')$_2$, or —OPO(R')$_2$; wherein each occurrence of R' is independently hydrogen, $C_{1-6}$ aliphatic, $C_{3-10}$ cycloaliphatic, or a 3-8-membered saturated or partially unsaturated monocyclic ring or a 5-6 membered aryl ring having 0-3 heteroatoms independently selected from nitrogen, oxygen, or sulfur; or an 8-12 membered saturated, partially unsaturated, or fully unsaturated bicyclic ring system having 0-5 heteroatoms independently selected from nitrogen, oxygen, or sulfur; wherein each of said rings is optionally substituted with 1-3 independent occurrences of —$R^W$, -T-$Ar^1$, oxo, thioxo, —$CO_2R^W$, —$OR^W$, —$N(R^W)_2$, —$SR^W$, —$NO_2$, —$C_{1-4}$haloalkyl, —$C_{1-4}$haloalkoxy, halogen, —CN, —C(O)N($R^W)_2$, —$NR^WC(O)R^W$, —$SO_2R^W$, —$SO_2N(R^W)_2$, —$NR^WSO_2R^W$, —$NR^WCON(R^W)_2$, —$NR^WCO_2R^W$, —$COR^W$, —$OCOR^W$, —$OCON(R^W)_2$, —$SOR^W$, —$NR^WSO_2N(R^W)_2$, —$COCOR^W$, —$COCH_2COR^W$, —$OP(O)(OR^W)_2$, —$P(O)(OR^W)_2$, —$OP(O)_2OR^W$, —$P(O)_2OR^W$, —$PO(R^W)_2$, or —$OPO(R^W)_2$; or two occurrences of $R^W$, two occurrences of R', or one $R^W$ and one R' are taken together with the atom(s) to which they are bound to optionally form a 3-8-membered saturated or partially unsaturated monocyclic ring or a 5-6 membered aryl ring having 0-3 heteroatoms independently selected from nitrogen, oxygen, or sulfur; or an 8-12 membered saturated, partially unsaturated, or fully unsaturated bicyclic ring system having 0-5 heteroatoms independently selected from nitrogen, oxygen, or sulfur; wherein said monocyclic or bicyclic ring is optionally substituted with 1-3 independent occurrences of $R^T$, -T-$Ar^3$, halogen, oxo, thioxo, —$OR^T$, —$SR^T$, —$N(R^T)_2$, —$NO_2$, —$C_{1-4}$haloalkyl, —$C_{1-4}$haloalkoxy, —CN, —$CO_2R^T$, —$COR^T$, —$CON(R^T)_2$, —$OCOR^T$, —$NR^TCOR^T$, —$SO_2R^T$, —$SO_2N(R^T)_2$, or —$NR^TSO_2R^T$;

$R^Y$ is selected from —$R^K$, halogen, —$NO_2$, —CN, —$C_{1-4}$haloalkyl, —$C_{1-4}$haloalkoxy, —OR', —SR', —N(R')$_2$, —NR'COR', —NR'CON(R')$_2$, —NR'$CO_2$R', —COR', —CO₂R', —OCOR', —CON(R)₂, —OCON(R')₂, —C(R)=NOR', —C(R')=NOH, —C(R)=NR', —C(R)=N—N(R)₂, —SOR', —SO₂R', —SO₂N(R)₂, —NR'SO₂R', —NR'SO₂N(R')₂, —COLOR', —COCH₂COR', —C(O)C(O)N(R'²)R'—OP(O)(OR')₂, —P(O)(OR')₂, —OP(O)₂OR', —P(O)₂OR', —PO(R')₂, or —OPO(R)₂;

$R^K$ is selected from hydrogen, $C_{1-6}$ aliphatic, $C_{3-10}$ cycloaliphatic, or a 3-8-membered saturated, or partially unsaturated monocyclic ring having 0-3 heteroatoms independently selected from nitrogen, oxygen, or sulfur; or an 8-12 membered saturated or partially unsaturated bicyclic ring system having 0-5 heteroatoms independently selected from nitrogen, oxygen, or sulfur, wherein said $C_{1-6}$ aliphatic, $C_{3-10}$ cycloaliphatic, or said monocyclic or bicyclic ring is optionally substituted with 1-4 independent occurrences of —$R^W$, -T-Ar¹, oxo, thioxo, —CO₂$R^W$, —O$R^W$, —N($R^W$)₂, —S$R^W$, —NO₂, —$C_{1-4}$haloalkyl, —$C_{1-4}$haloalkoxy, halogen, —CN, —C(O)N($R^W$)₂, —N$R^W$C(O)$R^W$, —SO₂$R^W$, —SO₂N($R^W$)₂, —N$R^W$SO₂$R^W$, —N$R^W$CON($R^W$)₂, —N$R^W$CO₂$R^W$, —CO$R^W$, —OCO$R^W$, —OCON($R^W$)₂, —SO$R^W$, —N$R^W$SO₂N($R^W$)₂, —COCO$R^W$, —COCH₂CO$R^W$, —OP(O)(O$R^W$)₂, —P(O)(O$R^W$)₂, —OP(O)₂O$R^W$, —P(O)₂O$R^W$, —PO($R^W$)₂, or —OPO($R^W$)₂;

wherein any nitrogen atom in any of said rings is optionally substituted with —R⁺, —N(R⁺)₂, —COR⁺, —CO₂R⁺, —COCOR⁺, —COCH₂COR⁺, —SO₂R⁺, —SO₂N(R⁺)₂, —C(=S)N(R⁺)₂, —C(=NH)—N(R⁺)₂, or —NR⁺SO₂R⁺, wherein;

R⁺ is hydrogen, a $C_{1-6}$ aliphatic, phenyl, —O(Ph), —CH₂(Ph), —(CH₂)$_{1-2}$(Ph), —CH=CH(Ph); or an unsubstituted 5-6 membered heteroaryl or heterocyclic ring having one to four heteroatoms independently selected from oxygen, nitrogen, or sulfur, wherein said aliphatic group or said phenyl ring of R⁺ is optionally substituted with 1-3 independent occurrences of —NH₂, —NH($C_{1-4}$ aliphatic), —N($C_{1-4}$ aliphatic)₂, halogen, —$C_{1-4}$ aliphatic, —OH, —O($C_{1-4}$ aliphatic), —NO₂, —CN, —CO₂H, —CO₂($C_{1-4}$ aliphatic), —$C_{1-4}$haloalkyl, —$C_{1-4}$haloalkoxy, wherein said $C_{1-4}$ aliphatic groups of R⁺ are unsubstituted;

R² is an unsubstituted $C_{1-4}$ aliphatic group; and

R³ is selected from —Ar², —C(O)NHR^V, —C(O)N(R^V)₂, —C(O)R^V, —CO₂R^V, —C(O)C(O)N(R^V)₂, —SO₂R^V, —SO₂N(R^V)₂, —SO₂NHR^V, —C(R^V)=NOR^V, —C(R^V)=NOH, or —C(R^V)=NR^V; wherein each R^V is independently selected from -T-Ar¹ or a $C_{1-6}$ aliphatic group; wherein said $C_{1-6}$ aliphatic group is optionally substituted with 1-3 groups independently selected from —$R^W$, -T-Ar¹, oxo, thioxo, —CO₂$R^W$, —O$R^W$, —N($R^W$)₂, —S$R^W$, —NO₂, —$C_{1-4}$haloalkyl, —$C_{1-4}$haloalkoxy, halogen, —CN, —C(O)N($R^W$)₂, —N$R^W$C(O)$R^W$, —SO₂$R^W$, —SO₂N($R^W$)₂, —N$R^W$SO₂$R^W$, —N$R^W$CON($R^W$)₂, —N$R^W$CO₂$R^W$, —CO$R^W$, —OCO$R^W$, —OCON($R^W$)₂, —SO$R^W$, —N$R^W$SO₂N($R^W$)₂, —COCO$R^W$, —COCH₂CO$R^W$, —OP(O)(O$R^W$)₂, —P(O)(O$R^W$)₂, —OP(O)₂O$R^W$, —P(O)₂O$R^W$, —PO($R^W$)₂, or —OPO($R^W$)₂;

Ar² is a 5-6 membered heteroaryl ring having 1-4 heteroatoms independently selected from nitrogen, oxygen, or sulfur; or a 5-6 membered heterocyclic ring having 1-3 heteroatoms independently selected from nitrogen, oxygen, or sulfur; provided that said ring has a hydrogen-bond acceptor in the position adjacent to the point of attachment to Ring A;

wherein

Ar² is optionally substituted with 1-3 groups independent occurrences of —$R^W$, -T-Ar¹, oxo, thioxo, —CO₂$R^W$, —O$R^W$, —N($R^W$)₂, —S$R^W$, —NO₂, —$C_{1-4}$haloalkyl, —$C_{1-4}$haloalkoxy, halogen, —CN, —C(O)N($R^W$)₂, —N$R^W$C(O)$R^W$, —SO₂$R^W$, —SO₂N($R^W$)₂, —N$R^W$SO₂$R^W$, —N$R^W$CON($R^W$)₂, —N$R^W$CO₂$R^W$, —CO$R^W$, —OCO$R^W$, —OCON($R^W$)₂, —SO$R^W$, —N$R^W$SO₂N($R^W$)₂, —COCO$R^W$, —COCH₂CO$R^W$, —OP(O)(O$R^W$)₂, —P(O)(O$R^W$)₂, —OP(O)₂O$R^W$, —P(O)₂O$R^W$, —PO($R^W$)₂, or —OPO($R^W$)₂; or two substituents on adjacent positions of Ar² may be taken together to form a 3-8-membered saturated or partially unsaturated monocyclic ring or a 5-6 membered aryl ring having 0-3 heteroatoms independently selected from nitrogen, oxygen, or sulfur; wherein said 3-8-membered or said 5-6 membered ring is optionally substituted with 1-3 independent occurrences of $R^T$, -T-Ar³, halogen, oxo, thioxo, —O$R^T$, —S$R^T$, —N($R^T$)₂, —NO₂, —$C_{1-4}$haloalkyl, —$C_{1-4}$haloalkoxy, —CN, —CO₂$R^T$, —CO$R^T$, —CON($R^T$)₂, —OCO$R^T$, —N$R^T$CO$R^T$, —SO₂$R^T$, —SO₂N($R^T$)₂, or —N$R^T$SO₂$R^T$;

wherein any nitrogen atom in any of said rings is optionally substituted with —R⁺, —N(R⁺)₂, —COR⁺, —CO₂R⁺, —COCOR⁺, —COCH₂COR⁺, —SO₂R⁺, —SO₂N(R⁺)₂, —C(=S)N(R⁺)₂, —C(=NH)—N(R⁺)₂, or —NR⁺SO₂R⁺; and R⁴ is selected from hydrogen or halogen;

provided that the following compounds are excluded:
1-ethyl-3-(5-(2,3-dihydro-1-isopropyl-2-oxo-1H-imidazol-4-yl)-7-(pyrimidin-2-yl)-1H-benzo[d]imidazol-2-yl)urea; and
1-ethyl-3-(5-(1,1-dimethylurea)-7-(pyrimidin-2-yl)-1H-benzo[d]imidazol-2-yl)urea.

2. The compound according to claim 1, wherein R³ is Ar².

3. The compound according to claim 2, wherein Ar² is selected from the following optionally substituted rings:

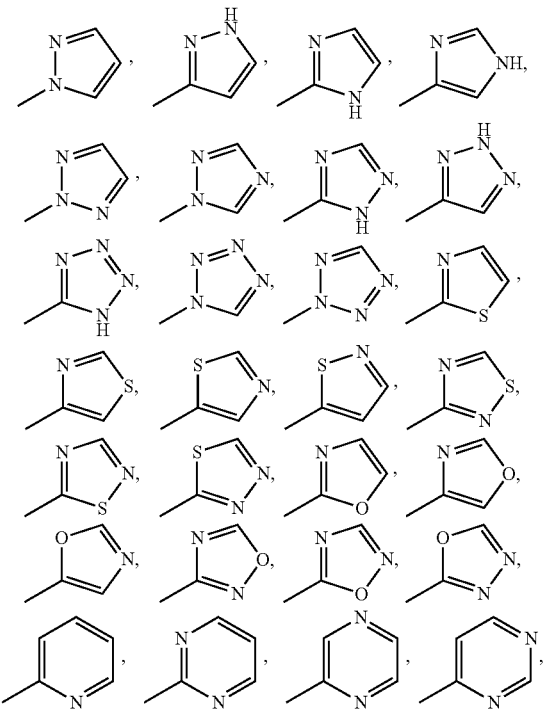

-continued

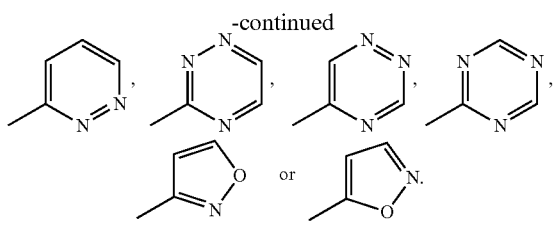

4. The compound according to claim 3, wherein Ar² is selected from the following optionally substituted rings:

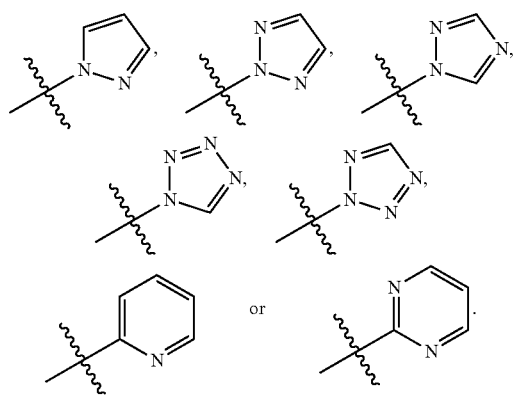

5. The compound according to claim 4, wherein Ar² is selected from the following optionally substituted rings:

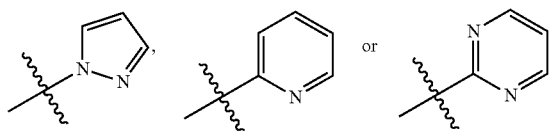

6. The compound according to claim 5, wherein Ar² is selected from the following rings:

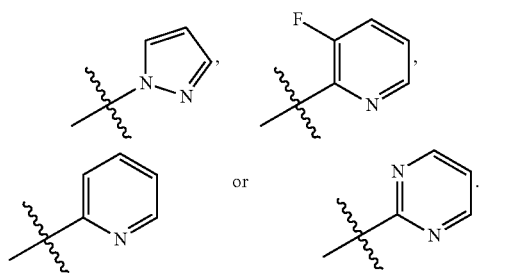

7. The compound according to claim 1, wherein R² is selected from methyl, ethyl, isopropyl, or cyclopropyl.

8. The compound according to claim 7, wherein R² is ethyl.

9. The compound according to claim 1, wherein Z is C—R⁴.

10. The compound according to claim 9, wherein R⁴ is hydrogen.

11. The compound according to claim 1, wherein X is C—R⁴.

12. The compound according to claim 11, wherein R⁴ is hydrogen.

13. The compound according to claim 1, wherein X is C—R⁴ and Z is C—R⁴.

14. The compound according to claim 13, wherein R⁴ is hydrogen.

15. The compound according to claim 1, wherein $R^1$ is $R^Y$.

16. The compound according to claim 15, wherein $R^Y$ is selected from —$R^K$, halogen, —CN, —OR', —N(R')₂, —NR'CON(R')₂, —NR'CO₂R', —CO₂R', or —CON(R')₂.

17. The compound according to claim 16, wherein $R^K$ is selected from hydrogen, C₁₋₆ aliphatic, C₃₋₁₀ cycloaliphatic, or a 3-8-membered saturated monocyclic ring having 0-3 heteroatoms independently selected from nitrogen, oxygen, or sulfur, or an 8-12 membered saturated bicyclic ring system having 0-5 heteroatoms independently selected from nitrogen, oxygen, or sulfur.

18. The compound according to claim 1, wherein said compound is of formula IIa, IIb, or IIc:

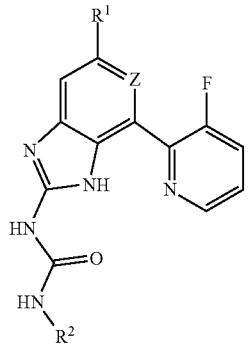

IIa

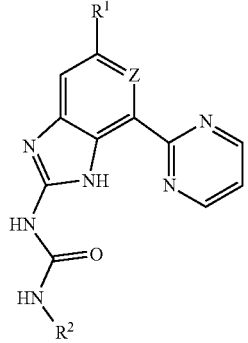

IIb

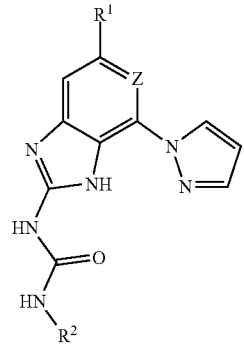

IIc or a pharmaceutically acceptable salt thereof.

19. A compound selected from:
I-1
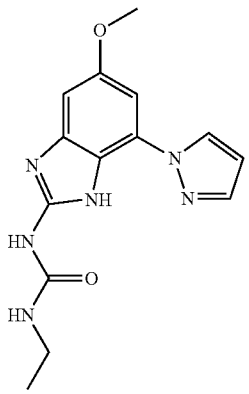
I-2
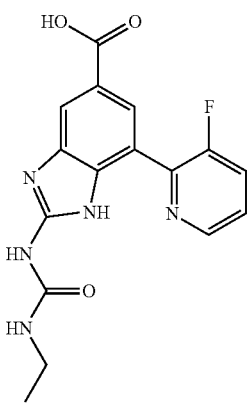
I-3
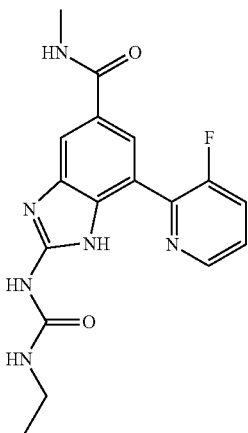
I-4
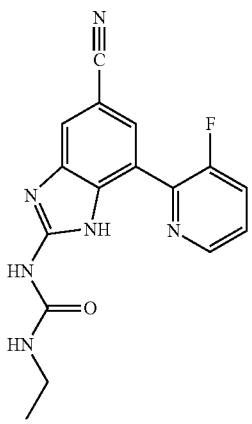
I-5
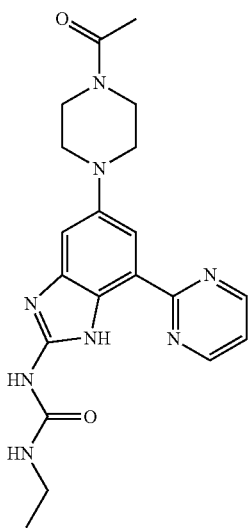
I-6
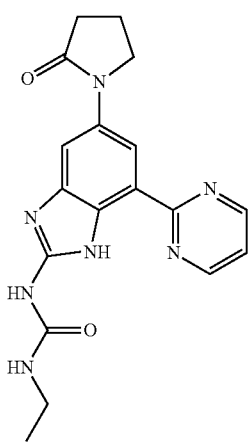

I-7
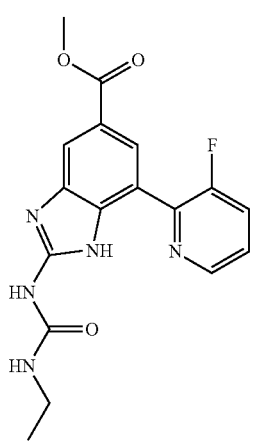
I-8
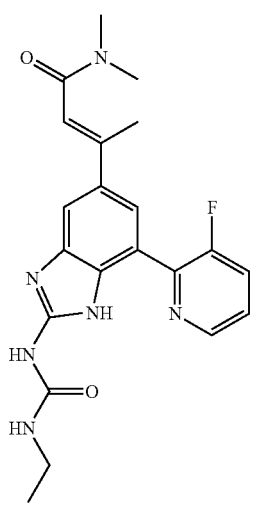
I-9
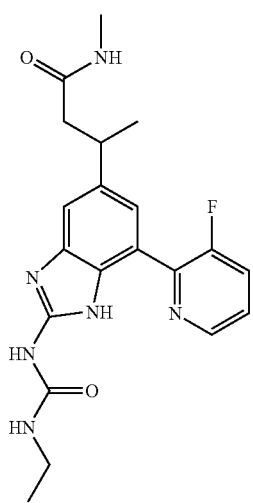
I-10
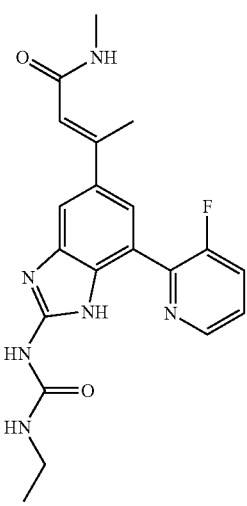
I-12
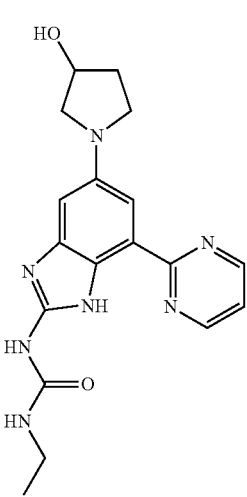
I-13
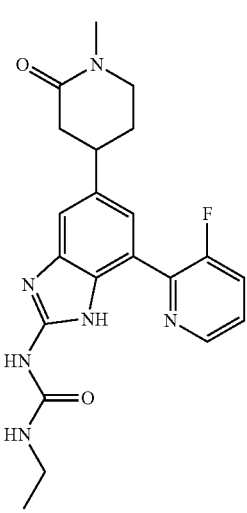

I-14
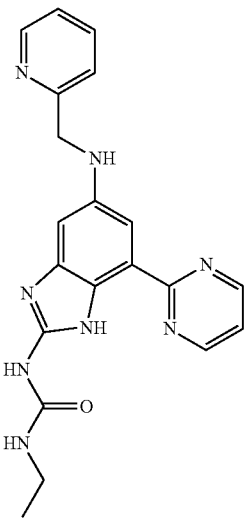
I-15
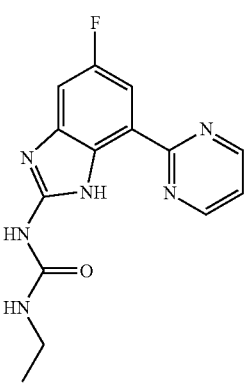
I-16
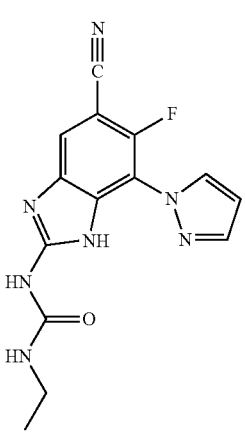
I-17
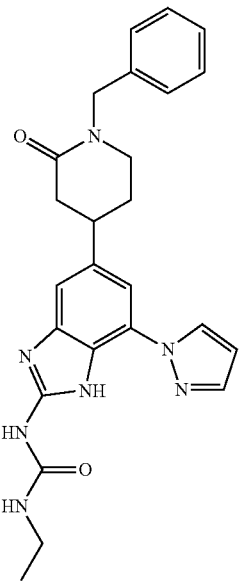
I-18
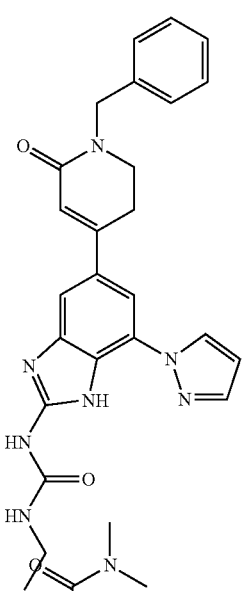
or
I-19
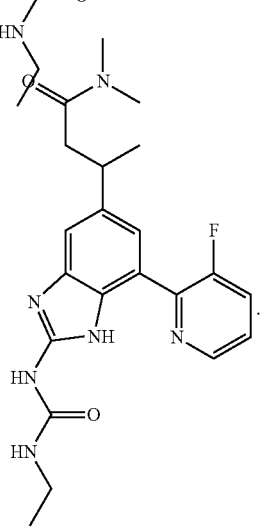
20. A composition comprising a compound according to claim 1, and a pharmaceutically acceptable carrier, adjuvant, or vehicle.

21. A method of treating or lessening the severity of a bacterial infection in a patient, comprising the step of administering to said patient a composition according to claim 20, wherein said bacterial infection is characterized by the presence of one or more of the following: *Streptococcus pneumoniae, Enterococcus faecalis*, or *Staphylococcus aureus*.

22. The method according to claim 21, further comprising the step of administering to said patient a therapeutic agent either as part of a multiple dosage form together with said composition or as a separate dosage form.

* * * * *